US011326202B2

(12) United States Patent
Zheng

(10) Patent No.: US 11,326,202 B2
(45) Date of Patent: May 10, 2022

(54) METHODS OF ENRICHING AND DETERMINING TARGET NUCLEOTIDE SEQUENCES

(71) Applicant: HELITEC LIMITED, Guangdong (CN)

(72) Inventor: Zongli Zheng, Hong Kong (HK)

(73) Assignee: HELITEC LIMITED, Shenzhen (CN)

( * ) Notice: Subject to any disclaimer, the term of this patent is extended or adjusted under 35 U.S.C. 154(b) by 157 days.

(21) Appl. No.: 16/198,902

(22) Filed: Nov. 23, 2018

(65) Prior Publication Data
US 2019/0078148 A1  Mar. 14, 2019

Related U.S. Application Data

(63) Continuation-in-part of application No. PCT/CN2017/095404, filed on Aug. 1, 2017.

(51) Int. Cl.
*C12Q 1/68* (2018.01)
*C12Q 1/6818* (2018.01)
*C12Q 1/6811* (2018.01)
*C12Q 1/6827* (2018.01)
*C12Q 1/6848* (2018.01)
*C12Q 1/6851* (2018.01)
*C12Q 1/6858* (2018.01)
*C12Q 1/686* (2018.01)
*C12Q 1/6876* (2018.01)
*C12Q 1/6869* (2018.01)
*C12Q 1/6806* (2018.01)
*C12Q 1/6809* (2018.01)

(52) U.S. Cl.
CPC ......... *C12Q 1/6818* (2013.01); *C12Q 1/6806* (2013.01); *C12Q 1/686* (2013.01); *C12Q 1/6809* (2013.01); *C12Q 1/6811* (2013.01); *C12Q 1/6827* (2013.01); *C12Q 1/6848* (2013.01); *C12Q 1/6851* (2013.01); *C12Q 1/6858* (2013.01); *C12Q 1/6869* (2013.01); *C12Q 1/6876* (2013.01); *C12Q 2521/119* (2013.01); *C12Q 2521/501* (2013.01); *C12Q 2525/151* (2013.01); *C12Q 2525/161* (2013.01); *C12Q 2525/173* (2013.01); *C12Q 2525/185* (2013.01); *C12Q 2525/191* (2013.01); *C12Q 2533/101* (2013.01); *C12Q 2537/163* (2013.01); *C12Q 2563/185* (2013.01)

(58) Field of Classification Search
None
See application file for complete search history.

(56) References Cited

U.S. PATENT DOCUMENTS

| 4,683,195 | A | 7/1987 | Mullis et al. |
|---|---|---|---|
| 4,683,202 | A | 7/1987 | Mullis |
| 6,172,218 | B1 | 1/2001 | Brënner |
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,818,395 | B1 | 11/2004 | Quake et al. |
| 6,911,345 | B2 | 6/2005 | Quake et al. |
| 6,969,488 | B2 | 11/2005 | Bridgham et al. |
| 7,001,792 | B2 | 2/2006 | Sauer et al. |
| 7,057,026 | B2 | 6/2006 | Barnes et al. |
| 7,169,560 | B2 | 1/2007 | Lapidus et al. |
| 7,181,122 | B1 | 2/2007 | Levene et al. |
| 7,211,414 | B2 | 5/2007 | Hardin et al. |
| 7,220,549 | B2 | 5/2007 | Buzby |
| 7,226,720 | B2 | 6/2007 | Wisnudel et al. |
| 7,279,563 | B2 | 10/2007 | Kwiatkowski |
| 7,282,337 | B1 | 10/2007 | Harris |
| 7,302,146 | B2 | 11/2007 | Turner et al. |
| 7,313,308 | B2 | 12/2007 | Turner et al. |
| 7,315,019 | B2 | 1/2008 | Turner et al. |
| 7,329,492 | B2 | 2/2008 | Hardin et al. |
| 7,405,281 | B2 | 7/2008 | Ku et al. |
| 7,414,116 | B2 | 8/2008 | Milton et al. |
| 7,427,673 | B2 | 9/2008 | Balasubramanian et al. |
| 8,241,573 | B2 | 8/2012 | Banerjee et al. |
| 9,487,828 | B2 * | 11/2016 | Iafrate ..................... A61P 35/00 |
| 2005/0100900 | A1 | 5/2005 | Kawashima et al. |
| 2006/0188901 | A1 | 8/2006 | Barnes et al. |
| 2006/0240439 | A1 | 10/2006 | Smith et al. |
| 2006/0252077 | A1 | 11/2006 | Buzby |

(Continued)

FOREIGN PATENT DOCUMENTS

WO  91/06678 A1  5/1991
WO  2005/065814 A1  7/2005

(Continued)

OTHER PUBLICATIONS

Zheng Z, Liebers M, Zhelyazkova B, Cao Y, Panditi D, Lynch KD, Chen J, Robinson HE, Shim HS, Chmielecki J, Pao W, Engelman JA, Iafrate AJ, Le LP. Anchored multiplex PCR for targeted next-generation sequencing. Nat Med. Dec. 2014; 20(12):1479-84. Epub Nov. 10, 2014. (Year: 2014).*

Sandberg J. Massively parallel analysis of cells and nucleic acids (Doctoral dissertation, KTH Royal Institute of Technology). (Year: 2011).*

Hoeijmakers WA, Bártfai R, Françoijs KJ, Stunnenberg HG. Linear amplification for deep sequencing. Nature protocols. Jul. 2011;6(7):1026. (Year: 2011).*

(Continued)

*Primary Examiner* — Gary Benzion
*Assistant Examiner* — Olayinka A Oyeyemi

(57) ABSTRACT

The present invention provides methods, compositions and kits for enriching and determining nucleotide sequences of a plurality of target loci from a sample comprising nucleic acids. The methods comprise one or more cycles of primer extension followed by PCR amplification of target sequences using nested target-specific primers.

24 Claims, 22 Drawing Sheets

Specification includes a Sequence Listing.

(56) References Cited

U.S. PATENT DOCUMENTS

| | | | |
|---|---|---|---|
| 2006/0281109 | A1 | 12/2006 | Barr Ost et al. |
| 2007/0070349 | A1 | 3/2007 | Harris et al. |
| 2007/0166705 | A1 | 7/2007 | Milton et al. |
| 2008/0108082 | A1 | 5/2008 | Rank et al. |
| 2013/0303461 | A1* | 11/2013 | Iafrate .............. A61P 35/00 514/19.3 |
| 2020/0048692 | A1* | 2/2020 | Zheng ............... C12Q 1/6844 |

FOREIGN PATENT DOCUMENTS

| | | |
|---|---|---|
| WO | 2006/064199 A1 | 6/2006 |
| WO | 2007/010251 A2 | 1/2007 |
| WO | 2007/123744 A2 | 11/2007 |
| WO | 2015/112948 A2 | 7/2015 |

OTHER PUBLICATIONS

S. Goodwin et al., Coming of Age: Ten Years of Next-generation Sequencing Technologies, Nature Reviews Genetics, Jun. 2016, pp. 333-351, vol. 17.
L. Mamanova et al., Target-enrichment Strategies for Next-generation Sequencing, Natural Methods, Feb. 2010, pp. 111-118, vol. 7, No. 2.
Innis et al., PCR Protocols: A Guide to Methods and Applications, eds, 1990, pp. 4-5.
Sambrook et al., In Vitro Amplification of DNA by the Polymerase Chain Reaction, Molecular Cloning: A Laboratory Manual (3 ed.), 2001, Chapter 8, Cold Spring Harbor Laboratory Press, Cold Spring Harbor, N.Y., USA.
Davis et al., Basic Methods in Molecular Biology, 1995, Sections 3-1 to 3-3, pp. 14-21, Elsevier Science Publishing, Inc., New York, USA.
S.M. Freier et al., Improved Free-energy Parameters for Predictions of RNA Duplex Stability, Proc. Natl. Acad. Sci. Dec. 1986, pp. 9373-9377, vol. 83.
Margulies, M. et al., Genome Sequencing in Microfabricated High-Density Picolitre Reactors, Nature, Sep. 15, 2005, pp. 376-380, vol. 437.
Mikkelsen, T.S. et al., Genome-Wide Maps of Chromatin State in Pluripotent and Lineage-Committed Cells, Nature, Aug. 2, 2007, pp. 553-560, vol. 448.
McLaughlin, S.F. et al., Whole-Genome Resequencing with Short Reads: Accurate Mutation Discovery with Mate Pairs and Quality Values, 2007, ASHG Annual Meeting.
Jay Shendure et al., Accurate Multiplex Polony Sequencing of an Evolved Bacterial Genome, Science, Sep. 9, 2005, pp. 1728-1732, vol. 309.
Harris T.D. et al., Single-Molecule DNA Sequencing of a Viral Genome, Science, Apr. 4, 2008, pp. 106-109, vol. 320.
Simen, B.B. et al., Low-Abundance Drug-Resistant Viral Variants in Chronically HIV-infected, Antiretroviral Treatment-Naive Patients Significantly Impact Treatment Outcomes, The Journal of Infectious Diseases, Mar. 1, 2009, pp. 693-701, vol. 199.
Thomas, R.K. et al., Sensitive Mutation Detection in Heterogeneous Cancer Specimens by Massively Parallel Picoliter Reactor Sequencing, Nature Medicine, Jul. 2006, pp. 852-855, vol. 12, No. 7.
Mitsuya, Y et al., Minority Human Immunodeficiency Virus Type I Variants in Antiretroviral-Naive Persons with Reverse Transcriptase Codon 215 Revertant Mutations, Journal of Virology, Nov. 2008, pp. 10747-10755, vol. 82, No. 21.
Binladen, J. et al., The Use of Coded PCR Primers Enables High-Throughput Sequencing of Multiple Homolog Amplification Products by 454 Parallel Sequencing, PLoS ONE, Feb. 14, 2007, pp. 1-9, Issue 2 , e197.
Hoffmann, C. et al., DNA Bar Coding and Pyrosequencing to Identify Rare HIV Drug Resistance Mutations, Nucleic Acids Research, Jun. 18, 2007, pp. 1-8, vol. 35, No. 13, e91.

Brownie, J. et al., The Elimination of Primer-dimer Accumulation in PCR, Nucleic Acids Research, 1997, pp. 3235-3241, vol. 25, No. 16.
Jay Shendure, et al., Next-generation DNA Sequencing, Nature Biotechnology, Oct. 2008, pp. 1135-1145, vol. 26, No. 10.
Mardis, E.R., The Impact of Next-generation Sequencing Technology on Genetics, Trends in Genetics, 2007, pp. 133-141, vol. 24, No. 3.
Zhenqiang Su, et al., Next-generation Sequencing and Its Applications in Molecular Diagnostics, Expert Review of Molecular Diagnostics, 2011, pp. 333-343, vol. 11, No. 3.
Jun Zhang et al., The Impact of Next-generation Sequencing on Genomics, J Genet Genomics, Mar. 20, 2011, pp. 95-109, vol. 38, No. 3.
Nyren, P. et al. Solid Phase DNA Minisequencing by an Enzymatic Luminometric Inorganic Pyrophosphate Detection Assay, Analytical Biochemistry, 1993, pp. 171-175, vol. 208.
Strausberg, R.L., et al., Emerging DNA Sequencing Technologies for Human Genomic Medicine, Drug Discovery Today, Jul. 2008, pp. 569-577, vol. 13, Nos. 13-14.
Ronaghi, M et al., Real-Time DNA Sequencing Using Detection of Pyrophosphate Release, Analytical Biochemistry, 1996, pp. 84-89, vol. 242.
Ronaghi, M., Pyrosequencing Sheds Light on DNA Sequencing, Genome Research, pp. 3-11, vol. 11.
Ronaghi, M. et al., A Sequencing Method Based on Real-Time Pyrophosphate, Science, Jul. 17, 1998, pp. 363-365, vol. 281, No. 5375.
Deamer, D.W. et al., Nanopores and Nucleic Acids: Prospects for Ultrarapid Sequencing, TIBTECH, Apr. 2000, pp. 147-151, vol. 18.
Deamer, D.W. et al., Characterization of Nucleic Acids by Nanopore Analysis, Accounts of Chemical Research, Sep. 27, 2002, pp. 817-825, vol. 35, No. 10.
Jiali Li et al., DNA Molecules and Configurations in a Solid-state Nanopore Microscope, Nat. Mater, 2003, pp. 611-615, vol. 2.
Soni, G.V. et al., Progress toward Ultrafast DNA Sequencing Using Solid-state Nanopores, Clinical Chemistry, 2007, pp. 1996-2001, vol. 53, No. 11.
Healy, K., Nanopore-based Single-molecule DNA Analysis, Nanomedicine, 2007, pp. 459-481, vol. 2, No. 4.
Cockroft, S.L. et al., A Single-Molecule Nanopore Device Detects DNA Polymerase Activity with Single-Nucleotide Resolution, J Am Chem Soc. Jan. 23, 2008, pp. 818-820, vol. 130, No. 3.
Levene, M.J. et al., Zero-Mode Waveguides for Single-Molecule Analysis at High Concentrations, Science, Jan. 31, 2003, pp. 682-686, vol. 299.
Lundquist, P.M. et al., Parallel Confocal Detection of Single Molecules in Real Time, Optics Letters, May 1, 2008, pp. 1026-1028, vol. 33, No. 9.
Korlach, J. et al., Selective Aluminum Passivation for Targeted Immobilization of Single DNA Polymerase Molecules in Zero-mode Waveguide Nanostructures, PNAS, Jan. 29, 2008, pp. 1176-1181, vol. 105, No. 4.
Korlach, J. et al., Long, Processive Enzymatic DNA Synthesis Using 100% Dye-labeled Terminal Phosphate-linked Nucleotides, Nucleosides, Nucleotides and Nucleic Acids, 2008, pp. 1072-1083, vol. 27.
Soda, M. et al., Identification of the Transforming EML4-ALK Fusion Gene in Non-small-cell Lung Cancer, Nature, Aug. 2, 2007, pp. 561-566, vol. 448.
Takeuchi, K. et al., RET, ROS1 and ALK Fusions in Lung Cancer, Nature Medicine, Feb. 12, 2012, pp. 378-381, vol. 18.
Zongli Zheng et al., Anchored Multiplex PGR for Targeted Next-generation Sequencing, Nature Medicine, Nov. 10, 2014, pp. 1479-1484, No. 12, vol. 20.
Bentley, D.R., Whole-genome Re-sequencing, Current Opinion in Genetics & Development, 2006, pp. 545-552, vol. 16.
Rikova, K. et al., Global Survey of Phosphotyrosine Signaling Identifies Oncogenic Kinases in Lung Cancer, Cell, Dec. 14, 2007, pp. 1190-1203, vol. 131.
Kohno, T. et al., KIF5B-RET Fusions in Lung Adenocarcinoma, Nature Medicine, Mar. 2012, pp. 375-377, vol. 18, No. 3.

(56) References Cited

OTHER PUBLICATIONS

International Search Report of PCT Patent Application No. PCT/CN2017/095404 dated May 4, 2018.

\* cited by examiner

FIG. 9D

METHODS OF ENRICHING AND DETERMINING TARGET NUCLEOTIDE SEQUENCES

CROSS-REFERENCE TO RELATED APPLICATIONS

The present application is a Continuation-in-part Application of PCT application No. PCT/CN2017/095404 filed on Aug. 1, 2017, the contents of the above are hereby incorporated by reference.

FIELD OF THE INVENTION

The present invention relates to the field of genomics, in particular, methods of enriching and determining nucleotide sequences.

SUBMISSION OF SEQUENCE LISTING ON ASCII TEXT FILE

The Sequence Listing is submitted as an ASCII formatted text file via EFS-Web, with a file name of "Sequence_listing.txt", a creation date of Nov. 22, 2018, and a size of 16,908 bytes. The Sequence Listing filed via EFS-Web is part of the specification and is incorporated in its entirety by reference herein.

BACKGROUND OF THE INVENTION

The next-generation sequencing (NGS) technologies have revolutionized the field of genomics in the past decade. Each NGS run routinely produces gigabases of sequence information on up to hundreds of thousands to billions of DNA templates in parallel per sequencing run. The present cost for sequencing a human genome has already reached the benchmark of $1,000. The low cost and high throughput of NGS technologies have enabled use of nucleic acid sequencing as a clinical tool.

However, there still remains a multitude of challenges to achieve the desirable cost, speed, analytical sensitivity, and accuracy required by clinical applications of NGS. Major NGS platforms today have relatively short reads (35-700 bp), high error rates (~0.1-15%), and platform-dependent bias. Clinical samples, such as biopsy and formalin-fixed paraffin-embedded (FFPE) samples, provide only low quantities of starting material. Rare genetic variants may require up to 100,000× coverage for detection. See, for example, S. Goodwin et al., Nat. Rev. Genetics (2016), 17:333.

Targeted sequencing provides sequencing data with suitable breadth and depth to allow detection of clinically relevant genetic variants. A key step of this approach is target enrichment, which selectively capture target regions from a nucleic acid sample, such as a genomic DNA sample, before sequencing. Various known target enrichment methods, including microdroplet-based PCR, molecular inversion probes and hybridization-capture approach, require a large amount of input template, specialized instrumentation or bait design, and biased sequence coverage. See, L. Mamanova et al., Nat. Methods (2010), 7(2): 111.

The disclosures of all publications, patents, patent applications and published patent applications referred to herein are hereby incorporated herein by reference in their entirety.

BRIEF SUMMARY OF THE INVENTION

The present invention provides methods, compositions, kits and analysis systems for enriching and determining nucleotide sequences.

One aspect of the present application provides a method of enriching a target nucleotide sequence having a locus of interest from a nucleic acid sample comprising a nucleic acid template comprising the target nucleotide sequence, the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the target nucleotide sequence; (c) annealing an outside primer to the first strand of the ligated nucleic acid in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) repeating steps (c)-(e) for one or more primer extension cycles; (g) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; and (h) repeating step (g) for one or more cycles of PCR amplification to provide amplicons of the target nucleotide sequence, thereby enriching the target nucleotide sequence. In some embodiments, the amplicons of the target nucleotide sequence are used for next-generation sequencing (NGS).

In some embodiments according to any one of the methods described above, the method comprises enriching a target nucleotide sequence having the locus of interest using a first set of outside primer and inside primer that can specifically anneal to the first strand of the ligated nucleic acid, and a second set of outside primer and inside primer that can specifically anneal to the second strand of the ligated nucleic acid. In some embodiments, the outside primer of the first set and the outside primer of the second set comprises a first 5' tag sequence of at least about 13 nucleotides long, and wherein the inside primer of the first set and the inside primer of the second set comprises a second 5' tag sequence of at least about 13 nucleotides long. In some embodiments, the GC content of the first 5' tag sequence is substantially similar to the GC content of the nucleic acid template.

In some embodiments according to any one of the methods described above, the method comprises enriching a plurality of target nucleotide sequences having different loci of interest using a plurality of sets of outside primer and inside primer. In some embodiments, at least 2 of the plurality of target nucleotide sequences are present in different strands of the nucleic acid template. In some embodiments, the method comprises enriching a plurality of target nucleotide sequences having about 2-5000 different loci of interest.

In some embodiments according to any one of the methods described above, steps (c)-(e) are repeated for about 2-100 cycles. In some embodiments, the outside primer anneals to a region about 1-100 nucleotides farther away from the locus of interest than the inside primer. In some embodiments, at least the last 12 nucleotides of the outside primer and/or the inside primer have fewer than about 20 different annealing loci in the nucleic acid sample.

In some embodiments according to any one of the methods described above, the nucleic acid template is genomic DNA. In some embodiments, the genomic DNA is chromosomal DNA. In some embodiments, the genomic DNA is mitochondrial DNA or other extra-chromosomal DNA. In some embodiments, the nucleic acid template is exome DNA. In some embodiments, the nucleic acid template is cDNA. In some embodiments, the cDNA is obtained by reverse transcription of total RNA. In some embodiments, the cDNA is obtained by reverse transcription of mRNA, miRNA, or other non-coding RNAs. In some embodiments, the nucleic acid sample comprises both genomic DNA and cDNA. In some embodiments, the nucleic acid template is cell-free DNA.

In some embodiments according to any one of the methods described above, the nucleic acid sample is derived from a blood sample. In some embodiments, the nucleic acid sample is derived from a cell or tissue sample. In some embodiments, the nucleic acid sample is derived from a tumor biopsy sample. In some embodiments, the nucleic acid sample is derived from a Formalin-Fixed Paraffin-Embedded (FFPE) sample.

In some embodiments according to any one of the methods described above, the locus of interest is associated with a chromosomal rearrangement. In some embodiments, the chromosomal rearrangement is chromosomal translocation. In some embodiments, the locus of interest is associated with a single nucleotide variant (SNV). In some embodiments, the locus of interest is associated with an indel. In some embodiments, the locus of interest is associated with a splice variant.

In some embodiments according to any one of the methods described above, the locus of interest is located in a gene associated with cancer. In some embodiments, the locus of interest is located in a gene encoding an immune cell receptor. In some embodiments, the locus of interest is located in a gene associated with a hereditary disease. In some embodiments, the locus of interest is located in an off-target site (e.g., previously known or unknown off-target site) of CRISPR gene editing.

In some embodiments according to any one of the methods described above, the nucleic acid template is fragmented to a size suitable for the next-generation sequencing. In some embodiments, the method further comprises end repairing and A-tailing of the nucleic acid template prior to step (a).

In some embodiments according to any one of the methods described above, the non-duplex portion of the universal adaptor comprises a 3' end having a blocking moiety. In some embodiments, the blocking moiety is an inverted nucleotide. In some embodiments, the blocking moiety is a stretch of flapping nucleotides having one or more phosphorothioate modifications.

In some embodiments according to any one of the methods described above, the non-duplex portion of the universal adaptor comprises a molecular barcode comprising degenerately designed nucleobases. In some embodiments, the duplex portion of the universal adaptor comprises a sample barcode. In some embodiments, the sample barcode is located at the first end of the universal adaptor. In some embodiments, the sample barcode consists of about 4-13 nucleotides. In some embodiments, the first end of the universal adaptor comprises constant nucleobases of a sufficiently short length to prevent promiscuous priming during steps (b)-(f) by carryover universal adaptor.

In some embodiments according to any one of the methods described above, the sufficiently high temperature is at least about 90° C. In some embodiments, the ligated nucleic acid is subjected to a cleanup procedure prior to step (b). In some embodiments, the primer extension products are subjected to a cleanup procedure prior to step (g). In some embodiments, step (g) is repeated for about 2-100 cycles.

In some embodiments according to any one of the methods described above, the universal adaptor or the 5' end of the universal adaptor primer comprises a sequence identical or complementary to the sequence of a first sequencing primer for the NGS. In some embodiments, step (g) comprises contacting the single-stranded primer extension products with a DNA polymerase, a universal adaptor primer, an inside primer, and a sequencing adaptor primer under a condition sufficient for PCR amplification of the target nucleotide sequence, wherein the sequencing adaptor primer comprises at the 3' end a sequence identical to a sequence of the inside primer, and at the 5' end a sequence identical or complementary to the sequence of a second sequencing primer for the NGS.

One aspect of the present application provides a method of determining a target nucleotide sequence having a locus of interest in a nucleic acid sample comprising a nucleic acid template comprising the target nucleotide sequence, the method comprising: (i) enriching the target nucleotide sequence having the locus of interest using any one of the methods described above; and (ii) performing next-generation sequencing of the amplicons of the target nucleotide sequence, thereby providing the target nucleotide sequence. In some embodiments, target nucleotide sequences having about 2-5000 different loci of interest are determined simultaneously. In some embodiments, the method further comprises preparing a sequencing library using the amplicons of the target nucleotide sequence prior to the next-generation sequencing of step (ii).

Another aspect of the present application provides a method of detecting a sequence variant at a locus of interest in a nucleic acid sample comprising a nucleic acid template comprising a target nucleotide sequence having the locus of interest, the method comprising: (1) determining the target sequence having the locus of interest using any one of the methods of determining target nucleotide sequences described above; and (2) detecting the sequence variant in the target nucleotide sequence. In some embodiments, the sequence variant is present at an allele frequency of no more than about 1:100 (such as no more than about any one of 1:1000, 1:10000, or lower). In some embodiments, the sequence variant is inherited in germline DNA. In some embodiments, the sequence variant is a somatic mutation or chromosomal rearrangement. In some embodiments, a plurality of sequence variants are detected. In some embodiments, the plurality of sequence variants are selected from the group consisting of chromosomal rearrangements, splice variants, SNP, deletions, insertions, copy number variants (CNV), and combinations thereof. In some embodiments, the method simultaneously detects a chromosomal rearrangement based on cDNA sequences, and a mutation based on gDNA sequences.

Another aspect of the present application provides a method of diagnosing a disease in an individual, comprising detecting a sequence variant associated with the disease at a locus of interest in a nucleic acid sample from the individual using any one of the methods of detecting sequence variants described above, thereby providing a diagnosis of the disease.

Further provided by the present application is a kit comprising: (a) a universal adaptor, wherein the universal adaptor is an oligonucleotide comprising a ligatable duplex portion at a first end and a non-duplex portion at a second end; (b) a universal adaptor primer, wherein the universal adaptor primer is capable of annealing to a complementary sequence of the non-duplex portion of the universal adaptor; (c) an outside primer; and (d) an inside primer; wherein the inside primer is nested with respect to the outside primer for a locus of interest. In some embodiments, the universal adaptor or the 5' end of the universal adaptor primer comprises a sequence that is identical or complementary to the sequence of a first sequencing primer compatible with an NGS platform. In some embodiment, the inside primer comprises a sequence identical or complementary to the sequence of a second sequencing primer compatible with the NGS platform. In some embodiments, the kit further comprises a sequence adaptor primer comprising at the 3' end a sequence identical to a sequence of the inside primer and at the 5' end a sequence identical or complementary to the sequence of a second sequencing primer compatible with the NGS platform. In some embodiments, the kit comprises a plurality of sets of outside primer and inside primer.

In some embodiments according to any one of the kits described above, the kit is used for diagnosis of a cancer. In some embodiments, the cancer is lung cancer, breast cancer, or colorectal cancer. In some embodiments, the locus of interest is located in any one or more of the genes selected from the group consisting of ALK, BRAF, EGFR, ERBB2, HRAS, KDR, KIT, KRAS, MET, NRAS, NTRK1, PDGFRA, PIK3CA, PTEN, RET, ROS1, and TP53.

These and other aspects and advantages of the present invention will become apparent from the subsequent detailed description and the appended claims. It is to be understood that one, some, or all of the properties of the various embodiments described herein may be combined to form other embodiments of the present invention just as if each and every combination was individually and explicitly disclosed.

BRIEF DESCRIPTION OF THE DRAWINGS

FIG. 9D shows coverage on KRAS exon 2 by mapped reads from sequencing libraries L17-00172 to L17-00177.

DETAILED DESCRIPTION OF THE INVENTION

Figure 1:
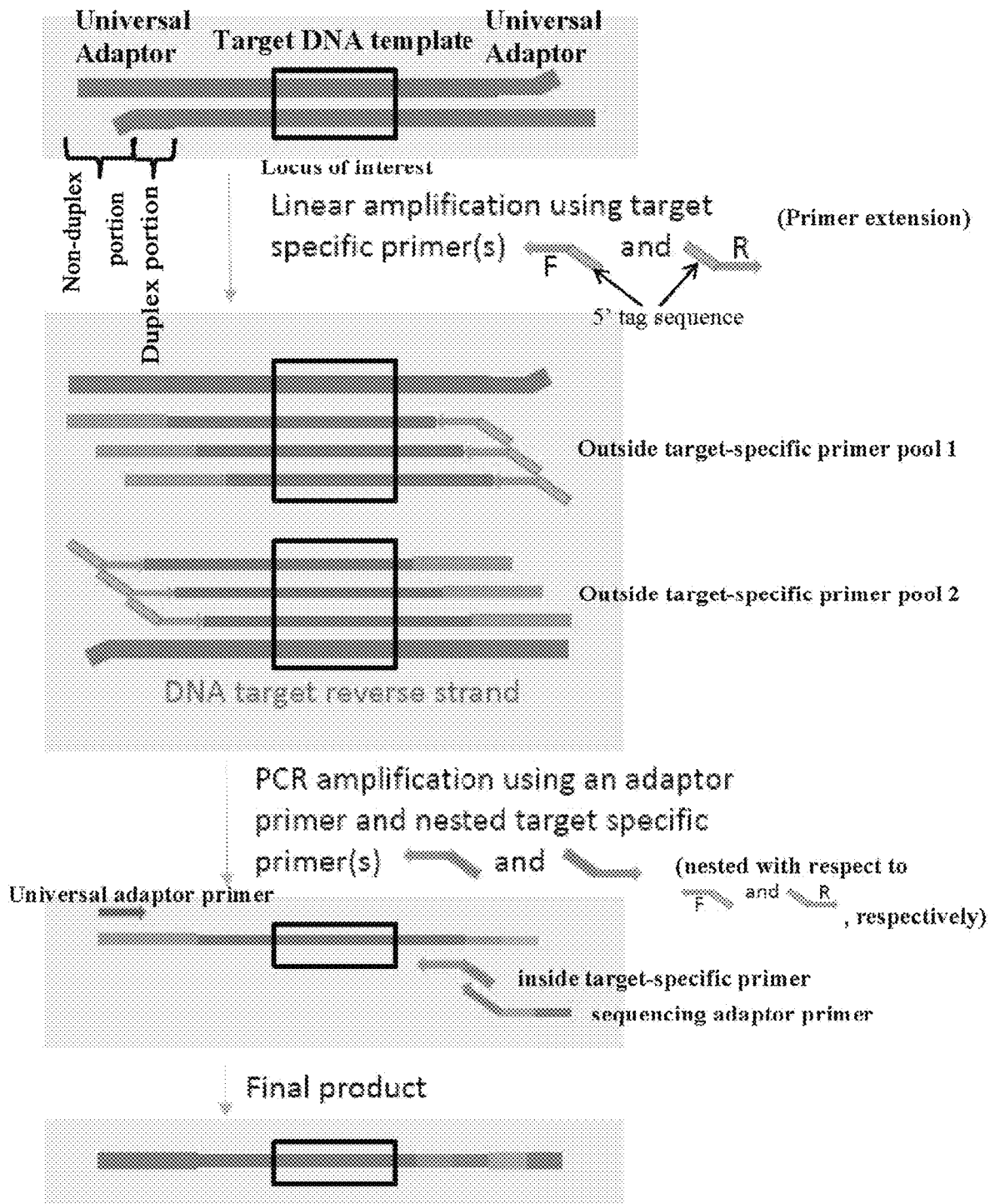
FIG. 1 is a schematic presentation of an exemplary method of preparation of a sequencing library with enrichment of a target nucleotide sequence.

The present application provides methods for enriching and determining target nucleotide sequences having one or more loci of interest comprising ligation of nucleic acid templates to a universal adapter, a primer extension step (or a linear amplification step) followed by a PCR amplification step (or an exponential amplification step) using nested target-specific primers. The methods described herein provide an improved method of target enrichment for highly efficient construction of sequencing libraries with increased sequence diversity, even using very low amount of input nucleic acid samples. The primer extension step of the methods described herein allows linear amplification of target nucleotide sequences, and the PCR amplification step allows exponential and target-specific amplification of the target nucleotide sequences from the primer extension products. Previously, Anchored-multiplex PCR (AMP) has been developed to enrich target nucleic acids through two-step PCR amplifications using nested target-specific primers. See, e.g., International PCT application publication No. WO2015112948. However, as amplicons are enriched exponentially in both amplification steps of the AMP approach, amplification bias and errors can be propagated to compromise enrichment efficiency and accuracy. The present application provides data using the methods described herein that demonstrate superior efficiency, specificity and sensitivity over the AMP approach. Additionally, the methods described herein enable simultaneous RNA-based and gDNA-based detection of sequences variants, and multiplexed interrogation of a larger number of target loci compared to other target enrichment approaches. Such properties are especially desirable for clinical applications of the methods described herein, which require cost-effective, rapid and accurate detection of often rare genetic variants associated with diseases from scarce clinical samples having low-quality nucleic acids.

Accordingly, one aspect of the present application provides a method of enriching a target nucleotide sequence having a locus of interest from a nucleic acid sample comprising a nucleic acid template comprising the target nucleotide sequence (e.g., for next-generation sequencing), the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the target nucleotide sequence; (c) annealing an outside primer to the first strand of the ligated nucleic acid in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) repeating steps (c)-(e) for one or more primer extension cycles; (g) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; and (h) repeating step (g) for one or more cycles of PCR amplification to provide amplicons of the target nucleotide sequence, thereby enriching the target nucleotide sequence.

Another aspect of the present application provides a method of determining a target nucleotide sequence having a locus of interest in a nucleic acid sample comprising a nucleic acid template comprising the target nucleotide sequence, the method comprising: (a) ligating a universal adaptor to the nucleic acid template to provide ligated nucleic acids, wherein the universal adaptor is an oligonucleotide comprising a duplex portion at a first end and a non-duplex portion at a second end, and wherein the nucleic acid template is ligated to the universal adaptor via the first end; (b) dissociating each ligated nucleic acid comprising the locus into a first strand and a second strand, wherein the first strand comprises the target nucleotide sequence; (c) annealing an outside primer to the first strand of the ligated nucleic acid in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) repeating steps (c)-(e) for one or more primer extension cycles; (g) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; (h) repeating step (g) for one or more cycles of PCR amplification to provide amplicons of the target nucleotide sequence; and (i) performing next-generation sequencing of the amplicons of the target nucleotide sequence, thereby providing the target nucleotide sequence.

Further provided are methods of preparing sequencing libraries, methods of detecting sequence variants, and methods of diagnosis and treatment of diseases, as well as compositions, kits, articles of manufacture, and analysis software for use in the methods.

I. Definition

"Polynucleotides" or "nucleic acids" as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs.

"Oligonucleotide," as used herein, generally refers to short, generally single-stranded, generally synthetic polynucleotides that are generally, but not necessarily, no more than about 200 nucleotides in length. The terms "oligonucleotide" and "polynucleotide" are not mutually exclusive. The description above for polynucleotides is equally and fully applicable to oligonucleotides.

The term "3'" generally refers to a region or position in a polynucleotide or oligonucleotide that is downstream of another region or position in the same polynucleotide or oligonucleotide.

The term "5'" generally refers to a region or position in a polynucleotide or oligonucleotide that is upstream from another region or position in the same polynucleotide or oligonucleotide.

A "nucleic acid template" as used herein refers to a polynucleotide present in a nucleic acid sample that serves as the starting material for target enrichment and sequencing.

A "template nucleic acid" refers to a polynucleotide that serves as the template in a primer extension reaction or a PCR amplification reaction. A template nucleic acid may refer to either a duplex or a strand thereof.

A "locus of interest" refers to a polynucleotide such as a segment of a gene or gene fusion product that is of interest to the investigator. A locus can have any number of nucleotides, including a single nucleotide. A locus may be associated with one or more different sequences.

A "target nucleotide sequence having a locus of interest" refers to a nucleotide sequence of a polynucleotide that encompasses or is encompassed by the locus of interest. The target nucleotide sequence can be a sequence on the plus strand, or the minus strand of the polynucleotide. The polynucleotide can be longer than or shorter than the locus of interest.

A nucleic acid or primer is "complementary" to another nucleic acid when at least two contiguous bases of, e.g., a first nucleic acid or a primer, can combine in an antiparallel association or hybridize with at least a subsequence of a second nucleic acid to form a duplex. In some embodiment, complementary refers to hydrogen-bonded base pair formation preferences between the nucleotide bases G, A, T, C and U, such that when two given polynucleotides or nucleotide sequences anneal to each other, A pairs with T and G pairs with C in DNA, and G pairs with C and A pairs with U in RNA. As used herein, "substantially complementary" refers to a nucleic acid molecule or portion thereof (e.g. a primer) having at least 90% complementarity over the entire length of the molecule or portion thereof with a second nucleotide sequence, e.g. 90% complementary, 95% complementary, 98% complementary, 99% complementary, or 100% complementary. As used herein, "substantially identical" refers to a nucleic acid molecule or portion thereof having at least 90% identity over the entire length of the molecule or portion thereof with a second nucleotide sequence, e.g. 90% identity, 95% identity, 98% identity, 99% identity, or 100% identity.

A "primer" is generally a short single-stranded polynucleotide, generally with a free 3'-OH group, that binds to a target of interest by hybridizing with a target sequence, and thereafter promotes polymerization of a polynucleotide complementary to the target.

"Hybridization" and "annealing" as used interchangeably herein refer to a reaction in which one or more polynucleotides react to form a complex that is stabilized via hydrogen bonding between the bases of the nucleotide residues. The hydrogen bonding may occur by Watson-Crick base pairing, Hoogstein binding, or by any other sequence specific manner.

As used herein, the term "hybridize specifically" or "anneal specifically" means that nucleic acids hybridize with a nucleic acid of complementary sequence. As used herein, a portion of a nucleic acid molecule may hybridize specifically with a complementary sequence on another nucleic acid molecule. That is, the entire length of a nucleic acid sequence does not necessarily need to hybridize for a portion of such sequence to be "specifically hybridized" to another molecule, there may be, for example, a stretch of nucleotides at the 5' end of a molecule that do not hybridize while a stretch at the 3' end of the same molecule is specifically hybridized to another molecule.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

As used herein, "specific" when used in the context of a primer specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

An "inside primer" and a corresponding "outside primer" refer to two nested target-specific primers designed to carry out nested amplification reactions, such as a first primer extension reaction followed by a polymerase chain reaction on a target polynucleotide encompassing a locus of interest. An "inside primer" is "nested" with respect to an "outside primer" for a locus of interest means that the inside primer and outside primer hybridize specifically to the same strand of the target polynucleotide, and the hybridization site of the outside primer is farther away from the locus of interest than the hybridization site of the inside primer. A "set of outside primer and inside primer" refers to one or more inside primers that are nested with respect to the outside primer(s) for a locus of interest. See FIG. 1 or FIG. 2 for example.

An "adaptor" used herein refers to an oligonucleotide that can be joined to a polynucleotide fragment.

The term "ligation" as used herein, with respect to two polynucleotides, such as an adaptor and a polynucleotide fragment, refers to the covalent attachment of two separate polynucleotides to produce a single larger polynucleotide with a contiguous backbone.

The term "denaturing" or "dissociating" as used interchangeably herein refers to the separation of a nucleic acid duplex into two single-strands.

A "primer extension" refers to a molecular reaction in which a nucleic acid polymerase adds one or more nucleotides to the 3' terminus of a primer that is hybridized to a target nucleotide sequence in a template-specific manner, i.e., wherein the daughter strand produced by the primer extension reaction is complementary to the target nucleotide sequence. Extension does not only refer to the first nucleotide added to the 3' terminus of a primer, but also includes any further extension of a polynucleotide formed by the extended primer. Multiple cycles of primer extension can lead to linear amplification of a target nucleotide sequence. A "primer extension duplex" refers to the duplex product of a primer extension reaction, including the template strand, and the daughter strand. A "single-stranded primer extension product" specifically refers to the daughter strand produced by a primer extension reaction.

"Amplification" as used herein, generally refers to the process of producing two or more copies of a desired sequence. Components of an amplification reaction may include, but are not limited to, for example, primers, a polynucleotide template, polymerase, nucleotides, dNTPs and the like.

"Polymerase chain reaction amplification" or "PCR amplification" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. PCR amplification results an exponential increase in the numbers of a target nucleotide sequence.

"Amplified product", "amplification product", or "amplicon" refers to oligonucleotides resulting from a PCR amplification reaction that are copies of a portion of a particular target template nucleic acid strand and/or its complementary sequence, which correspond in nucleotide sequence to the template nucleic acid sequence and/or its complementary sequence. An amplification product can further comprise sequences specific to the primers and which flank the sequence(s) of the target nucleic acid and/or its complement. An amplicon, as described herein will generally be double-stranded DNA, although reference can be made to individual strands thereof.

A "reaction mixture" is an assemblage of components (e.g., one or more polypeptides, nucleic acids, and/or primers), which, under suitable conditions, react to carry out a specific reaction, e.g. a primer extension reaction or a PCR amplification reaction.

The term "enrichment" refers to the process of increasing the relative abundance of particular nucleic acid sequences in a sample relative to the level of nucleic acid sequences as a whole initially present in said sample before treatment. Thus the enrichment step provides a relative percentage or fractional increase, rather than directly increasing, for example, the absolute copy number of the nucleic acid sequences of interest. After the step of enrichment, the sample to be analyzed may be referred to as an enriched, or selected polynucleotide.

As used herein, the term "library" refers to a collection of nucleic acid sequences.

The term "determining," "detecting," "measuring," "evaluating," "assessing," "assaying," and "analyzing" are used interchangeably herein to refer to any form of measurement, and include determining if an element is present or not. These terms include both quantitative and/or qualitative determinations.

"Sequence variant" as used interchangeably herein, refers to any sequence alteration in a sequence of interest in comparison to a reference sequence. A reference sequence can be a wild type sequence or a sequence to which one wishes to compare a sequence of interest. Sequence variants include, but are not limited to, chromosomal rearrangement, copy number variant (CNV), insertion, deletion, splice variant, and single nucleotide mutations. A sequence variant includes single nucleotide changes, or alterations of more than one nucleotide in a sequence, due to mechanisms such as substitution, deletion, insertion, structural rearrangement, and genetic engineering.

As used herein, the term "single nucleotide variant," or "SNV" for short, refers to the alteration of a single nucleotide at a specific position in a genomic sequence. When alternative alleles occur in a population at appreciable frequency (e.g., at least 1% in a population), a SNV is also known as "single nucleotide polymorphism" or "SNP".

It is understood that aspect and embodiments of the invention described herein include "consisting" and/or "consisting essentially of" aspects and embodiments.

As used herein, the singular form "a", "an", and "the" includes plural references unless indicated otherwise.

As is understood by one skilled in the art, reference to "about" a value or parameter herein includes (and describes) embodiments that are directed to that value or parameter per se. For example, description referring to "about X" includes description of "X".

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); and Davis et al., Basic Methods in Molecular Biology, Elsevier Science Publishing, Inc., New York, USA (1995) which are all incorporated by reference herein in their entireties.

II. Methods of Target Enrichment

One aspect of the present application relates to methods of target enrichment for next-generation sequencing, i.e., methods of enriching target nucleotide sequences having one or more loci of interest prior to determining the target nucleotide sequences using a next-generation sequencing technology.

In some embodiments, there is provided a method of enriching a target nucleotide sequence having a locus of interest from a nucleic acid sample comprising a nucleic acid template comprising the target nucleotide sequence (e.g., for next-generation sequencing), the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the target nucleotide sequence (e.g., the plus strand sequence or the minus strand sequence); (c) annealing an outside primer to the first strand of the ligated nucleic acid in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) optionally repeating steps (c)-(e) for one or more primer extension cycles; (g) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; and (h) repeating step (g) for one or more cycles of PCR amplification to provide amplicons of the target nucleotide sequence, thereby enriching the target nucleotide sequence. In some embodiments, steps (c)-(e) are repeated for one or more cycles. In some embodiments, steps (c)-(e) are not repeated.

In some embodiments, a plurality of sets of outside primer and inside primer are used to enrich a target nucleotide sequence having a locus of interest. As used herein, a "target nucleotide sequence" generally refers to the sequence of a duplex target polynucleotide, which can refer to either the plus strand sequence or the minus strand sequence. In some embodiments, the method comprises enriching a target nucleotide sequence having the locus of interest using a first set of outside primer and inside primer that specifically anneal to the first strand of the ligated nucleic acid, and a second set of outside primer and inside primer that specifically anneal to the second strand of the ligated nucleic acid. In some embodiments, the outside primer of the first set and the outside primer of the second set comprises a first 5' tag sequence of at least 13 nucleotides long (such as at least about any one of 15, 20, 25 or more nucleotides long) and the inside primer of the first set and the inside primer of the second set comprises a second 5' tag sequence of at least 13 nucleotides long (such as at least about any one of 15, 20, 25 or more nucleotides long). The 5' tag sequence in the outside primers can suppress formation of PCR amplification products and primer dimers, thereby resulting in linear amplification (or primer extension). In some embodiments, a plurality of sets of outside primer and inside primers, either in one direction or in both directions with respect to the target nucleotide sequence is used to provide amplicons tiling a locus of interest.

Thus, in some embodiments, there is provided a method of enriching a target nucleotide sequence having a locus of interest from a nucleic acid sample comprising a nucleic acid template comprising the target nucleotide sequence (e.g., for next-generation sequencing), the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the plus strand sequence of the target nucleotide sequence and the second strand comprises the minus strand sequence of the target nucleotide sequence; (c) annealing a first outside primer to the first strand of the ligated nucleic acid in the vicinity of the plus strand sequence of the target nucleotide sequence, and annealing a second outside primer to the second strand of the ligated nucleic acid in the vicinity of the minus strand sequence of the target nucleotide sequence; (d) extending the first outside primer over the full length of the first strand of the ligated nucleic acid, and the second outside primer over the full length of the second strand of the ligated nucleic acid using a DNA polymerase to provide nascent primer extension duplexes; (e) dissociating the nascent primer extension duplexes at a sufficiently high temperature into the first strand of the ligated nucleic acid and a first single-stranded primer extension product, and the second strand of the nucleic acid and a second single-stranded primer extension product; (f) repeating steps (c)-(e) for one or more primer extension cycles; (g) contacting the first single-stranded primer extension products and the second single-stranded primer extension products with a DNA polymerase, a universal adaptor primer, a first inside primer, and a second inside primer under a condition sufficient for PCR amplification of the target nucleotide sequence and the complementary target nucleotide sequence, wherein the universal adaptor primer anneals to a complementary sequence of the non-duplex portion of the universal adaptor in the first single-stranded primer extension products and the second single-stranded primer extension products, wherein the first inside primer comprises a sequence at the 3' end that specifically anneals to the plus strand sequence of the target nucleotide sequence, wherein the second inside primer comprises a sequence at the 3' end that specifically anneals to the minus strand sequence of the target nucleotide sequence, wherein the first inside primer is nested with respect to the first outside primer for the locus of interest, and wherein the second inside primer is nested with respect to the second outside primer for the locus of interest; and (h) repeating step (g) for one or more cycles of PCR amplification to provide amplicons of the plus strand sequence and the minus strand sequence of the target nucleotide sequence, thereby enriching the target nucleotide sequence. In some embodiments, the outside primer of the first set and the outside primer of the second set comprises a first 5' tag sequence of at least 13 nucleotides long and the inside primer of the first set and the inside primer of the second set comprises a second 5' tag sequence of at least 13 nucleotides long.

In some embodiments, the method incorporates sequences compatible with sequencing primers specific to a NGS platform during the target enrichment steps. In some embodiments, the non-duplex portion of the universal adaptor comprises a sequence identical or complementary to the sequence of a first sequencing primer of an NGS platform. In some embodiments, the universal adaptor primer comprises at the 5' end a sequence identical or complementary to the sequence of a first sequencing primer of an NGS platform. In some embodiments, the inside primer comprises at the 5' end a sequence identical or complementary to the sequence of a second sequencing primer of an NGS platform. In some embodiments, step (g), i.e., the PCR amplification step, comprises contacting the single-stranded primer extension products with a DNA polymerase, a universal adaptor primer, an inside primer, and a sequencing adaptor primer under a condition sufficient for PCR amplification of the target nucleotide sequence, wherein the sequencing adaptor primer comprises at the 3' end a sequence identical to a sequence of the inside primer, and at the 5' end a sequence identical or complementary to the sequence of a second sequencing primer. In some embodiments, the sequencing adaptor primer comprises a sample barcode. In some embodiments, the universal adaptor primer comprises a sample barcode having identical or complementary sequence as the sample barcode of the sequencing adaptor primer.

Thus, in some embodiments, there is provided a method of enriching a target nucleotide sequence having a locus of interest from a nucleic acid sample comprising a nucleic acid template comprising the target nucleotide sequence (e.g., for next-generation sequencing), the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the target nucleotide sequence (e.g., the plus strand sequence or the minus strand sequence); (c) annealing an outside primer to the first strand in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) repeating steps (c)-(e) for one or more (such as about 2-100, e.g., about 5-50, or about 10-30) primer extension cycles; (g) contacting the single-stranded primer extension products with a DNA polymerase, a universal adaptor primer, an inside primer, and a sequencing adaptor primer, under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, wherein the inside primer is nested with respect to the outside primer for the locus of interest, wherein the universal adaptor (e.g., the non-duplex portion or the duplex portion) and/or the 5' end of the universal adaptor primer comprises a sequence identical or complementary to the sequence of a first sequencing primer of an NGS platform, wherein the sequencing adaptor primer comprises at the 3' end a sequence identical to a sequence of the inside primer, and at the 5' end a sequence identical or complementary to the sequence of a second sequencing primer of the NGS platform; and (h) repeating step (g) for one or more (such as about 2-100, e.g., about 5-50, or about 10-30) cycles of PCR amplification to provide amplicons of the target nucleotide sequence, thereby enriching the target nucleotide sequence. In some embodiments, the method comprises enriching a target nucleotide sequence having the locus of interest using a first set of outside primer and inside primer that specifically anneal to the first strand of the ligated nucleic acid, and a second set of outside primer and inside primer that specifically anneal to the second strand of the ligated nucleic acid. In some embodiments, the outside primer of the first set and the outside primer of the second set comprises a first 5' tag sequence of at least 13 nucleotides long and the inside primer of the first set and the inside primer of the second set comprises a second 5' tag sequence of at least 13 nucleotides long.

The methods described herein can be used to enrich a target nucleotide sequence having a locus of interest from a nucleic acid sample comprising any number of nucleic acid templates comprising the target nucleotide sequence, including, for example, at least about any one of 2, 5, 10, 20, 50, 100, 200, 500, 1000, 2000, 5000, 10000 or more nucleic acid templates comprising the target nucleotide sequence. The methods described herein can also be multiplexed. The term "multiplex" as applied to the methods described herein means that a plurality of sets of outside and inside primers is used to specifically enrich target nucleotide sequences having at least two different loci of interest in the same reaction. In some embodiments, the plurality of sets of outside and inside primers are present in a single reaction mixture, e.g. a plurality of different amplicons can be produced in the same reaction mixture. In some embodiments, at least 2 of the plurality of target nucleotide sequences are present in different strands of the nucleic acid template.

In some embodiments, target nucleotide sequences having a plurality of different loci of interest, such as at least about any one of 2, 5, 10, 20, 50, 100, 200, 500, 1000, 1500, 2000, 5000 or more loci of interest, are enriched. In some embodiments, target sequences having about 2-5000 (e.g., about any one of 2-100, 5-200, 100-2000, 2-2000, 101-5000, or 1500-5000) different loci of interest are enriched in a single reaction.

Thus, in some embodiments, there is provided a method of enriching target nucleotide sequences having a plurality (such as at least about 1000, 1500, 2000, or more) of different loci of interest from a nucleic acid sample comprising nucleic acid templates comprising the target nucleotide sequences (e.g., for next-generation sequencing), comprising: (a) ligating a universal adaptor to the nucleic acid templates to provide ligated nucleic acids, wherein the universal adaptor is an oligonucleotide comprising a duplex portion at a first end and a non-duplex portion at a second end, and wherein each nucleic acid template is ligated to the universal adaptor via the first end; (b) dissociating each ligated nucleic acid into a first strand and a second strand, wherein the first strand comprises a target nucleotide sequence (e.g., the plus strand sequence or the minus strand sequence); (c) annealing an outside primer to the first strand in the vicinity of each target nucleotide sequence; (d) extending the outside primers over the full lengths of the first strands using a DNA polymerase to provide nascent primer extension duplexes; (e) dissociating the nascent primer extension duplexes at a sufficiently high temperature into the first strands and single-stranded primer extension products; (f) repeating steps (c)-(e) for one or more (such as about 2-100, e.g., about 5-50, or about 10-30) primer extension cycles; (g) contacting the single-stranded primer extension products with a DNA polymerase, a universal adaptor primer and inside primers under a condition sufficient for PCR amplification of the target nucleotide sequences, wherein the universal adaptor primer anneals to a complementary sequence of the non-duplex portion of the universal adaptor in the single-stranded primer extension products, wherein each inside primer comprises a sequence at the 3' end that specifically anneals to a target nucleotide sequence, and wherein an inside primer is nested with respect to an outside primer for each locus of interest; and (h) repeating step (g) for one or more (such as about 2-100, e.g., about 5-50, or about 10-30) cycles of PCR amplification to provide amplicons of the target nucleotide sequences, thereby enriching the target nucleotide sequences. In some embodiments, the method comprises enriching a target nucleotide sequence having the locus of interest using a first set of outside primer and inside primer that can specifically anneal to the first strand of the ligated nucleic acid, and a second set of outside primer and inside primer that can specifically anneal to the second strand of the ligated nucleic acid. In some embodiments, the outside primer of the first set and the outside primer of the second set comprises a first 5' tag sequence of at least 13 nucleotides long and the inside primer of the first set and the inside primer of the second set comprises a second 5' tag sequence of at least 13 nucleotides long. In some embodiments, the universal adaptor or the 5' end of the universal adaptor primer comprises a sequence identical or complementary to the sequence of a first sequencing primer of an NGS platform. In some embodiments, the inside primer comprises at the 3' end a sequence that specifically anneals to the target nucleotide sequence, and at the 5' end a sequence identical or complementary to the sequence of a second sequencing primer of the NGS platform. In some embodiments, step (g) comprises contacting the single-stranded primer extension products with a DNA polymerase, a universal adaptor primer, an inside primer, and a sequencing adaptor primer under a condition sufficient for PCR amplification of the target nucleotide sequence.

In some embodiments, the method has high sensitivity, such as at least about any one of 70%, 80%, 90%, 95%, or higher of the target nucleotide sequences are represented by one or more sequence reads. In some embodiments, the method has high specificity, such as at least about any one of 70%, 80%, 85%, 90%, 95%, 98% or more of the read sequences map to the intended target nucleotide sequences. In some embodiments, the method has high uniformity. In some embodiments, the method has high reproducibility. In some embodiments, the method requires a low amount of input nucleic acid sample, such as no more than about any one of 50 ng, 25 ng, 10 ng, 5 ng, 1 ng of nucleic acids or less.

Figure 2:
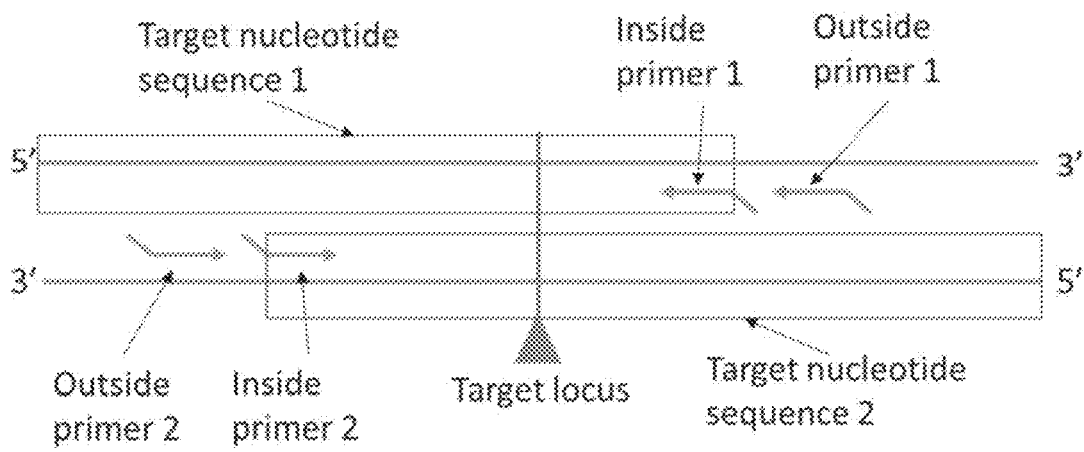
FIG. 2 shows two exemplary sets of outside primers and inside primers for enrichment of target nucleotide sequences on both strands of a nucleic acid template having a target locus.

FIG. 1 shows a schematic of an exemplary method of enriching target nucleotide sequences having a locus of interest. In this non-limiting example, a nucleic acid template comprising the target nucleotide sequence is first ligated to the universal adaptor, one copy on each end of the nucleic acid template. In a first primer extension cycle, the outside primer specially anneals to a first strand of the ligated nucleic acid. Depending upon the orientation with which the outside primer is designed, sequence upstream or downstream of the annealing site, on the plus and/or minus strand is synthesized. Pools of outside primers can also be used to provide tiling primer extension products. The nascent single-stranded primer extension product has on the 3' end the full-length sequence complementary to one strand of the universal adaptor. In each subsequent primer extension cycle, the original ligated nucleic acid strands continue to serve as the templates for the primer extension, resulting in linear amplification of the single-stranded primer extension products. Outside primers in the opposite direction each comprises an identical 5' tag sequence, which suppresses PCR amplification products and promotes linear amplification of the ligated nucleic acid. In the subsequent PCR amplification cycles, the universal adaptor primer and the inside primer specifically anneal to appropriate strands of the primer extension products or PCR amplicons thereof, thereby providing exponential amplification of the target nucleotide sequences. Inside primers in the opposite direction each comprises an identical 5' tag sequence, which suppresses primer dimer and undesirable side products. The PCR amplification cycles may further involve a sequencing adaptor primer having a sequence identical or complementary to a sequencing primer. For pair-end sequencing, the universal adaptor or universal adaptor primer can have a 5' portion having a sequence identical or complementary to a reverse sequencing primer. A sequencing library comprising amplicons of the target nucleotide sequences ready for NGS sequencing is thereby obtained.

The amplicons of the target nucleotide sequence prepared by the methods described herein can be analyzed using a variety of methods, including, but not limited to, nucleic acid sequencing (e.g., Sanger sequencing or Next-generation sequencing, also referred herein as "NGS"), microarray analysis, quantitative PCR, and digital PCR.

Ligation

The methods described herein comprise, as a first step, ligation of a universal adaptor to one or more nucleic acid templates in the nucleic acid sample. In some embodiments, the nucleic acid sample comprises nucleic acid templates that comprise both target nucleotide sequences and non-target nucleotide sequences. In some embodiments, the universal adaptor is ligated to substantially all of the nucleic acid templates in the nucleic acid sample. In some embodiments, the universal adaptor is ligated to both target nucleic acid templates that comprise the target nucleotide sequences, and non-target nucleic acid templates that do not comprise the target nucleotide sequences.

Ligation of the universal adaptor to the nucleic acid templates can be accomplished by any method known in the art, e.g., blunt-end ligation or TA ligation. In some embodiments, prior to ligation of the universal adaptor, the nucleic acid templates in a sample is subjected to nucleic acid end-repair to blunt the ends of the nucleic acid templates. End-repair is well known in the art and relevant kits and/or enzymes are available commercially, (e.g., the NEB-NEXT™ End Repair Module, New England Biolabs; Ipswich, Mass.).

In some embodiments, prior to ligation of the universal adaptor, the nucleic acid templates in a sample, the nucleic acid templates in a sample can be phosphorylated and/or adenylated. Adenylation can provide an adenosine overhang on the 3' end of a nucleic acid template. A second nucleic acid with a 3' thymidine (T) overhang can then be ligated to the first nucleic acid by TA ligation. Methods of TA ligation are well known in the art and relevant kits and/or enzymes are available commercially, e.g. the NEBNEXT™ dA-Tailing module (New England Biolabs; Ipswich, Mass.) can be used to adenylate a blunt end of a nucleic acid. In some embodiments, the universal adaptor comprises a 3' T overhang.

Primer Extension

The ligated nucleic acids are subjected to one or more primer extension cycles or linear amplification cycles using the outside primer. The primer extension cycles can increase the abundance of the target nucleotide sequences linearly, as the nucleic acid template comprising the target nucleotide sequence serves as template in each primer extension cycle. In some embodiments, the primer extension cycles are repeated for one or more times. In some embodiments, the primer extension cycle is not repeated. In some embodiments, the method comprises at least 2 or more primer extension cycles, such as at least about any one of 5, 10, 15, 20, 25, 30 or more iterative primer extension cycles. In some embodiments, the method comprises about 2-100 primer extension cycles, e.g., any one of about 5-50, about 5-30, about 5-20, about 10-20, about, about 10-15, about 15-30, about 30-50, or about 10-30 primer extension cycles. Each primer extension cycle comprises the steps of: 1) strand separation (e.g., thermal denaturation) 2) annealing of the outside primer to the first strand of a ligated nucleic acid comprising the target nucleotide sequence; and 3) nucleic acid polymerase extension of the annealed primer. Conditions and times necessary for each of these steps can be devised by one of ordinary skill in the art. The primer extension cycles can be performed in a thermal cycler, many of which are commercially available.

Each primer extension cycle comprises a strand dissociation or separation step generally involving heating of the reaction mixture. As used herein, "strand separation", "strand dissociation", or "melting" means treatment of a nucleic acid sample such that complementary double-stranded molecules are separated into two single strands available for annealing to an oligonucleotide primer. In some embodiments, dissociating the duplex primer extension products is achieved by heating the primer extension reaction mixture at a sufficiently high temperature. In some embodiments, the sufficiently high temperature is above the melting temperature (Tm) of the primer extension strands. In some embodiments, the sufficiently high temperature is at least about 90° C., such as at least about any one of 91° C., 92° C., 93° C., 94° C., 95° C., 96° C. or 97° C. In some embodiments, the sufficiently high temperature is about 90° C. to about 97° C. In some embodiments, the duplex primer extension products are dissociated in the presence of agents capable of raising or lowering the denaturation temperature of the duplex primer extension products. Exemplary agents that can raise or lower the denaturation temperature of the duplex primer extension products include, but are not limited to, salts, and dimethyl sulfoxide.

In some embodiments, conditions for annealing between the outside primer and the first strand of the ligated nucleic acid may vary based on the length and sequence of the primer. In some embodiments, conditions for annealing are based upon a Tm (e.g., a calculated Tm) of the outside primer. In some embodiments, an annealing step of a primer extension cycle involves reducing the temperature following strand separation step to a temperature based on the Tm (e.g., a calculated Tm) for the outside primer, for a time sufficient to permit such annealing.

In some embodiments, the time allowed for primer annealing during a primer extension cycle depends upon the volume of the reaction, with larger volumes requiring longer times, but also depends upon primer and template concentrations, with higher relative concentrations of primer to template requiring less time than lower relative concentrations. In some embodiments, the primer extension cycle comprises gradual heating to a sufficiently high temperature (e.g., 90° C.-95° C.) to dissociate duplex nucleic acids, followed by gradual cooling to the temperature for primer extension (e.g., 60° C.) prior to primer extension. In some embodiments, the primer extension reaction is heated or cooled gradually with consecutive temperature differences of no more than about any of 1° C./sec, 0.8° C./sec, 0.7° C./sec, 0.6° C./sec, 0.5° C./sec, 0.4° C./sec, 0.3° C./sec, 0.2° C./sec, 0.1° C./sec or less.

The polymerase extension step requires the use of a nucleic acid polymerase that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. In some embodiments, the nucleic acid polymerase is thermostable, i.e., it retains function after being subjected to temperatures sufficient to denature annealed strands of complementary nucleic acids, e.g. 94° C., or higher. In some embodiments, the nucleic acid polymerase is a DNA polymerase.

Numerous nucleic acid polymerases are known in the art and commercially available. In some embodiments, the nucleic acid polymerase is DNA polymerase I, Taq polymerase, PheonixTaq polymerase, PHUSION® polymerase, T4 polymerase, T7 polymerase, Klenow fragment, Klenowexo-, phi29 polymerase, AMV reverse transcriptase, M-MuLV reverse transcriptase, HIV-1 reverse transcriptase, VERASEQ™ ULtra polymerase, VERASEQ™ HF 2.0 polymerase, ENZSCRIPT™ or another appropriate polymerase. In some embodiments, a nucleic acid polymerase is not a reverse transcriptase. In some embodiments, a nucleic acid polymerase acts on a DNA template. In some embodiments, a Taq DNA polymerase (e.g., PLATINUM™ Taq) is used in the primer extension cycles.

In some embodiments, the nucleic acid template is an RNA template, and a nucleic acid polymerase acting on an RNA template is used in the primer extension cycles instead or in addition to a DNA polymerase. In some embodiments, an extension reaction involves reverse transcription performed on a RNA to produce a complementary DNA molecule ("RNA-dependent DNA polymerase activity"). In some embodiments, a reverse transcriptase is a mouse molony murine leukemia virus polymerase, AMV reverse transcriptase, RSV reverse transcriptase, HIV-1 reverse transcriptase, HIV-2 reverse transcriptase or another appropriate reverse transcriptase.

In some embodiments, polymerase extension is performed under conditions that permit the extension of annealed oligonucleotide printers. As used herein, the term "polymerase extension" means the template-dependent incorporation of at least one complementary nucleotide, by a nucleic acid polymerase, onto the 3' end of an annealed primer. Polymerase extension preferably adds more than one nucleotide, preferably up to and including nucleotides corresponding to the full length of the template. The conditions include, for example, suitable temperature, salt and co-factor concentrations, pH, and enzyme concentrations. In some embodiments, such conditions are based, at least in part, on the nucleic acid polymerase being used. In some embodiments, a polymerase may perform a primer extension reaction in a suitable reaction preparation. In some embodiments, a suitable reaction preparation contains one or more salts (e.g., 1 to 100 mM KCl, 0.1 to 10 mM $MgCl_2$), at least one buffering agent (e.g., 1 to 20 mM Tris-HCL), and a carrier (e.g., 0.01 to 0.5% BSA) and one or more nucleotide triphosphates (e.g., 10 to 200 µM of each of dATP, dTTP, dCTP, and dGTP). The temperature used for polymerase extension is generally based upon the known activity properties of the enzyme. Although, where annealing temperatures are required to be, for example, below the optimal temperatures for the enzyme, it will often be acceptable to use a lower extension temperature. In general, although the enzymes retain at least partial activity below their optimal extension temperatures, polymerase extension by the most commonly used thermostable polymerases Taq polymerase and variants thereof) is performed at 60° C. to 75° C. A non-limiting set of conditions include 50 mM KCl, 10 mM Tris-HCl (pH 8.8 at 25° C.), 0.5 to 3 mM $MgCl_2$, 200 µM of each dNTP, and 0.1% BSA at 60° C., under which a polymerase (e.g., PLATINUM™ Taq polymerase) catalyzes primer extension.

The polymerase extension step of the primer extension cycle can last a sufficient amount of time to allow primer extension over the entire length of the first strand of the ligated nucleic acid, e.g., to reach the 5'-end of the first strand of the universal adaptor. The sufficient amount of time for the polymerase extension step can be determined based on the average length of the ligated nucleic acids, and the speed of the polymerase. In some embodiments, the length of the polymerase extension step is at least about any one of 2 minutes, 4 minutes, 6 minutes, 8 minutes, 10 minutes, 15 minutes or more.

A non-limiting example of a protocol for primer extension using a Taq polymerase (e.g., PLATINUM™ Taq) can be carried out under the following conditions: 95° C. for 5 minutes; followed by 10-30 cycles of ramping up to 95° C. at a speed of +0.2° C./sec, melting at 95° C. for 10 sec, ramping down to 60° C. at a speed of −0.2° C./sec for annealing, and extension at 60° C. for 10 minutes; followed by holding of the reaction at 4° C. However, other appropriate reaction conditions may be used. In some embodiments, annealing/extension temperatures may be adjusted to account for differences in salt concentration (e.g., 3° C. higher to higher salt concentrations).

PCR Amplification

The single-stranded primer extension products are subjected to one or more of polymerase chain reaction (PCR) amplification cycles using the universal adaptor primer and the inside primers, and optionally the sequencing adaptor primer. The PCR amplification cycles can increase the abundance of the target nucleotide sequences exponentially, as the products of a previous polymerase extension serve as templates for the successive rounds of extension. In some embodiments, the method comprises at least 2 or more PCR amplification cycles, such as at least about any one of 5, 10, 15, 20, 25, 30 or more iterative PCR amplification cycles. In some embodiments, the method comprises about 2-100 PCR amplification cycles, e.g., any one of any one of about 5-50, about 5-30, about 5-20, about 10-20, about, about 10-15, about 15-30, about 30-50, or about 10-30 PCR amplification cycles. Each PCR amplification cycle comprises the steps of: 1) strand separation (e.g., thermal denaturation) 2) annealing of the universal adaptor primer and inside primer to template molecules; and 3) nucleic acid polymerase extension of the annealed primers. Conditions and times necessary for each of these steps can be devised by one of ordinary skill in the art. The PCR amplification cycles can be performed in a thermal cycler, many of which are commercially available.

The conditions (such as enzyme, salt, buffer, temperature, etc.) used for each step of the PCR amplification cycle may be the same or substantially similar to those in the corresponding steps in the primer extension cycle. Any one of the nucleic acid polymerases, buffer conditions, strand dissociation temperature, and polymerase extension time as described in the "Primer extension" section can be used for the PCR amplification cycles. In some embodiments, the nucleic acid polymerase used in the PCR amplification cycles is the same as that used in the primer extension cycles. In some embodiments, the nucleic acid polymerase used in the PCR amplification cycles is different from that used in the primer extension cycles. In some embodiments, the nucleic acid polymerase is a DNA polymerase. In some embodiments, a Taq polymerase (e.g., PLATINUM™ Taq) is used in the PCR amplification cycles. In some embodiments, the extension time of the PCR amplification cycles is the same as that in the primer extension cycles. In some embodiments, the extension time of the PCR amplification cycles is different from that in the primer extension cycles.

A non-limiting example of a protocol for amplification involves using a polymerase (e.g., PLATINUM™ Taq polymerase) under the following conditions: 95° C. for 5 minutes, following by 10-25 cycles comprising melting at 95° C. for 30 s, followed by annealing and extension at 60° C. for 5 minutes, followed by holding of the reaction at 4° C. However, other appropriate reaction conditions may be used. In some embodiments, annealing/extension temperatures may be adjusted to account for differences in salt concentration (e.g., 3° C. higher to higher salt concentrations).

Additional Steps

The methods described herein may comprise additional steps, including, but not limited to fragmentation, enzyme digestion, and/or cleanup steps.

Many of the NGS sequencing methods suitable for use in the methods described herein provide sequencing runs with optimal read lengths of tens to hundreds of nucleotide bases (e.g. ION TORRENT™ technology can produce read lengths of 200-400 bp). For example, if the optimal read-length of a given sequencing technology is 200 bp, the amplicons of the target nucleotide sequences from the methods described herein may have an average length of no more than about any one of 800 bp, 700 bp, 600 bp, 500 bp, 400 bp, 300 bp, about 200 bp or less. In some embodiments, the universal adaptor, the outside and inside primers, and/or the universal adaptor primer are designed to provide amplicons of a suitable length for use in a particular sequencing technology. In some embodiments, the method comprises fragmenting the nucleic acid templates prior to the ligation step, or fragmenting the primer extension products or the amplicons of target nucleotide sequences. "Fragmenting" a polynucleotide used herein refers to breaking the polynucleotides into different polynucleotide fragments. Fragmenting can be achieved, for example, by shearing or by enzymatic reactions. In some embodiments, the nucleic acid templates are fragmented to a size suitable for the next-generation sequencing.

In some embodiments, the nucleic acid templates or nucleic acid products from the steps in the methods described herein (e.g., primer extension, PCR amplification, or prior to sequencing) are sheared, e.g. mechanically or enzymatically sheared, to generate fragments of any desired size. In some embodiments, the nucleic acid templates are mechanically sheared by sonication. In some embodiments, the nucleic acid templates are not sheared or enzymatically digested. In some embodiments, nucleic acid products from the steps in the methods described herein (e.g., primer extension, PCR amplification, or prior to sequencing) are not sheared or enzymatically digested. In some embodiments, the nucleic acid templates are fragmented to an average size of no more than about any one of 1 kb, 800 bp, 700 bp, 600 bp, 500 bp, 400 bp, 300 bp, about 200 bp or less.

Full-length or long fragments of genomic DNA (such as a chromosome), mRNA, and cDNA can be sheared, e.g. mechanically or enzymatically sheared, to generate fragments of any desired size prior to the ligation step. Non-limiting examples of mechanical shearing processes include sonication, nebulization, and AFA™ shearing technology available from Covaris (Woburn, Mass.). In some embodiments, a genomic DNA is mechanically sheared by sonication to nucleic acid templates of suitable length. In some embodiments, when the nucleic acid templates are cDNA derived from RNA, the RNA sample can be subjected to reverse transcription to generate cDNA, and the cDNA template can then be sheared. In some embodiments, the RNA can be sheared before performing a reverse transcription.

In some embodiments, the method comprises one or more cleanup steps to remove unreacted adaptors and primers, polymerase, and nucleotides after the ligation step, the primer extension cycles, and/or the PCR amplification cycles. In some embodiments, the ligated nucleic acids are subjected to a cleanup procedure prior to the primer extension cycles, such as step (b). In some embodiments, the primer extension products are subjected to a cleanup procedure prior to the PCR amplification cycles, such as step (g). Nucleic acid cleanup procedures are known in the art, and kits for cleaning up primer extension products and PCR amplification products are commercially available, for example, AMPURE® beads by Beckman Coulter.

In some embodiments, the method further comprises any one or more steps for obtaining, processing, or preparing the biological sample, and/or the nucleic acid sample described in the section "Nucleic acid sample".

Primers and Adaptors

Oligonucleotide adaptors and primers are used in the methods described herein, including the universal adaptor, the nested target-specific primers (i.e., outside primer and inside primer), the universal adaptor primer, and the sequencing adaptor primer, and sequencing primers suitable for specific NGS platforms. The primers and adaptors described herein can be specially designed and optimized for high specificity, sensitivity, efficiency (e.g., ligation, primer extension, PCR amplification, or NGS sequencing), and/or low bias towards certain types of sequences such as sequences with high GC contents.

The primers described herein are designed to anneal specifically to a known nucleotide sequences in a template nucleic acid. In some embodiments, the primer comprises a sequence complementary or substantially complementary to the strand in the template nucleic acid it specifically anneals to. In some embodiments, the sequence in the primer that hybridizes to the template nucleic acid is at the 3' end of the sequence.

The primers used herein are generally single-stranded, and a primer and its complement can anneal to form a double-stranded polynucleotide. In some embodiments, the primers are no more than about 300 nucleotides in length, e.g., no more than about any one of 300, 250, 200, 150, 100, 90, 80, 70, 60, 50, 40, 30, 20, 15 or fewer nucleotides in length, but at least about 10 nucleotides in length.

In some embodiments, primers disclosed herein (e.g., outside and inside primers, universal adaptor primer, and/or sequencing adaptor primer) are designed such that they can specifically anneal to their complementary sequences at an annealing temperature of any one of about 55-72° C., 60-72° C., about 60-70° C., about 62-69° C., about 63-67° C., or about 64-66° C. In some embodiments, primers disclosed herein are designed such that they can specifically anneal to their complementary sequences at an annealing temperature of less than about any one of 72° C., 70° C., 68° C., 65° C. or 60° C. The annealing temperature, also known as melting temperature or Tm, of a primer can be determined using any of a number of algorithms (e.g., OLIGO™ (Molecular Biology Insights Inc. Colorado) primer design software and VENTRO NTI™ (Invitrogen, Inc. California) primer design software and programs available on the internet, including Primer3, Oligo Calculator, and NetPrimer (Premier Biosoft; Palo Alto, Calif.). In some embodiments, the Tm of a primer can be calculated using following formula: $Tm=AH/(AS+R*\ln(C/4))+16.6 \log([K+]/(1+0.7 [K+]))-273.15$, wherein ΔH is enthalpy for helix formation; ΔS is entropy for helix formation; R is molar gas constant (1.987 cal/° C.×mol); C is the nucleic acid concentration; and [K+] is salt concentration. See, Frieir et al. PNAS 1986 83:9373-9377.

Any one of more of the following design principles may be used to optimize the design of the primers. For example, for low coverage, hard to enrich target nucleotide sequences comprising high GC content sequences, the primers can be designed to cover adjacent sequences. A primer sequence can also be modified to reduce secondary structure of the primer and enhance its efficiency of hybridization. A primer length or length of the portion of the primer that hybridizes specifically to its template can be modified to equalize melting hybridization kinetics of different primers within the same category. Primers of different orientation for the same target region forward and reverse strand can be modified to have different binding efficiencies.

The adaptors and primers are used in each step of the method at a suitable concentration. In some embodiments, the ratio between the concentrations of any two or more of the universal adaptor, the outside primer, the inside primer, the universal adaptor primer, and optionally the sequencing adaptor primer are optimized. For example, in some embodiments, the concentration ratio between the universal adaptor and the outside primer is no more than about any one of 5000:1, 1000:1, 100:1, 50:1, 20:1, 10:1, 5:1, 4:1, 3:1, 2:1, 1:1 or less. In some embodiments, the concentration ratio between two different outside primers is any one of about 1:4 to about 4:1, about 1:3 to about 3:1, about 1:2 to about 2:1, about 2:3 to about 3:2, or about 1:1. In some embodiments, the concentration ratio between two different inside primers is any one of about 1:4 to about 4:1, about 1:3 to about 3:1, about 1:2 to about 2:1, about 2:3 to about 3:2, or about 1:1. For example, a higher concentration of inside and/or outside primers can be used for a relatively difficult-to-enrich target nucleotide sequences. In some embodiments, the concentration ratio between the universal adaptor primer and the inside primer is no more than about any one of 5000:1, 1000:1, 100:1, 50:1, 20:1, 10:1, 5:1, 4:1, 3:1, 2:1, 1:1 or less. In some embodiments, the concentration ratio between each outside primer and its corresponding inside primer is any one of about 1:4 to about 4:1, about 1:3 to about 3:1, about 1:2 to about 2:1, about 2:3 to about 3:2, or about 1:1. For example, the relative concentrations of the different sets of outside primers and inside primers can be adjusted to enhance or reduce coverage of target nucleotides having certain loci of interest.

In some embodiments, the enriched target nucleotide sequences are ready for use in NGS. In some embodiments of the methods of determining target nucleotide sequences, detecting sequence variants, and diagnosis described in sections III and IV below, the method comprises a sequencing step that relies upon the use of a first sequencing primer and a second sequencing primer. In some embodiments, the first and second sequencing primers are selected to be compatible with a next-generation sequencing method as described herein. In some embodiments, the first sequencing primer comprises the P5 sequence for ILLUMINA®-based sequencing technology, and the second sequencing primer comprises the P7 sequence for ILLUMINA®-based sequencing technology; or the second sequencing primer comprises the P5 sequence for ILLUMINA®-based sequencing technology, and the first sequencing primer comprises the P7 sequence for ILLUMINA®-based sequencing technology. In some embodiments, the first sequencing primer comprises the PI sequence compatible with ION TORRENT™ sequencing technology, and the second sequencing primer comprises the A sequence compatible with ION TORRENT™ sequencing technology; or the second sequencing primer comprises the A sequence compatible with ION TORRENT™ sequencing technology, and the first sequencing primer comprises the PI sequence compatible with ION TORRENT™ sequencing technology. The universal adaptor and/or the universal adaptor primer may comprise a sequence identical or complementary to the sequence of the first sequencing primer. The inside primer, and/or the sequencing adaptor primer may comprise a sequence identical or complementary to the sequence of the second sequencing primer. The direction of the sequences in the universal adaptor, the universal adaptor primer, the inside primer, and/or the sequencing adaptor primer with respect to the first or second sequencing primers may be selected by one of skill in the art to provide amplicons having such sequences in an appropriate direction for pair-end sequencing.

In some embodiments, the primers and/or adaptors do not comprise modified or non-naturally occurring nucleotides. In some embodiments, the primers and/or adaptors comprise modified or non-naturally occurring bases. In some embodiments, the primers and/or adaptors are modified with a label capable of providing a detectable signal, either directly or indirectly. Non-limiting examples of such labels include radioisotopes, fluorescent molecules, biotin, and others. In some embodiments, the primers and/or adaptors contain a biotin linker or other suitable linker (e.g., for conjugating the primer to a support). In some embodiments, the primers and/or adaptors contain nuclease cleavage sites such that allow cleavage with an appropriate enzyme. In other embodiments, the 5' end of a primer includes a sequence that is complementary with a nucleic acid bound to a bead or other support, e.g., a flow cell substrate. In some embodiments, the primers and/or adaptors comprise modified internucleoside linkages, such as phosphorothioate.

Any suitable methods may be used for synthesizing the adaptors and primers. In some embodiments, commercial sources offer oligonucleotide synthesis services suitable for providing primers for use in methods and compositions described herein, e.g. INVITROGEN™ Custom DNA Oligos; Life Technologies; Grand Island, N.Y. or custom DNA Oligos from IDT; Coralville, Iowa). In some embodiments, any one of the adaptors and primers can be prepared by ligating two or more portions of the adaptors and primers.

Universal Adaptor and Universal Adaptor Primer

A universal adaptor used herein is an oligonucleotide comprising a ligatable duplex portion at a first end and a non-duplex portion at a second end. In some embodiment, the universal adaptor has two separate strands, namely a first strand and a second strand. In some embodiments, the universal adaptor comprises a first strand and a second strand. The first strand of the universal adaptor refers to the strand whose 3' end is located at the first end (i.e., the ligatable end) of the universal adaptor. The second strand of the universal adaptor refers to the strand whose 5' end is located at the first end (i.e. the ligatable end) of the universal adaptor.

In some embodiments, the first strand comprises a 5' unpaired portion, a 3' paired portion, and a 3'T overhang. In some embodiments, the second strand has a 3' unpaired portion and a 5' paired portion. In some embodiments, the non-duplex portion of the universal adaptor is single-stranded, e.g., the 5' unpaired portion of the first strand. In some embodiments, the entirety of the second strand is paired. The paired portions of the first strand and the second strand are substantially complementary and form the first end comprising the ligatable duplex portion and a 3' T overhang, and the duplex portion is of sufficient length to remain in duplex form at the ligation temperature.

In some embodiments, the universal adaptor has a "Y" shape, i.e. the unpaired portion comprises portions of the first strand and the second strand. The unpaired portion of the second strand can be shorter than, longer than, or equal in length to the unpaired portion of the first strand. In some embodiments, the unpaired portion of the second strand can be shorter than the unpaired portion of the first strand. Y-shaped universal adaptors have the advantage that the unpaired portion of the second strand is not amplified in the PCR amplification steps.

In some embodiments, the second strand of the universal adaptor comprises a 3' unpaired portion which is not substantially complementary to the 5' unpaired portion of the first strand, and wherein the 3' unpaired portion of the second strand is not substantially complementary to or substantially identical to any of the other primers. In some embodiments, the second strand of the universal adaptor comprises a 3' unpaired portion which does not specifically anneal to the 5' unpaired portion of the first strand at the annealing temperature, and wherein the 3' unpaired portion of the second strand does not specifically anneal to any of the other primers or the complementary sequences thereof at the annealing temperature.

In some embodiments, the universal adaptor is a hairpin, wherein the non-duplex portion is a loop. In some embodiments, the unpaired 5' portion of the amplification strand and the unpaired 3' portion of the blocking strand are connected to each other. In some embodiments, the loop is cleaved by an enzyme prior to dissociation of the ligated nucleic acids into two separate strands prior to the primer extension steps.

Figure 3:
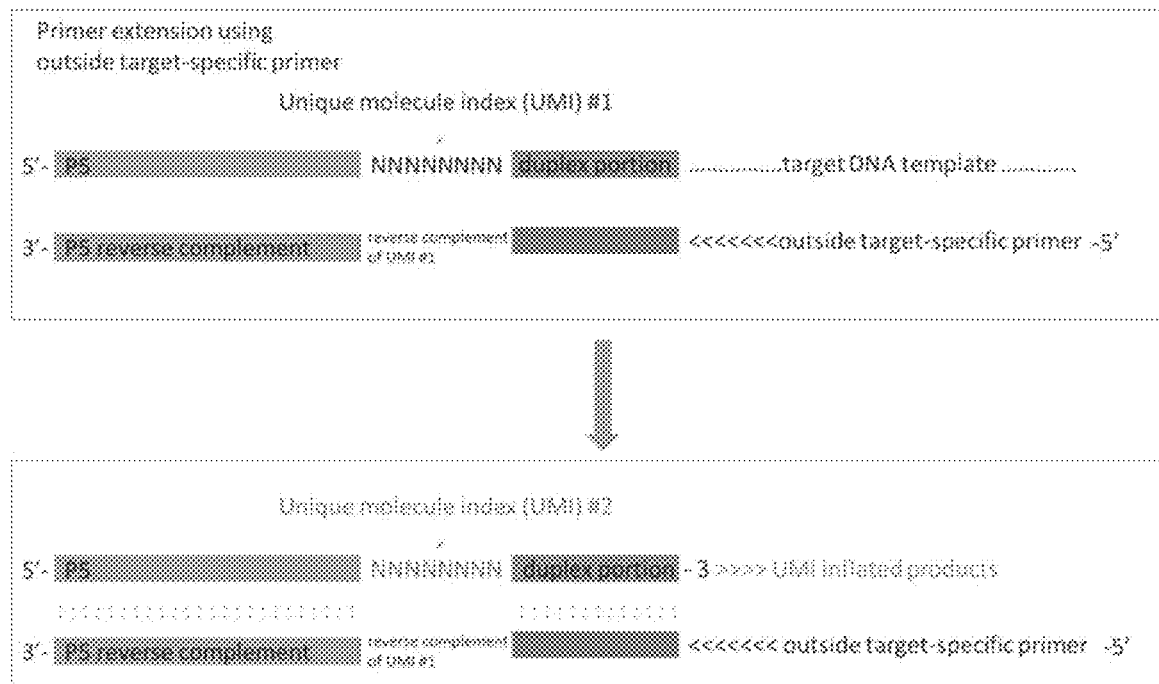
FIG. 3 shows potential side products due to carryover universal adaptor in the primer extension cycles.

In some embodiments, the duplex portion of the universal adaptor (e.g. the paired portions of either or both of the strands) is at least about 7 base pairs in length, e.g., at least about any one of 7 bp, 8 bp, 9 bp, 10 bp, 11 bp, 12 bp, 13 bp, 14 bp or more in length. In some embodiments, the duplex portion of the universal adaptor is no more than about 18 bp in length, e.g. no more than about any one of 17 bp, 16 bp, 15 bp, 14 bp, 13 bp, 12 bp or less in length. In some embodiments, the duplex portion of the universal adaptor is no more than about 14 bp in length. The duplex portion of the universal adaptor should not be so long as to suppress primer extension and/or PCR amplification of the desired amplicons. Additionally, the length of the duplex portion of the universal adaptor may be limited to reduce the inflated UMI complexity issue as illustrated in FIG. 3.

In some embodiments, the non-duplex portion of the universal adaptor comprises a sequence identical or complementary to the sequence of a first sequencing primer of an NGS platform. In some embodiments, the unpaired 5' portion of the first strand of the universal adaptor comprises a sequence identical or complementary to the sequence of a first sequencing primer of an NGS platform. In some embodiments, the first strand of the duplex portion of the universal adaptor comprises a sequence identical or complementary to the sequence of a first sequencing primer of an NGS platform.

In some embodiments, the universal adaptor comprises a barcode. In some embodiments, the duplex portion of the universal adaptor comprises a barcode. The use of barcodes in next-generation sequencing applications is well known in the art and described, for example, in Margulies, M. et al. "Genome Sequencing in Microfabricated. High-Density Picoliter Reactors", Nature, 437, 376-80 (2005); Mikkelsen, T. et al. "Genome-Wide Maps of Chromatin State in Pluripotent and Lineage-Committed. Cells", Nature, 448, 553-60 (200); McLaughlin, S. et al, "Whole-Genome Resequencing With Short Reads; Accurate Mutation Discovery With Mate Pairs and Quality Values", ASHG Annual Meeting (2007); Shendure I. et al. "Accurate Multiplex Polony Sequencing of an Evolved Bacterial Genome", Science, 309, 1728-32 (2005); Harris, T. et al. "Single-Molecule DNA Sequencing of a Viral Genome" Science, 320, 106-9 (2008); Simen, B. et al, "Prevalence of LOW Abundance Drug Resistant Variants by Ultra Deep Sequencing in Chronically HIV-infected Antiretroviral (ARV) Naive Patients and the impact on Virologic Outcomes", 16th International HIV Drug Resistance Workshop, Barbados (2007); Thomas, R. et al. "Sensitive Mutation Detection in Heterogeneous Cancer Specimens by Massively Parallel Picoliter Reactor Sequencing", Nature Med., 12, 852-855 (2006); Mitsuya, Y et al. "Minority Human Immunodeficiency Virus Type I Variants in Antiretroviral-Naive Persons With Reverse Transcriptase Codon 215 Revertant Mutations", I. Vir., 82, 10747-10755 (2008); Binladen, J. et al. "The Use of Coded PCR Primers Enables High-Throughput Sequencing of Multiple HomologAmplification Products by 454 Parallel Sequencing", PLoS ONE, 2, e197 (2007); and Hoffmann, C. et al. "DNA Bar Coding and Pyrosequencing to Identify Rare HIV Drug Resistance Mutations", Nuc. Acids Res., 35, e91 (2007), all of which are herein incorporated by reference.

In some embodiments, the universal adaptor comprises a molecular barcode comprising randomly and/or degenerately designed nucleobases. Molecular barcodes are also referred to as "Unique Molecule Index" or "UMI." In a composition comprising a plurality of universal adaptors comprising molecular barcodes, the molecular barcode in each universal barcode can be different because it contains nucleotide sequences comprising randomly designed (i.e., having any of the four nucleobases A, C, T, G) or degenerately designed (i.e., having one of a set of at least two types of nucleobases, for example, B=C/G/T; D=A/G/T; H=A/C/T; V=A/C/G; W=A/T; S=C/G; R=A/G; Y=C/T) nucleotides. The molecular barcode can thus be used for aligning sequencing reads of amplicons derived from the same nucleic acid template, thereby allowing correction of errors arising from the primer extension and/or PCR amplification cycles. The molecular barcode may further comprise nucleotides having the same identity for all universal adaptors in a composition (i.e. "constant" or specifically designed nucleotides). The constant nucleobases can be placed on either side of the randomly or degenerately designed sequence or interspersed among the randomly or degenerately designed nucleotides. In some embodiments, the molecular barcode comprises at least about 5 (such as at least about any one of 10, 15, 20, or 25) randomly and/or degenerately designed nucleobases. In some embodiments, the molecular barcode comprises at least about any one of 1, 2, 3, 4, 5, 6, 7, 8, 9, 10, or more constant (i.e., specifically designed) nucleobases. In some embodiments, the molecular barcode is a mixture of randomly designed, degenerately designed or constant nucleobases. The number of randomly and/or degenerately designed nucleobases in the molecular barcode depends on the complexity of the nucleic acid sample. In some embodiments, the non-duplex portion of the universal adaptor comprises a molecular barcode. In some embodiments, the molecular barcode is single-stranded. In some embodiments, the first strand of the universal adaptor comprises a molecular barcode at the 3' end of the unpaired portion. In some embodiments, the molecular barcode is double-stranded. In some embodiments, the duplex portion of the universal adaptor comprises a molecular barcode.

In some embodiments, the duplex portion of the universal adaptor comprises a sample barcode. A sample barcode may be used for target enrichment of one or more loci of interest from each nucleic acid sample. In some embodiments, the method comprises enriching target nucleotide sequences from a plurality of nucleic acid samples, wherein each nucleic acid sample is subject to steps (a)-(h) separately, and a universal adaptor comprising a different sample barcode is used for each nucleic acid sample. In some embodiments, the universal adaptor comprising a sample barcode is ligated to the nucleic acid templates in each nucleic acid sample, and the ligation products from different barcoded samples are pooled, and subject to the primer extension cycles and PCR amplification samples simultaneously, thereby each resulting amplicon comprises a sample barcode identifying which nucleic acid sample the amplicon is derived from. In some embodiments, the sample barcode comprises at least about any one of 3, 4, 5, 6, 8, 10, 12, 15 or more constant nucleotides. In some embodiments, the sample barcode comprises about any one of 4-15, 4-13, 5-12, 5-10, or 6-10 constant nucleotides. In some embodiments, the non-duplex portion of the universal adaptor comprises a sample barcode. In some embodiments, the duplex portion of the universal adaptor comprises a sample barcode. In some embodiments, the sample barcode is located at the ligatable end of the duplex portion (i.e., the duplex end comprising the 3' end of the paired portion on the first strand) of the universal adaptor. In some embodiments, the sample barcode is located at the first end of the universal adaptor.

Sample barcodes are useful for multiplexed sequencing of a plurality of samples in the same NGS sequencing reaction. Different sample barcodes may be used for different sequencing platforms. For example, ION TORRENT™ can sequence libraries having a sample barcode on one end of each amplicon. However, dual barcoding can be useful for construction of dual-indexing sequencing libraries for NGS sequencing on platforms such as ILLUMINA®. To provide amplicons with dual sample barcodes, for example, a sequencing adaptor primer comprising a sequence that is identical or complementary to the sample barcode in the universal adaptor can be used in the PCR amplification step.

In some embodiments, the universal adaptor comprises both a sample barcode and a molecular barcode. In some embodiments, the sample barcode is located at the first end of the universal adaptor, such as the ligatable end of the duplex portion. In some embodiments, the molecular barcode is located in the non-duplex portion, such as on the 3' end of the unpaired portion on the first strand of the universal adaptor. In some embodiments, the universal adaptor comprises: on the first strand from 5' to 3': a molecular barcode, and a sample barcode; and on the second strand from 5' to 3': sample barcode. In some embodiments, the universal adaptor comprises: on the first strand from 5' to 3': a sequence identical or complementary to the sequence of a first sequencing primer, a molecular barcode, and a sample barcode; and on the second strand from 5' to 3': sample barcode. In some embodiments, the universal adaptor comprises: on the first strand from 5' to 3': a molecular barcode, a sequence identical or complementary to the sequence of a first sequencing primer, a molecular barcode, and a sample barcode; and on the second strand from 5' to 3': a sequence complementary or identical to the sequence of a first sequencing primer, and a sample barcode. In some embodiments, the universal adaptor comprises: on the first strand from 5' to 3': a molecular barcode, a sample barcode, and a sequence identical or complementary to the sequence of a first sequencing primer, a molecular barcode; and on the second strand from 5' to 3': a sequence complementary or identical to the sequence of a first sequencing primer, and a sample barcode.

The sequence of the universal adaptor may be optimized to reduce non-specific side products from the primer extension cycles. One potential source of the non-specific side products can be produced as shown in FIG. 3. For example, in a first cycle of primer extension, a single-strand primer extension product is produced comprising a complementary sequence of the first strand of the universal adaptor, wherein the 3' portion comprises the reverse complement of the 5' unpaired portion of the universal adaptor. In a subsequent primer extension cycle, carry-over universal adaptor can anneal to the 3' portion of the single-stranded primer extension product having the complementary sequence of the 5' unpaired portion of the universal adaptor. However, the carry over universal adaptor would generally have a different molecular barcode, or unique molecule index (UMI). As a result, UMI inflation products could be amplified from this non-specific side product of primer extension. The severity of this problem may depend on the length of the 3' duplex portion of the universal adaptor that has constant bases, as opposed to molecular barcodes comprising degenerately designed nucleotides. In some embodiments, the first end of the universal adaptor comprises constant nucleobases of a sufficiently short length to prevent promiscuous priming during steps (b)-(f) by carryover universal adaptor. In some embodiments, the first end of the universal adaptor comprises about 5-15, such as about any one of 5, 6, 7, 8, 9, 10, 11, 12, 13, 14, or 15 of constant nucleobases on each strand. In some embodiments, the first end of the universal adaptor comprises about 6-12 constant nucleobases on each strand. In some embodiments, the UMI inflation problem can be alleviated or avoided by using a universal adaptor having the first (i.e., ligatable) end comprising constant nucleobases of a sufficiently short length. In some embodiments, the first end of the universal adaptor comprises no more than about any of 25, 20, 15, 12, 10, or fewer bps.

In some embodiments, the non-duplex portion of the universal adaptor comprises a 3' end having a blocking moiety. The blocking moiety prevents extension of the 3' end by the nucleic acid polymerase during the primer extension cycles. In some embodiments, the 3' end of the second strand of the universal adaptor has a blocking moiety, and is blocked from extension during the primer extension cycles. In some embodiments, the blocking moiety is an inverted nucleotide. In some embodiments, the 3' end of the second strand of the universal adaptor comprises an inverted nucleotide. In some embodiments, the blocking moiety is a stretch of flapping nucleotides having one or more (such as about any one of 1, 2, 3, 4, or more) phosphorothioate modifications. In some embodiments, the 3' end of the second strand of the universal adaptor comprises a stretch of flapping nucleotides having one or more (such as about any one of 1, 2, 3, 4, or more) phosphorothioate modifications. The flapping nucleotides can block primer extension by nucleic acid polymerases, while the one or more phosphorothioate modification is sufficient to prevent excision of the flapping nucleotides by a nuclease (such as the exonuclease function of the nucleic acid polymerase). In some embodiments, the stretch of flapping nucleotides has about any one of 1, 2, 3, 4, or more nucleotides. In some embodiments, the blocking moiety at the 3' end of the universal adaptor can prevent formation of hairpin structure on the template DNA due to complementary ends in the ligated nucleic acid, e.g., one by ligation and the other by primer extension in the absence of the blocking moiety. Formation of hairpin structure on the template DNA would result in low primer annealing and thus primer extension efficiency due to 'close down' of the template DNA.

The universal adaptor primer is designed to anneal to a complementary sequence of the non-duplex portion of the universal adaptor in the single-stranded primer extension products in the PCR amplification cycles. In some embodiments, the 3' portion of the universal adaptor primer comprises a sequence that is complementary to the first strand of the non-duplex portion of the universal adaptor. In some embodiments, the universal adaptor primer comprises at the 3' end a sequence complementary to about at least 12 (such as at least about any one of 15, 20, 25, 30, or more) 5'-most nucleotides on the first strand of the universal adaptor. In some embodiments, the 5' portion of the universal adaptor primer comprises a sequence identical or complementary to the sequence of a first sequencing primer of an NGS platform. In some embodiments, the universal adaptor primer comprises from the 5' to the 3': a sequence identical or complementary to the sequence of a first sequencing primer of an NGS platform and a sequence that is complementary to the first strand of the non-duplex portion of the universal adaptor.

Nested Target-Specific Primers

The methods described herein use one or more sets of outside primers and inside primers to enrich target nucleotide sequences having a locus of interest. The inside primer is nested with respect to an outside primer for a locus of interest. In some embodiments, one outside primer and one inside primer are used to amplify target nucleotide sequences having a locus of interest. In some embodiments, a plurality (such as any one of 2, 3, 4, 5, 6, 10, 12, 15 or more) of outside primers and a plurality (such as any one of 2, 3, 4, 5, 6, 10, 12, 15 or more) inside primers are used to amplify target nucleotide sequences having a locus of interest. In some embodiments, the outside primers and inside primers for one locus of interest anneal specifically to the same strand of the template nucleic acids. In some embodiments, a plurality of outside primers and corresponding inside primers anneal specifically to one strand of the template nucleic acids, and a plurality of outside primers and corresponding inside primers anneal specifically to the complementary strand of the template nucleic acids.

In some embodiments, when a plurality of sets of outside and inside primers is used for one locus of interest, multiple distinguishable amplicons are obtained. In some embodiments, amplicons that overlap each other are produced to allow tiling of target sequences over a locus of interest that is longer than each target sequence. In some embodiments, these multiple amplicons can be sequenced, and overlapping sequence reads can be compared with each other to detect sequence errors introduced during primer extension and PCR amplification cycles or sequencing processes. In some embodiments, individual amplicons can be aligned and where they differ in the sequence present at a particular base, an artifact or error from the target enrichment steps and/or sequencing may be present.

In some embodiments, a first set of outside primer and inside primer that specifically anneal to the first strand of the ligated nucleic acid comprising the target nucleotide sequence, and a second set of outside primer and inside primer that specifically anneal to the second strand of the ligated nucleic acid comprising a complementary target nucleotide sequence are used to enrich each locus of interest. See FIG. 2 for two exemplary sets of outside and inside primers that can be used to enrich target nucleotide sequences on both strands (i.e., a target nucleotide sequence and a complementary target nucleotide sequence) of a nucleic acid template having a locus of interest.

In some embodiments, to significantly reduce or eliminate PCR amplification products from outside primers or inside primers in opposite directions, the outside primers having opposite directions each comprises an identical 5' nucleotide sequence, which is referred herein as "5' tag sequence." In some embodiments, the inside primers having opposite directions also each comprises a 5' tag sequence that can be the same or different from the 5' tag sequence of the outside primers. In some embodiments, the 5' tag sequence is of sufficient length to suppress PCR amplification using the outside primers. For example, a duplex PCR amplicon arising from two outside primers having opposite directions form "pan-handle" structures due to complementary sequences on the ends (i.e., 5' tag sequence and its complement). In some embodiments, the 5' tag sequence comprises at least about any one of 13, 15, 20, 25, 30, or more nucleotides. The 5' tag sequences in the outside and inside primers can also reduce primer dimer formation, thereby improving efficiency of the primer extension and/or PCR amplification cycles.

In some embodiments, the 5' tag sequences of the outside primers and/or the inside primers is optimized according to any one or more of the following design principles: (i) the 5' tag sequences have no known or few genomic target themselves; (ii) the 5' tag sequences have high Tms (such as at least about any one of 65° C., 70° C., 75° C., or higher); (iii) the 5' tag sequences are not prone to primer dimer formation by themselves or with other primers in the reaction mixture; and (iv) the 5' tag sequences have no stable secondary structure. See, for example, Diagnostics Z. et al. "The elimination of primer-dimer accumulation in PCR," *Nuc. Acids Res.*, 1997, 25 (16): 3235-3241. In some embodiments, the GC content of the 5' tag sequence is optimized to avoid primer dimer formation or non-specific priming in the primer extension cycles. In some embodiments, the GC content of the universal adaptor is substantially similar to the GC content of the nucleic acid templates. In some embodiments, the GC content of the universal adaptor is at least about any one of 40%, 45%, 50%, 55%, 60%, 65% or higher.

In some embodiments, each set of outside and inside primers can specifically anneal to a known nucleotide sequence in the vicinity of the locus of interest. The target nucleotide sequences having the locus of interest must have one or more known nucleotide sequences at one end to enable design of outside and inside primers. One powerful advantage of the methods described herein compared to routine PCR enrichment techniques is the anchoring of the nested target-specific primers on one side of the nucleic acid templates comprising the target nucleotide sequences, while the other end is randomly ligated with the universal adaptor. In contrast to other routine PCR techniques, the methods described herein enable enrichment of a target region with knowledge of only one of its ends. In some embodiments, different sets of outside and inside primers are designed to enrich different fragments, such as exons, of a gene. Known sequences of genes can be obtained based on reference genome sequences from publicly available databases. Other means for de novo determination of sequences can also be used to provide the known sequences in the vicinity of a locus of interest, including for example, genomic or exome DNA sequencing. The known nucleotide sequence may be at least about any one of 10, 20, 30, 40, 50, 100, 200 or more nucleotides long. In some embodiments, the known nucleotide sequence has a length of any one of about 10 to 100 nucleotides, about 10 to 500 nucleotides, about 10 to 1000 nucleotides, about 100 to 500 nucleotides, about 100 to 1000 nucleotides, about 500 to 1000 nucleotides, or about 500 to 5000 nucleotides. The known nucleotide sequence can be either upstream or downstream of the locus of interest, and can be on the sense strand or antisense strand.

The distance between the known nucleotide sequence and the locus of interest can be of any length suitable for primer extension and PCR amplification. In some embodiments, the known nucleotide sequence is no more than about any one of 1000, 900, 800, 700, 600, 500, 400, 300, 200, 100, 50, 30, 20 or fewer bp from the locus of interest. In some embodiments, the outside and inside primers are designed to provide amplicons of a suitable length for use in a particular sequencing technology. For example, if the optimal read-length of a given sequencing technology is 200 bp, the amplicons of the target nucleotide sequences from the methods described herein may have an average length of about 400 bp or fewer.

The methods described herein allow for enriching target nucleotide sequences contiguous to a known nucleotide sequence on either or both flanks of the known nucleotide sequence. Regardless of whether the nucleic acid template normally exists as a single-stranded or double-stranded nucleic acid, sequence information is typically represented in a single-stranded format (Strand A), from 5' to 3'. If the sequence 5' of the known target nucleotide sequence of Strand A is to be determined, the gene-specific primers can be complementary (i.e. anneal to) Strand A. If the sequence 3' of the known target nucleotide sequence of Strand A is to be determined, the gene-specific primers can be identical to Strand A, such that they will anneal to the complementary strand of a double-stranded nucleic acid. Such considerations of primer design are well known to those of ordinary skill in the art.

The target nucleotide sequences having a locus of interest may comprise the sequences (on either the sense strand and/or antisense strand) of the locus of interest, known nucleotide sequences in the vicinity of the locus of interest, and adjacent nucleotide sequence which is to be determined (which may be referred to as an unknown sequence). A target nucleotide sequence can be of any appropriate length. In some embodiments, a population of target nucleotide sequences are enriched by the methods described herein, and wherein the population of target nucleotide sequences have the same 5' or 3' end sequence, which match the sequences of the inside primers.

In some embodiments, the outside primer is a single-stranded oligonucleotide comprising a 3' portion comprising a sequence that can specifically anneal to a portion of a known nucleotide sequence in the vicinity of a locus of interest. In some embodiments, the outside primer comprises at the 3' end a sequence that can specifically anneal to a first known nucleotide sequence (i.e., first annealing site) in the vicinity of a locus of interest. In some embodiments, the inside primer comprises at the 3' end a sequence that can specifically anneal to a second known nucleotide sequence (i.e., second annealing site) in the vicinity of a locus of interest. In some embodiments, the first known nucleotide sequence is about 1-100 nucleotides (such as about any one of 2-50, 1-20, or 1-10 nucleotides) farther away from the locus of interest than the second known nucleotide sequence. In some embodiments, the outside primer anneals to a region about 1-100 nucleotides farther away from the locus of interest than the inside primer. In some embodiments, the outside primer anneals to a region no more than about any one of 100, 80, 60, 50, 40, 30, 20, 10, 5 or fewer nucleotides farther away from the locus of interest than the inside primer.

In some embodiments, the inside primer is nested with respect to the outside primer. In some embodiments, the inside primer is nested with respect to the outside primer by at least about any one of 1, 2, 3, 4, 5, 6, 7, 8, 9, 10, 15, 20, or more nucleotides.

The outside and inside primers can be designed to anneal to known sequences of high specificity to reduce or avoid off-target priming. In some embodiments, the 3' portions of the outside primer and/or the inside primers comprise at least 10 (such as at least about any one of 12, 13, 14, 15, 20, 25, 30, 35 or more) nucleotides that specifically anneal to known nucleotide sequences in the vicinity of the locus of interest. In some embodiments, the 3' portions of the outside primer and the inside primer have no more than about any one of 20, 15, 10, 5, 4, 3, or 2 different annealing loci on the nucleic acid templates. "Different annealing loci" refer to sequences in the nucleic acid templates that have different known genomic locations and/or belong to different genes or gene fusion products, and the sequences are complementary or substantially complementary to the 3' portions of the outside or inside primer.

In some embodiments, portions of the outside and inside primers that specifically anneal to the known target nucleotide sequences can anneal specifically at a temperature of about any one of 55-72° C., 60-72° C., about 60-70° C., about 62-69° C., about 63-67° C., or about 64-66° C. In some embodiments, portions of the outside and inside primers that specifically anneal to the known target nucleotide sequences can anneal specifically at a temperature of about 65° C. in a primer extension or PCR buffer.

The outside primer, the inside primer, or their 3' target-specific portions thereof, can specifically anneal to an exon of a gene, an intron of a gene, an intron-exon junction of a gene, or a non-coding region of the genome. The locations of the annealing site for the outside and inside primers can be designed according to the nature of the locus of interest, and the type of nucleic acid templates in the nucleic acid sample. For example, to enrich a locus in the exon region of a gene from a genomic DNA sample, outside and inside primers can be designed to specifically anneal to a known sequence in an intron in the vicinity of the locus in the direction that goes into the exon region. In some embodiments, to enrich a locus in a fused gene from a cDNA sample, a first set of outside and inside primers can be designed to specifically anneal to a known sequence in an exon of the first fused gene in the direction that goes towards the fusion point, and a second set of outside and inside primers can be designed to specifically anneal to a known sequence in an exon of the second fused gene in the direction that goes towards the fusion point.

In some embodiments, the outside primer and the inside primer comprise the same 5' portion, which may suppress formation of primer dimers. In some embodiments, the inside primer comprises at the 5' end a sequence identical to or complementary to the sequence of a second sequencing primer of an NGS platform.

Nucleic Acid Sample

The methods described herein can be used for a variety of nucleic acid samples. In some embodiments, the nucleic acid sample comprises genomic DNA or fragments thereof. In some embodiments, the nucleic acid sample comprises RNA, e.g. mRNA, miRNA, lincRNA, rRNA, etc., or fragments thereof. In some embodiments, the nucleic acid sample comprises cDNA or fragments thereof. In some embodiments, the nucleic acid sample comprises a mixture of genomic DNA and RNA. In some embodiments, the nucleic acid sample comprises a mixture of genomic DNA and cDNA.

In some embodiments, the nucleic acid sample comprises DNA templates. In some embodiments, the nucleic acid sample comprises RNA templates. In some embodiments, the nucleic acid sample comprises both DNA templates and RNA templates. In some embodiments, the nucleic acid templates are genomic DNA. In some embodiments, the nucleic acid templates are chromosomal DNA. In some embodiments, the nucleic acid templates are mitochondrial DNA. In some embodiments, the nucleic acid templates are exome DNA. In some embodiments, the nucleic acid templates are cDNA. In some embodiments, the nucleic acid templates are RNA, e.g. mRNA, miRNA, lincRNA, rRNA, etc. In some embodiments, the nucleic acid templates are derived, such as fragmented, from nucleic acids having a length beyond the optimal reading length of the NGS method or platform, such as full-length chromosomal DNA, or full-length mRNA.

In some embodiments, the nucleic acid sample comprises cDNA. In some embodiments, the cDNA is obtained by reverse transcription of total RNA or fractions thereof, such as mRNA, miRNA, or other non-coding RNA. In some embodiments, the cDNA is single-stranded, e.g., at least about any one of 10%, 20%, 30%, 40%, 50%, 60%, 70%, 80%>, 90%, or 95% or more of the cDNA is single-stranded. In some embodiments, the nucleic acid sample comprises double-stranded cDNA.

In some embodiments, the nucleic acid sample comprises gDNA. In some embodiments, the gDNA is single-stranded, e.g., at least about any one of 10%, 20%, 30%, 40%, 50%, 60%, 70%, 80%, 90%, 95% or more of the gDNA is single-stranded. In some embodiments, the nucleic acid sample comprises double-stranded gDNA.

In some embodiments, the nucleic acid sample comprises a mixture of cDNA and gDNA. In some embodiments, weight ratio between the cDNA and the gDNA is more than about any one of 1:5, 1:3, 1:2, 1:1, 2:1, 3:1, 5:1, 10:1, or more.

In some embodiments, the nucleic acid sample comprises a low amount of nucleic acid templates. In some embodiments, the nucleic acid sample comprises no more than about any one of 1000 ng, 500 ng, 200 ng, 100 ng, 50 ng, 40 ng, 30 ng, 25 ng, 20 ng, 15 ng, 10 ng, 5 ng, 4 ng, 3 ng, 2 ng, 1 ng or less of nucleic acid templates, such as cDNA, gDNA, RNA, a combination thereof, or total nucleic acid.

In some embodiments, the nucleic acid sample is derived from a cell or tissue sample. In some embodiments, the nucleic acid sample is derived from a cell line sample or from cultured cells. In some embodiments, the nucleic acid sample is derived from a genetically engineered cell line. In some embodiments, the nucleic acid sample is derived from a cell engineered with CRISPR gene editing technology. In some embodiments, the nucleic acid sample is derived from an immune cell, such as a T cell, a B cell, or a PMBC. In some embodiments, the nucleic acid sample is derived from a tumor cell.

In some embodiments, the nucleic acid sample is obtained from a food sample, an environmental sample, or a biological sample. In some embodiments, the nucleic acid sample is derived from a biological sample from an individual. In some embodiments, the nucleic acid sample is derived from a biological sample from in need of treatment for a disease (such as cancer). In some embodiments, the nucleic acid sample is a diagnostic sample obtained from an individual.

In some embodiments, the nucleic acid sample is derived from a biological sample from a healthy individual. In some embodiments, the nucleic acid sample is derived from a genetically engineered animal (such as mice, rats, or non-human primates). In some embodiments, the nucleic acid sample is derived from an animal engineered using CRISPR gene editing technologies.

In some embodiments, the biological sample further comprises proteins, cells, fluids, biological fluids, preservatives, and/or other substances. By way of non-limiting example, a sample can be a cheek swab, blood, serum, plasma, sputum, cerebrospinal fluid, urine, tears, alveolar isolates, pleural fluid, pericardial fluid, cyst fluid, tumor tissue, tissue, a biopsy, saliva, an aspirate, or combinations thereof. In some embodiments, the biological sample is obtained by resection or biopsy.

In some embodiments, the nucleic acid sample is derived from a blood sample of an individual. In some embodiments, the nucleic acid sample is derived from a Peripheral Mononuclear Blood Cell (PMBC) sample of an individual. In some embodiments, the nucleic acid sample is derived from a fraction of immune cells (such as T cells, NK cells or B cells) in the blood sample of an individual. In some embodiments, the nucleic acid templates are cell-free DNA. In some embodiments, the nucleic acid templates are cell-free DNA derived from a blood sample of an individual. In some embodiments, the nucleic acid templates are circulating tumor DNA (i.e., ctDNA). In some embodiments, the nucleic acid templates are derived from circulating tumor cells from a blood sample of an individual.

In some embodiments, the nucleic acid sample is derived from a biopsy sample of an individual. In some embodiments, the nucleic acid sample is derived from a tumor biopsy, such as untreated biopsy tissue or treated biopsy tissue. In some embodiments, the nucleic acid sample is derived from formalin-fixed and/or paraffin-embedded biopsy tissue from an individual.

In some embodiments, the biological sample is obtained from an individual in need of treatment for a disease associated with a genetic alteration, e.g. cancer or a hereditary disease. In some embodiments, a known target sequence is present in a disease-associated gene. In some embodiments, the biological sample is obtained from an individual in need of treatment for cancer. In some embodiments, the biological sample comprises tumor cells from one or more tumor sites in an individual.

In some embodiments, the biological sample is freshly collected from an individual. In some embodiments, the biological sample is stored for a period of time, such as at least about any one of 1 day, 1 week, 1 month, 3 months, 6 months, 1 year, or more prior to being used in the methods described herein. In some embodiments, the biological sample is a Formalin-Fixed Paraffin-embedded (FFPE) sample. In some embodiments, the biological sample is directly used as the nucleic acid sample in the methods described herein. In some embodiments, the biological sample is pre-treated by dilution and/or suspension in a solution. In some embodiments, the biological sample is obtained from a subject and preserved or processed prior to being used in the methods described herein. For example, a biological sample can be embedded in paraffin wax, refrigerated, or frozen. A frozen biological sample can be thawed before use. Other exemplary treatment or processing of a biological sample include, but are not limited to, centrifugation, filtration, sonication, homogenization, heating, freezing and thawing, contacting with a preservative (e.g. anti-coagulant or nuclease inhibitor) and any combination thereof. In some embodiments, the biological sample is treated with a chemical and/or biological reagent. Chemical and/or biological reagents can be employed to protect and/or maintain the stability of the biological sample or nucleic acid templates contained therein during processing and/or storage. In some embodiments, chemical and/or biological reagents can be employed to release nucleic acid templates from other components of the biological sample. By way of non-limiting example, a blood sample can be treated with an anti-coagulant prior to being used to obtain a nucleic acid sample for use in the methods described herein. The skilled artisan is well aware of methods and processes for processing, preservation, or treatment of biological samples, and methods of isolating nucleic acids from biological samples or cell samples for nucleic acid analysis. In some embodiments, the biological sample is a clarified fluid sample, for example, by centrifugation. In some embodiments, the biological sample is clarified by low-speed centrifugation (e.g. 3,000×g or less) followed by collection of the supernatant comprising the clarified fluid sample.

In some embodiments, the nucleic acid templates in a biological sample or nucleic acid sample can be isolated, enriched, or purified prior to being used in methods described herein. Suitable methods of isolating, enriching, or purifying nucleic acids from a sample may be used. For example, kits for isolation of genomic DNA and RNA from various sample types are commercially available (e.g. Qiagen; Germantown, Md.). The methods of target enrichment described herein can be used singly or in combination with other target enrichment methods known in the art. In some embodiments, the method does not comprise hybridization enrichment.

In some embodiments, a nucleic acid sample comprising RNA templates can be used in methods described herein. The nucleic acid sample may comprise total nucleic acids extracted from either fresh or degraded specimens without the need of genomic DNA removal for cDNA sequencing. In some embodiments, the nucleic acid sample comprising RNA is not treated for ribosomal RNA depletion for cDNA sequencing. In some embodiments, the nucleic acid sample comprising RNA is not mechanically or enzymatically sheared in any of the steps. In some embodiments, the RNA is not subjected to double-stranded cDNA synthesis using random hexamers for use in the methods described herein.

Loci of Interest

Many loci of interest may be studied using the methods described herein. In some embodiments, the locus of interest is associated with a sequence variant, including, but not limited to, chromosomal rearrangement, Single Nucleotide Variant (SNV), indel, splice variant, Copy Number Variant (CNV), and combinations thereof. In some embodiments, the locus of interest is associated with a chromosomal rearrangement, such as a chromosomal fusion, or a gene fusion. In some embodiments, the locus of interest is associated with a chromosomal translocation. In some embodiments, the locus of interest is associated with a single nucleotide variant (SNV). In some embodiments, the locus of interest is associated with an insertion mutation, or a deletion mutation, collectively known as "indel" mutation. In some embodiments, the locus of interest is associated with a substitution mutation. In some embodiments, the locus of interest is associated with a copy number variant. In some embodiments, the locus of interest is associated with a splice variant. The locus of interest may be of any length, including, for example, at least any one of 1, 2, 5, 10, 20, 50, 100, 200, 300, 400, 500, 1000, 2000 or more bp.

In some embodiments, the locus of interest is located in a naturally occurring gene. In some embodiments, the locus of interest can be any one or more contiguous exons, introns, intron-exon junction, 5' UTR, 3'UTR, or other non-coding regions of a gene of interest, as well as fragments thereof. In some embodiments, the locus of interest is located in an engineered gene or genomic site. In some embodiments, the locus of interest is located in a gene associated with a hereditary disease. In some embodiments, the locus of interest is located in a gene associated with cancer, such as an oncogene. In some embodiments, the locus of interest is associated with an immune cell receptor, such as T cell receptor, including recombinant T cell receptors. In some embodiments, the locus of interest is associated with a genetically engineered site, such as an off-target site (e.g., previously known or unknown off-target site) of CRISPR gene editing.

A gene or locus "associated with" a disease or condition refers to a gene or locus whose alteration, such as a deletion, insertion, SNV, chromosomal rearrangement (such as gene fusion), compared to the wildtype sequence in a healthy individual, at least in part causes or correlates with a disease or condition. For example, a disease can be caused by, at least in part, by an alteration in the gene or locus of the individual if the alteration increases the risk of the individual developing the disease, increases the subject's susceptibility to a disease (including infectious diseases, or diseases with an infectious component), causes the production of a disease-associated molecule, or causes cells to become diseased or abnormal (e.g. loss of cell cycle regulation in cancer cells). Diseases can be associated with multiple genetic alterations.

In some embodiments, the locus of interest is associated with a fusion sequence resulting from a chromosomal or gene rearrangement. In some embodiments, the methods described herein are suited for determining the presence and/or identity of a gene rearrangement. In some embodiments, identity of one portion of a gene rearrangement is previously known (e.g., the portion of a gene rearrangement that is to be targeted by the outside and inside primers) and the sequence of the other portion may be determined using methods disclosed herein. In some embodiments, a gene rearrangement involves an oncogene. In some embodiments, a gene rearrangement comprises a fusion oncogene.

III. Method of Determining Target Nucleotide Sequences and Applications Thereof

The present application further provides methods of determining target nucleotide sequences having one or more loci of interest in a nucleic acid sample by sequencing amplicons of the target nucleotide sequences using any one of the methods of target enrichment as described above.

Thus, in some embodiments, there is provided a method of determining a target nucleotide sequence having a locus of interest in a nucleic acid sample comprising a nucleic acid template comprising the target nucleotide sequence, the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the target nucleotide sequence; (c) annealing an outside primer to the first strand of the ligated nucleic acid in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) repeating steps (c)-(e) for one or more primer extension cycles; (g) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; (h) repeating step (g) for one or more (such as about 2-100, e.g., about 5-50, or about 10-30) cycles of PCR amplification to provide amplicons of the target nucleotide sequence; and (i) performing next-generation sequencing of the amplicons of the target nucleotide sequence, thereby providing the target nucleotide sequence. In some embodiments, steps (a)-(h) uses a first set of outside primer and inside primer that specifically anneal to the first strand of the ligated nucleic acid, and a second set of outside primer and inside primer that specifically anneal to the second strand of the ligated nucleic acid. In some embodiments, the outside primer of the first set and the outside primer of the second set comprises a first 5' tag sequence of at least 13 nucleotides long and the inside primer of the first set and the inside primer of the second set comprises a second 5' tag sequence of at least 13 nucleotides long.

Methods described herein can be employed in a multiplex format. In some embodiments, the method is used to determine target nucleotide sequences and/or detect sequence variants having a plurality of different loci of interest. In some embodiments, target nucleotide sequences having at least about 1500 (such as at least about 2000, 2500, 3000, 4000, 5000 or more) different loci of interest are determined simultaneously. In some embodiments, target nucleotide sequences having about 2-5000, such as about any one of 2-100, 5-200, 100-2000, 2-2000, 101-5000, 1500-5000, loci of interest are determined simultaneously. In some embodiments, the average coverage by reads for each target nucleotide sequence is at least about any one of 2×, 10×, 20×, 50×, 100×, 200×, 500×, 1000×, 10000× or higher.

In some embodiments, the target nucleotide sequences having a locus of interest are from a single nucleic acid sample. In some embodiments, the target nucleotide sequences having a locus of interest from a plurality (such as at least about any one of 2, 3, 4, 5, 6, 7, 8, 10 or more) of nucleic acid samples. Different nucleic acid samples may be barcoded using universal adaptors comprising sample barcodes, and pooled either before the primer extension cycles, or their amplicons can be pooled at the end of the target enrichment steps to allow simultaneous sequencing of target nucleotide sequences from multiple nucleic acid samples.

In some embodiments, sequences suitable for sequencing primers used in specific NGS platforms are introduced to the amplicons of target nucleotide sequences during the target enrichment steps. In some embodiments, the universal adaptor (such as the non-duplex portion or the duplex portion) comprises a sequence identical or complementary to the sequence of a first sequencing primer used in step (i), or the universal adaptor primer comprises at the 5' end a sequence identical or complementary to the sequence of the first sequencing primer. In some embodiments, wherein step (g) comprises contacting the single-stranded primer extension products with a DNA polymerase, a universal adaptor primer, an inside primer, and a sequencing adaptor primer under a condition sufficient for PCR amplification of the target nucleotide sequence, wherein the sequencing adaptor primer comprises at the 3' end a sequence identical to a sequence of the inside primer, and at the 5' end a sequence identical or complementary to the sequence of a second sequencing primer used in step (ii).

In some embodiments, the method further comprises preparing a sequencing library using the amplicons of the target nucleotide sequence prior to the next-generation sequencing of step (ii). In some embodiments, the method comprises cleaning up the amplicons of target nucleotide sequences after the PCR amplification cycles. In some embodiments, the method comprises fragmenting the amplicons. In some embodiments, the method comprises quantifying the amplicons of target nucleotide sequences from a plurality of samples, and pooling the amplicons of target nucleotide sequences together as a single sequencing library. In some embodiments, the amplicons of the target nucleotide sequences are subjected to additional processes to add adaptors and/or sequencing primer sequences to construct a sequencing library for the sequencing step.

As used herein "next-generation sequencing" or "NGS" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina): SOLiD technology (Applied Biosystems); Ion semiconductor sequencing (ION TORRENT™); DNA nanoball sequencing (Complete Genomics); and technologies available from Pacific Biosciences, Intelligen Bio-systems, Oxford Nanopore Technologies, and Helicos Biosciences.

In some embodiments, the sequencing primers can comprise portions compatible with the selected next-generation sequencing method. Next-generation sequencing technologies and the constraints and design parameters of associated sequencing primers are well known in the art (see, e.g. Shendure, et al., "Next-generation DNA sequencing," Nature, 2008, vol. 26, No. 10, 1 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 201 1, 1 1(3):333-43; Zhang et al., "The impact of next-generation sequencing on genomics", J Genet Genomics, 201 1, 38(3): 95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/ 0252077; 2007/0070349; and 20070070349; which are incorporated by reference herein in their entireties).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of sequence by synthesis (SBS) techniques, cycle sequencing is accomplished by stepwise addition of reversible terminator nucleotides containing, for example, a cleavable or photobleachable dye label as described, for example, in U.S. Pat. Nos. 7,427,673, 7,414,116 and 7,057,026, the disclosures of which are incorporated herein by reference. This approach is being commercialized by Solexa (now Illumina Inc.), and is also described in WO 91/06678 and WO 07/123,744 (filed in the United States patent and trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Additional example SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010,251, the disclosures of which are incorporated herein by reference in their entireties.

Some embodiments can utilize sequencing by ligation techniques. Such techniques utilize DNA ligase to incorporate short oligonucleotides and identify the incorporation of such short oligonucleotides. Example SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can include techniques such as next-next technologies. One example can include nanopore sequencing techniques (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). In some such embodiments, nanopore sequencing techniques can be useful to confirm sequence information generated by the methods described herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference in their entireties) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Application Publication No. 2008/0108082 (each of which is incorporated herein by reference in their entireties). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nanostructures." Proc. Natl. Acad. Sci. USA 105, 1176-1181 (2008), the disclosures of which are incorporated herein by reference in their entireties). In one example single molecule, real-time (SMRT) DNA sequencing technology provided by Pacific Biosciences Inc. can be utilized with the methods described herein. In some embodiments, a SMRT chip or the like may be utilized (U.S. Pat. Nos. 7,181,122, 7,302,146, 7,313,308, incorporated by reference in their entireties). A SMRT chip comprises a plurality of zero-mode waveguides (ZMW). Each ZMW comprises a cylindrical hole tens of nanometers in diameter perforating a thin metal film supported by a transparent substrate. When the ZMW is illuminated through the transparent substrate, attenuated light may penetrate the lower 20-30 nm of each ZMW creating a detection volume of about 1×10-21 L. Smaller detection volumes increase the sensitivity of detecting fluorescent signals by reducing the amount of background that can be observed.

SMRT chips and similar technology can be used in association with nucleotide monomers fluorescently labeled on the terminal phosphate of the nucleotide (Korlach J. et al., "Long, processive enzymatic DNA synthesis using 100% dye-labeled terminal phosphate-linked nucleotides." Nucleosides, Nucleotides and Nucleic Acids, 27:1072-1083, 2008; incorporated by reference in its entirety). The label is cleaved from the nucleotide monomer on incorporation of the nucleotide into the polynucleotide. Accordingly, the label is not incorporated into the polynucleotide, increasing the signal:background ratio. Moreover, the need for conditions to cleave a label from a labeled nucleotide monomer is reduced.

An additional example of a sequencing platform that may be used in association with some of the embodiments described herein is provided by Helicos Biosciences Corp. In some embodiments, true single molecule sequencing can be utilized (Harris T. D. et al., "Single Molecule DNA Sequencing of a viral Genome" Science 320:106-109 (2008), incorporated by reference in its entirety). In one embodiment, a library of target nucleic acids can be prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid. In one embodiment, fluorescently-labeled nucleotide monomer, namely, A, C, G, or T, are delivered one at a time to the target nucleic acid in the presence DNA polymerase. Incorporation of a labeled nucleotide into the polynucleotide complementary to the target nucleic acid is detected, and the position of the fluorescent signal on the glass cover slip indicates the molecule that has been extended. The fluorescent label is removed before the next nucleotide is added to continue the sequencing cycle. Tracking nucleotide incorporation in each polynucleotide strand can provide sequence information for each individual target nucleic acid.

The methods described herein may further comprise one or more data analysis steps. Sequencing reads can be analyzed using various methods. In some embodiments, an automated process, such as computer software, is used to analyze the sequencing reads to detect an allele (such as wild type allele, or a mutation, such as a chromosomal rearrangement, SNV, indel, CNV, or splice variant) at a target locus. In some embodiments, sequencing reads of amplicons derived from the same template nucleic acid are identified and consolidated into a single sequence based on the sequences of the molecular barcodes in the sequencing reads. In some embodiments, nucleotide sequences derived from DNA templates and RNA templates are analyzed simultaneously to detect mutations. Also provided herein are computer software and systems for determining nucleotide sequences of a plurality of target loci.

Methods of aligning sequencing reads to known sequence databases of genomic and/or cDNA sequences are well known in the art and software is commercially available for this process. In some embodiments, reads (less the sequencing primer and/or adaptor nucleotide sequence) which do not map, in their entirety, to wild-type sequence databases can be genomic rearrangements or large indel mutations. In some embodiments, reads (less the sequencing primer and/or adaptor nucleotide sequence) comprising sequences which map to multiple locations in the genome can be genomic rearrangements.

Some embodiments described herein comprise comparing the target nucleotide sequences in a nucleotide sample to a reference sequence, and/or comparing the target nucleotide sequences of one sample to that of a reference sample. The reference sequence and reference values may be obtained from a database. The reference sample may be derived from a sample from a healthy or wildtype individual, tissue, or cell. For example, in some embodiments, the target nucleotide sequences from a tumor cell of an individual is analyzed and compared to the target nucleotide sequences from a healthy cell of the same individual to provide a diagnosis.

Methods of Detecting Sequence Variants

Also provided are methods of detecting a sequence variant at a locus of interest in a nucleic acid sample comprising nucleic acid templates, comprising determining target nucleotide sequences having one or more loci of interest in the nuclei acid sample using any one of the methods of determining target nucleotide sequences described herein, and detecting the sequence variant in the target nucleotide sequence.

In some embodiments, there is provided a method of detecting a sequence variant at a locus of interest in a nucleic acid sample comprising a nucleic acid template comprising a target nucleotide sequence having the locus of interest, the method comprising: (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (b) dissociating the ligated nucleic acid into a first strand and a second strand, wherein the first strand comprises the target nucleotide sequence; (c) annealing an outside primer to the first strand of the ligated nucleic acid in the vicinity of the target nucleotide sequence; (d) extending the outside primer over the full length of the first strand of the ligated nucleic acid using a DNA polymerase to provide a nascent primer extension duplex; (e) dissociating the nascent primer extension duplex at a sufficiently high temperature into the first strand of the ligated nucleic acid and a single-stranded primer extension product; (f) repeating steps (c)-(e) for one or more primer extension cycles; (g) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; (h) repeating step (g) for one or more (such as about 2-100, e.g., about 5-50, or about 10-30) cycles of PCR amplification to provide amplicons of the target nucleotide sequence; (i) performing next-generation sequencing of the amplicons of the target nucleotide sequence; and (j) detecting the sequence variant in the sequencing reads. In some embodiments, steps (a)-(h) uses a first set of outside primer and inside primer that specifically anneal to the first strand of the ligated nucleic acid, and a second set of outside primer and inside primer that specifically anneal to the second strand of the ligated nucleic acid. In some embodiments, the outside primer of the first set and the outside primer of the second set comprises a first 5' tag sequence of at least 13 nucleotides long and the inside primer of the first set and the inside primer of the second set comprises a second 5' tag sequence of at least 13 nucleotides long.

A variety of sequence variants can be detected using the methods described herein. In some embodiments, the sequence variant is inherited in germline DNA. In some embodiments, the sequence variant arises from a somatic mutation or chromosomal rearrangement. In some embodiments, the sequence variant arises from somatic hypermutation, e.g., for providing diverse immune receptors such as T cell or B cell receptors. In some embodiments, the sequence variant is an engineered sequence variant. In some embodiments, the sequence variant is an off-target mutation due to genetic engineering, such as CRISPR gene editing.

In some embodiments, a plurality of sequence variants are detected. The sequence variants detected herein is not limited to a single type. In some embodiments, the plurality of sequence variants are selected from the group consisting of chromosomal rearrangements, splice variants, point mutations, deletions, insertions, and combinations thereof. In some embodiments, the plurality of sequence variants comprises a gene fusion. In some embodiments, the plurality of sequence variants comprises a chromosomal rearrangement. In some embodiments, the plurality of sequence variants comprises a chromosomal translocation. In some embodiments, the plurality of sequence variants comprises a single nucleotide mutation. In some embodiments, the plurality of sequence variants comprises a SNV. In some embodiments, the plurality of sequence variants comprises an indel, such as an insertion or a deletion. In some embodiments, the method simultaneously detects gene fusions based on RNA sequences (or cDNA sequences) and a mutation (such as SNV or indel) based on genomic DNA sequences. In some embodiments, the method uses a nucleic acid sample derived from an FFPE sample for simultaneous detection based on RNA and DNA. In some embodiments, the method uses a ctDNA sample.

Methods of bisulfite sequencing for analyzing methylation status of target nucleic acids (such as genomic DNA) are also provided herein. DNA methylation is a widespread epigenetic modification that plays a pivotal role in the regulation of the genomes of diverse organisms. The most prevalent and widely studied form of DNA methylation in mammalian genomes occurs at the 5 carbon position of cytosine residues, usually in the context of the CpG dinucleotide. Methods of whole genome bisulfite sequencing that can be used to detect 5mC have been described. Treatment of genomic DNA with sodium bisulfite chemically deaminates cytosines much more rapidly than 5mC, preferentially converting them to uracils. With NGS, these can be detected on a genome-wide scale at single base-pair resolution. Any of the known bisulfite sequencing workflows can be applied to the methods described herein to provide methods of methylation analysis of target nucleotide sequences having one or more loci of interest with high accuracy and efficiency.

In some embodiments, the sequence variant is present at a low allele frequency. For example, the sequence variant may be present at a frequency of no more than about any one of 1 copy per 5 nucleic acid templates, 1 copy per 10 nucleic acid templates, 1 copy per 50 nucleic acid templates, 1 copy per 100 nucleic acid templates, 1 copy per 500 nucleic acid templates, 1 copy per 1000 nucleic acid templates, 1 copy per 10000 nucleic acid templates or less.

IV. Applications

The methods as described above can be used in a variety of applications, including, but not limited to clinical diagnosis and prognosis and tools for genetic engineering. In some embodiments, there is provided a method of diagnosing a disease (such as hereditary disease or cancer) in an individual, comprising detecting a sequence variant associated with the disease at a locus of interest in a nucleic acid sample from the individual using any one of the methods described herein, thereby providing a diagnosis of the disease.

Thus, in some embodiments, there is provided a method of diagnosing a disease (such as hereditary disease or cancer) in an individual, comprising: (a) obtaining a nucleic acid sample comprising a nucleic acid template comprising a target nucleotide sequence from the individual; (b) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end; (c) dissociating the ligated nucleic acid into a first strand and a second strand, wherein the first strand comprises the target nucleotide sequence; (d) annealing an outside primer to the first strand of the ligated nucleic acid in the vicinity of the target nucleotide sequence; (e) extending the outside primer over the full length of the first strand of the ligated nucleic acid using a DNA polymerase to provide a nascent primer extension duplex; (f) dissociating the nascent primer extension duplex at a sufficiently high temperature into the first strand of the ligated nucleic acid and a single-stranded primer extension product; (g) repeating steps (d)-(f) for one or more primer extension cycles; (h) contacting the single-stranded primer extension products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded primer extension products, wherein the inside primer comprises a sequence at the 3' end that specifically anneals to the target nucleotide sequence, and wherein the inside primer is nested with respect to the outside primer for the locus of interest; (i) repeating step (h) for one or more (such as about 2-100, e.g., about 5-50, or about 10-30) cycles of PCR amplification to provide amplicons of the target nucleotide sequence; (j) performing next-generation sequencing of the amplicons of the target nucleotide sequence; and (k) detecting a sequence variant associated with the disease in the sequencing reads, thereby providing a diagnosis of the disease. In some embodiments, steps (b)-(i) uses a first set of outside primer and inside primer that specifically anneal to the first strand of the ligated nucleic acid, and a second set of outside primer and inside primer that specifically anneal to the second strand of the ligated nucleic acid. In some embodiments, the outside primer of the first set and the outside primer of the second set comprises a first 5' tag sequence of at least 13 nucleotides long and the inside primer of the first set and the inside primer of the second set comprises a second 5' tag sequence of at least 13 nucleotides long. In some embodiments, the method is further comprises determining an expression level of a gene associated with the disease.

In some embodiments, the method provides information relevant to treatment of a disease, such as a hereditary disease or cancer. In some embodiments, the method is used to aid in treating a disease. In some embodiments, a plurality of sequence variants associated with a disease is detected. In some embodiments, the sequence variants are known sequence variants associated with a hereditary disease or cancer. In some embodiments, the sequence variant is associated with an oncogene, or a tumor suppressor. In some embodiments, the sequence variant is a fusion oncogene.

In some embodiments, the method is used for diagnosis of cancer. In some embodiments, the cancer is lung cancer, breast cancer, or colorectal cancer. In some embodiments, the cancer is non-small cell lung cancer. In some embodiments, the method detects SNV, indel, CNV, gene fusion, and/or abnormal RNA expression associated with the cancer. In some embodiments, the method uses a cell free DNA sample, such as circulating tumor DNA (ctDNA) sample. In some embodiments, the method uses a nucleic acid sample derived from a FFPE sample. In some embodiments, the method detects sequence variants based on both cDNA (or RNA) and gDNA sequences.

In some embodiments, the sequence variant is associated with lung cancer. In some embodiments, the sequence variant is located in ALK, ROS1, RET, and/or Ras. Gene rearrangements involving the ALK, ROS1, and RET genes and which result in fusion oncogenes are well known in the art (see, e.g. Soda et al. Nature 2007 448561-6: Rikova et al. Cell 2007 131:1190-1203; Kohno et al. Nature Medicine 2012 18:375-7; Takouchi et al. Nature Medicine 2012 18:378-81. However, the precise location of the gene rearrangement (e.g. where in the ALK, ROS1, and/or RET gene the rearrangement has occurred), and the identity of the second gene involved in the rearrangement can vary. In the methods described herein, the presence and identity of such a rearrangement can be detected without having to know the location of the rearrangement or the identity of the second gene involved in the gene rearrangement.

Non-limiting examples of applications of the methods described herein include detection of hematological malignancy markers and panels thereof (e.g. including those to detect chromosomal rearrangements in lymphomas and leukemias), detection of sarcoma-related chromosomal rearrangements and panels thereof; detection of IGH/TCR gene rearrangements and panels thereof for lymphoma testing; detection of gene panels associated with lung cancer, breast cancer, or colorectal cancer.

Certain treatments for cancer are particularly effective against tumors comprising certain oncogenes, e.g. a treatment agent which targets the action or expression of a given fusion oncogene can be effective against tumors comprising that fusion oncogene but not against tumors lacking the fusion oncogene. The methods described herein can allow the determination of specific sequences which reveal oncogene status (e.g. mutations and/or chromosomal rearrangements). As described herein, the methods described herein can further allow the determination of specific sequences when the sequence of only one flank is known, e.g. the methods described herein can determine the presence and identity of gene rearrangements involving known oncogenes where the precise location and/or rearrangement partner are not known before the methods described herein are performed.

In some embodiments, the method is used for multiplexed analysis of multiple samples, and/or a panel of genes or loci of interest. In some embodiments, the method is used for sequencing a panel of genes associated with hereditary diseases. In some embodiments, the method is used for sequencing a panel of cancer-associated genes, such as oncogenes or tumor suppressor genes.

Table 1 below shows a non-limiting exemplary list of sequence variants and genes that can be detected using the methods described herein for cancer diagnosis, and exemplary agents that can be used for treatment of the cancer having the sequence variants.

TABLE 1

Exemplary Gene Panels for Cancer Diagnosis and Treatment.

| Gene | Detectable sequence variants ctDNA sample | FFPE sample (e.g., DNA + RNA) | Exemplary agents for treatment |
|---|---|---|---|
| ALK | Gene fusion, SNV, indel, CNV | Gene fusion, SNV, indel, CNV, gene expression | crizotinib, alectinib, ceritinib, brigatinib, lorlatinib |
| BRAF | SNV, INDEL, CNV | SNV, INDEL, CNV | dabrafenib, vemurafenib, sorafenib |
| EGFR | SNV, INDEL, CNV | SNV, INDEL, CNV | gefitinib, erlotinib, icotinib, afatinib, osimertinib, lapatinib, cetruximab, neratinib |
| ERBB2 (HER2) | SNV, INDEL, CNV | SNV, INDEL, CNV | trastuzumab, lapatinib, t-dm1, pertuzumab, afatinib, neratinib |
| HRAS | SNV, INDEL, CNV | SNV, INDEL, CNV | |
| KDR (VEGFR2) | SNV, INDEL, CNV | SNV, INDEL, CNV | aptinib, ramucirumab, cabozantinib, lenvatinib, famitinib, imatinib, anlotinib |
| KIT | SNV, INDEL, CNV | SNV, INDEL, CNV | sunitinib, imatinib, sorafenib, regorafenib, lenvatinib, dasatinib, anlotinib |
| KRAS | SNV, INDEL, CNV | SNV, INDEL, CNV | trametinib, combination therapy of trametinib and dabrafenib |
| MET | SNV, INDEL, CNV | SNV, INDEL, CNV | crizotinib, cabozantinib, capmatinib |
| NRAS | SNV, INDEL, CNV | SNV, INDEL, CNV | |
| NTRK1 | Gene fusion, SNV, indel, CNV | Gene fusion, SNV, indel, CNV, gene expression | larotrectinib, entrectinib, lestaurtinib |
| PDGRFA | SNV, INDEL, CNV | SNV, INDEL, CNV | sunitinib, imatinib, sorafenib, regorafenib, lenvatinib, dasatinib, anlotinib |
| PIK3CA | SNV, INDEL, CNV | SNV, INDEL, CNV | everolimus, temsirolimus, sirolimus |
| PTEN | SNV, INDEL, CNV | SNV, INDEL, CNV | everolimus, temsirolimus, sirolimus |
| RET | Gene fusion, SNV, indel, CNV | Gene fusion, SNV, indel, CNV, gene expression | cabozantinib, regorafenib, lenvatinib, vandetanib |
| ROS1 | Gene fusion, SNV, indel, CNV | Gene fusion, SNV, indel, CNV, gene expression | crizotinib, ceritinib, entrectinib |
| TP53 | SNV, INDEL, CNV | SNV, INDEL, CNV | |

An "individual" refers to a human or animal. In some embodiments, the individual is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the individual is a mammal, such as a human, non-human primate, mouse, rat, dog, cat, horse, or cow. The terms, "individual", "patient" and "subject" are used interchangeably herein. An individual can be one who has been previously diagnosed with or identified as suffering from or having a condition in need of treatment (e.g. cancer) or one or more complications related to such a condition, and optionally, have already undergone treatment for the condition or the one or more complications related to the condition. Alternatively, an individual can also be one who has not been previously diagnosed as having the condition (e.g. cancer) or one or more complications related to the condition. For example, an individual may exhibit one or more risk factors for the condition or one or more complications related to the condition or an individual who does not exhibit risk factors.

In some embodiments, there is provided a method of treating cancer, comprising; detecting, in a tumor sample obtained from an individual in need of treatment for cancer, the presence of one or more sequence variants associated with cancer (such as a fusion oncogene or oncogenic mutation) according to any one of the methods described herein; and administering a cancer treatment which is effective against tumors having any of the detected sequence variant associated with cancer. In some embodiments, there is provide a method of determining whether an individual in need of treatment for cancer will be responsive to a treatment regimen, comprising: detecting, in a tumor sample obtained from the subject, the presence of a sequence variant associated with cancer (such as a fusion oncogene or oncogenic mutation) according to any one of the methods described herein, wherein the subject is determined to be responsive to a treatment regimen if the presence of the sequence variant associated with cancer is detected.

In some embodiments, the method is used in applications wherein the amount of input nucleic acids and/or the quality of the input nucleic acids is low. In some embodiments, the method is used for sequencing clinical samples, such as tumor biopsy samples, e.g., FFPE samples. In some embodiments, the method is used for ancient sample sequencing.

In some embodiments, the method is used for applications wherein the target nucleotide sequences are present at very low levels in the nucleic acid sample. For example, the method is used for microbiota sequencing, and new variant virus genotyping.

In some embodiments, the method is used for identifying clones from a population of cells or animals that have been genetically engineered, for example, by CRISPR genetic editing technology. In some embodiments, the method is used for characterizing an off-target site (e.g., previously known or unknown off-target site) of CRISPR gene editing. In some embodiments, the method is used for assessing engineered cells for cell-based therapy. In some embodiments, the method is for improving the safety of cell-based therapy, wherein the cell administered to an individual is engineered using CRISPR genetic editing technology.

In some embodiments, the method is used for identifying a gene encoding an immune cell receptor. In some embodiments, the immune cell receptor is a T cell receptor. In some embodiments, the method is used for identifying an engineered immune cell receptor, for example, Chimeric Antigen Receptor (CAR) or recombinant T cell receptor (TCR). In some embodiments, the method is used for immune profiling, for example by determining the diversity of TCR sequences, such as CDR3 sequences. In some embodiments, the method is used for identifying TCR sequences that are responsive to a tumor antigen. In some embodiments, the method is used for assessing immune response of an individual to an immunotherapy against a tumor antigen.

IV. Kits and Articles of Manufacture

The present application further provides compositions, kits and articles of manufacture for enhancing and determining nucleotide sequences having one or more loci or interest, or the various applications described herein. The compositions, kits, and articles of manufacture may comprise any one or more of the universal adaptors, nested target-specific primers, universal adaptor primers, sequencing adaptor primers, and sequencing primers described herein.

In some embodiments, there is provided a kit comprising: (a) a universal adaptor, wherein the universal adaptor is an oligonucleotide comprising a ligatable duplex portion at a first end and a non-duplex portion at a second end; (b) a universal adaptor primer, wherein the universal adaptor primer is capable of annealing to a complementary sequence of the non-duplex portion of the universal adaptor; (c) an outside primer; and (d) an inside primer; wherein the inside primer is nested with respect to the outside primer for a locus of interest. In some embodiments, the kit further comprises a DNA polymerase and nucleotides. In some embodiments, the locus of interest is located in any one or more of the genes selected from the group consisting of ALK, BRAF, EGFR, ERBB2, HRAS, KDR, KIT, KRAS, MET, NRAS, NTRK1, PDGFRA, PIK3CA, PTEN, RET, ROS1, and TP53.

In some embodiments, there is provided a kit comprising: (a) a universal adaptor, wherein the universal adaptor is an oligonucleotide comprising a ligatable duplex portion at a first end and a non-duplex portion at a second end; (b) a universal adaptor primer, wherein the universal adaptor primer comprises at the 3' end a sequence that is capable of specific annealing to a complementary sequence of the non-duplex portion of the universal adaptor, and wherein the universal adaptor or the 5' end of the universal adaptor primer comprises a sequence that is identical or complementary to the sequence of a first sequencing primer compatible with an NGS platform; (c) an outside primer; and (d) an inside primer, wherein the inside primer is nested with respect to the outside primer for a locus of interest. In some embodiments, the inside primer comprises a sequence identical or complementary to the sequence of a second sequencing primer compatible with the NGS platform. In some embodiments, the kit further comprises a sequencing adaptor primer, wherein the sequencing adaptor primer comprises at the 3' end a sequence identical to a sequence of the inside primer and at the 5' end a sequence identical or complementary to the sequence of a second sequencing primer compatible with the NGS platform. In some embodiments, the kit further comprises the first sequencing primer and the second sequencing primer. In some embodiments, the kit further comprises a DNA polymerase and nucleotides. In some embodiments, the locus of interest is located in any one or more of the genes selected from the group consisting of ALK, BRAF, EGFR, ERBB2, HRAS, KDR, KIT, KRAS, MET, NRAS, NTRK1, PDGFRA, PIK3CA, PTEN, RET, ROS1, and TP53.

In some embodiments, the kit is for enriching a target nucleotide sequence having the locus of interest. In some embodiments, the kit is for preparing a sequencing library. In some embodiments, the kit is for determining a target nucleotide sequence having a locus of interest. In some embodiments, the kit is for detecting a sequence variant having a locus of interest. In some embodiments, the kit is for diagnosing a disease or condition. In some embodiments, the kit is for treating a disease or condition. In some embodiments, the kit is used for diagnosis of a cancer, such as lung cancer, breast cancer, or colorectal cancer. In some embodiments, the kit is used for treating a cancer, such as lung cancer, breast cancer, or colorectal cancer.

In some embodiments, the kit comprises a first set of outside primer and inside primer that can specifically anneal to a first strand of a nucleic acid template comprising the locus of interest, and a second set of outside primer and inside primer that can specifically anneal to the complementary strand of the first strand of the nucleic acid template. In some embodiments, the outside primer of the first set and the outside primer of the second set comprises a first 5' tag sequence of at least about 13 nucleotides long, and wherein the inside primer of the first set and the inside primer of the second set comprises a second 5' tag sequence of at least about 13 nucleotides long. In some embodiments, the kit comprises a plurality (such as at least about any one of 2, 5, 10, 20, 50, 100, 200, 500, 1000, 2000, 5000, 10000, 20000 or more) of sets of outside primer and inside primer. In some embodiments, the plurality of sets of outside primer and inside primer can be used to enrich or determine target sequences having a plurality of different loci of interest. In some embodiments, the plurality of sets of outside primer and inside primer can be used to enrich or determine target sequences having at least about any one of 2, 5, 10, 20, 50, 100, 200, 500, 1000, 2000, 5000 or more different loci of interest. In some embodiments, the plurality of sets of outside primer and inside primer can be used to enrich or determine target sequences having about 2-200, such as about any one of 2-100, 2-50, 5-100, 10-100, or 50-150 different loci of interest. In some embodiments, the plurality of sets of outside primer and inside primer can be used to enrich or determine target sequences having about 100-5000, such as about any one of 100-500, 500-1000, 100-2000, 1000-2000, 2000-3000, or 3000-5000 different loci of interest. In some embodiments, the kit is custom-designed for the loci of interest according to users' need.

In some embodiments, the kit further comprises reagents and enzymes for preparing a nucleic acid sample. In some embodiments, the kit comprises reagents for preparing a nucleic acid sample from a blood sample. In some embodiments, the kit comprises reagents for preparing a nucleic acid sample from a tumor biopsy sample. In some embodiments, the kit comprises reagents for preparing a nucleic acid sample from a FFPE sample. In some embodiments, the kit comprises reagents for preparing a nucleic acid sample from a cell free DNA sample, such as circulating tumor DNA sample. In some embodiments, the kit provides enough reagents, primers and adaptors for preparing at least any of 1, 2, 4, 10, 15, 20, 100, 500, 1000, or more sequencing libraries.

In some embodiments, the kit further comprises a pharmaceutical composition comprising an agent that is suitable for treating a cancer based on the detection of certain sequence variant. For example, see Table 1.

The kits may contain one or more additional components, such as containers, buffers, reagents, cofactors, or additional agents, such as denaturing agent. The kit components may be packaged together and the package may contain or be accompanied by instructions for using the kit for any one of the methods described herein. In some embodiments, the kit further comprises instructions for diagnosing and/or treating a disease or condition, such as cancer.

It will be appreciated by persons skilled in the art the numerous variations, combinations and/or modifications may be made to the invention as shown without departing from the spirit of the inventions as broadly described.

EXAMPLES

The examples below are intended to be purely exemplary of the invention and should therefore not be considered to limit the invention in any way. The following examples and detailed description are offered by way of illustration and not by way of limitation.

Example 1: Highly Efficient Target Enrichment and Sequencing Methods for Sensitive Detection of Cancer-Associated Sequence Variants This example describes an exemplary method of detecting cancer-associated sequence variants. Eight universal adaptors each having a sample barcode were used to prepare a multiplexed sequencing library. Target sequences having a total of 246 loci were enriched from each nucleic acid sample. Two different amounts of starting input human DNA samples, namely 5 ng and 50 ng, were used. KAPA enzymes were used as an example. FIG. 1 shows a schematic of the method.

Primer Preparation

Each universal adaptor was prepared by annealing one Top Oligo (first strand) and one matching Bottom Oligo (second strand) as shown in Table 2 below. Also shown in Table 2 are universal adaptor primer, sequencing primers and exemplary pool of outside and inside primers for multiple loci of interest in TP53 gene.

Universal adaptors with or without blocking moieties can be used. For example, a universal adaptor with a blocking moiety (e.g., flap nucleotides having phosphorothioate modifications) in the second strand can be prepared by annealing Y-TOP-1 with Y-BOT-01. A corresponding universal adaptor without a blocking moiety in the second strand can be prepared by annealing Y-TOP-1 with Y-BOT-01-unblocked. The efficiencies of library construction using blocked and unblocked universal adaptors are determined.

TABLE 2

Exemplary primers for Target Enrichment.

| Oligo name | SEQ ID NO | Sequence |
|---|---|---|
| Top Oligos (5'-3') for construction of universal adaptor | | |
| Y-TOP-01 | 1 | AATGATACGGCGACCACCGAGATCTACACTCTTTCCCTACACGACGCTCTTCCGATCTNN NNNNNNYYTAGATCGC*T |
| Y-TOP-02 | 2 | AATGATACGGCGACCACCGAGATCTACACTCTTTCCCTACACGACGCTCTTCCGATCTNN NNNNNNYYCTCTCTAT*T |

TABLE 2-continued

Exemplary primers for Target Enrichment.

| Oligo name | SEQ ID NO | Sequence |
|---|---|---|
| Y-TOP-03 | 3 | AATGATACGGCGACCACCGAGATCTACACTCTTTCCCTACACGACGCTCTTCCGATCTNN NNNNNNYYTATCCTCT*T |
| Y-TOP-04 | 4 | AATGATACGGCGACCACCGAGATCTACACTCTTTCCCTACACGACGCTCTTCCGATCTNN NNNNNNYYAGAGTAGA*T |
| Y-TOP-05 | 5 | AATGATACGGCGACCACCGAGATCTACACTCTTTCCCTACACGACGCTCTTCCGATCTNN NNNNNNYYGTAAGGAG*T |
| Y-TOP-06 | 6 | AATGATACGGCGACCACCGAGATCTACACTCTTTCCCTACACGACGCTCTTCCGATCTNN NNNNNNYYACTGCATA*T |
| Y-TOP-07 | 7 | AATGATACGGCGACCACCGAGATCTACACTCTTTCCCTACACGACGCTCTTCCGATCTNN NNNNNNYYAAGGAGTA*T |
| Y-TOP-08 | 8 | AATGATACGGCGACCACCGAGATCTACACTCTTTCCCTACACGACGCTCTTCCGATCTNN NNNNNNYYCTAAGCCT*T |

Bottom Oligos (5'-3') for construction of universal adaptor
*indicates a phosphorothioate bond modification
/5Phos/ indicates a 5' phosphorylation

| Y-BOT-01 | 9 | /5Phos/GCGATCTA*Y*Y |
| Y-BOT-01-unblocked | 10 | /5Phos/GCGATCTAYY |
| Y-BOT-02 | 11 | /5Phos/ATAGAGAG*Y*Y |
| Y-BOT-03 | 12 | /5Phos/AGAGGATA*Y*Y |
| Y-BOT-04 | 13 | /5Phos/TCTACTCT*Y*Y |
| Y-BOT-05 | 14 | /5Phos/CTCCTTAC*Y*Y |
| Y-BOT-06 | 15 | /5Phos/TATGCAGT*Y*Y |
| Y-BOT-07 | 16 | /5Phos/TACTCCTT*Y*Y |
| Y-BOT-08 | 17 | /5Phos/AGGCTTAG*Y*Y |

Universal adaptor primer (5'-3')

| P5 | 18 | AATGATACGGCGACCACCGAGATCTA |

Sequencing primer (5'-3')

| I7-01 | 19 | CAAGCAGAAGACGGCATACGAGATTCGCCTTAGTGACTGGAGTTCAGACGTGT |
| I7-02 | 20 | CAAGCAGAAGACGGCATACGAGATCTAGTACGGTGACTGGAGTTCAGACGTGT |
| I7-03 | 21 | CAAGCAGAAGACGGCATACGAGATTTCTGCCTGTGACTGGAGTTCAGACGTGT |
| I7-04 | 22 | CAAGCAGAAGACGGCATACGAGATGCTCAGGAGTGACTGGAGTTCAGACGTGT |
| I7-05 | 23 | CAAGCAGAAGACGGCATACGAGATAGGAGTCCGTGACTGGAGTTCAGACGTGT |
| I7-06 | 24 | CAAGCAGAAGACGGCATACGAGATCATGCCTAGTGACTGGAGTTCAGACGTGT |
| I7-07 | 25 | CAAGCAGAAGACGGCATACGAGATGTAGAGAGGTGACTGGAGTTCAGACGTGT |
| I7-08 | 26 | CAAGCAGAAGACGGCATACGAGATCCTCTCTGGTGACTGGAGTTCAGACGTGT |

Exemplary outside primer for TP53 (5'-3')

| TP53.002.am1 | 27 | AAGACGTGTGCTCTTCCGAACGCTTCCCACAGGTCTCTGCTAG |
| TP53.002.ap1 | 28 | AAGACGTGTGCTCTTCCGAACCCCACTTTTCCTCTTGCAG |
| TP53.003.am1 | 29 | AAGACGTGTGCTCTTCCGAATCCAGGTCCCCAGCCCAACC |
| TP53.003.ap1 | 30 | AAGACGTGTGCTCTTCCGAAATTCCATGGGACTGACTTTC |
| TP53.004.am1 | 31 | AAGACGTGTGCTCTTCCGAAATACGGCCAGGCATTGAAGTC |
| TP53.004.ap1 | 32 | AAGACGTGTGCTCTTCCGAACCTCTGACTGCTCTTTTCAC |
| TP53.004.bm1 | 33 | AAGACGTGTGCTCTTCCGAAGGGAAGGGACAGAAGATGAC |
| TP53.004.bp1 | 34 | AAGACGTGTGCTCTTCCGAAAAGCTCCCAGAATGCCAGAGG |
| TP53.005.am1 | 35 | AAGACGTGTGCTCTTCCGAAGCCCTGTCGTCTCTCCAGCC |
| TP53.005.ap1 | 36 | AAGACGTGTGCTCTTCCGAATGCCCTGACTTTCAACTCTG |
| TP53.005.bm1 | 37 | AAGACGTGTGCTCTTCCGAATGCTGTGACTGCTTGTAGATG |
| TP53.005.bp1 | 38 | AAGACGTGTGCTCTTCCGAACCCTGTGCAGCTGTGGGTTG |
| TP53.006.am1 | 39 | AAGACGTGTGCTCTTCCGAACCTTAACCCCTCCTCCCAGAG |
| TP53.006.ap1 | 40 | AAGACGTGTGCTCTTCCGAAGGTCCCCAGGCCTCTGATTC |
| TP53.007.am1 | 41 | AAGACGTGTGCTCTTCCGAAGCCCAGGGGTCAGAGGCAAG |

TABLE 2-continued

Exemplary primers for Target Enrichment.

| Oligo name | SEQ ID NO | Sequence |
|---|---|---|
| TP53.007.ap1 | 42 | AAGACGTGTGCTCTTCCGAATTGCCACAGGTCTCCCCAAGGC |
| TP53.008.am1 | 43 | AAGACGTGTGCTCTTCCGAACTCCACCGCTTCTTGTCCTG |
| TP53.008.ap1 | 44 | AAGACGTGTGCTCTTCCGAATACTGCCTCTTGCTTCTCTTTTC |
| TP53.009.am1 | 45 | AAGACGTGTGCTCTTCCGAAACGGCATTTTGAGTGTTAGAC |
| TP53.009.ap1 | 46 | AAGACGTGTGCTCTTCCGAACTCAGATTCACTTTTATCACCTTTC |
| TP53.010.am1 | 47 | AAGACGTGTGCTCTTCCGAAATGAAGGCAGGATGAGAATGG |
| TP53.010.ap1 | 48 | AAGACGTGTGCTCTTCCGAAGAACCATCTTTTAACTCAGGTAC |
| TP53.011.am1 | 49 | AAGACGTGTGCTCTTCCGAATGTCAGTGGGGAACAAGAAG |
| TP53.011.ap1 | 50 | AAGACGTGTGCTCTTCCGAACATGTGATGTCATCTCTCCTC |

Exemplary inside primer for TP53 (5'-3')

| Oligo name | SEQ ID NO | Sequence |
|---|---|---|
| TP53.002.am2 | 51 | GTGACTGGAGTTCAGACGTGTGCTCTTCCGATCTTGCTAGGGGCTGGGGTTGG |
| TP53.002.ap2 | 52 | GTGACTGGAGTTCAGACGTGTGCTCTTCCGATCTCCAGACTGCCTTCCGGGTCAC |
| TP53.003.am2 | 53 | GTGACTGGAGTTCAGACGTGTGCTCTTCCGATCTCCCCAGCCCAACCCTTGTCC |
| TP53.003.ap2 | 54 | GTGACTGGAGTTCAGACGTGTGCTCTTCCGATCTACTGACTTTCTGCTCTTGTC |
| TP53.004.am2 | 55 | GTGACTGGAGTTCAGACGTGTGCTCTTCCGATCTCAGGCATTGAAGTCTCATGG |
| TP53.004.ap2 | 56 | GTGACTGGAGTTCAGACGTGTGCTCTTCCGATCTTGACTGCTCTTTTCACCCATC |
| TP53.004.bm2 | 57 | GTGACTGGAGTTCAGACGTGTGCTCTTCCGATCTAAGATGACAGGGGCCAGGAG |
| TP53.004.bp2 | 58 | GTGACTGGAGTTCAGACGTGTGCTCTTCCGATCTCCCCGTGGCCCCTGCACCAG |
| TP53.005.am2 | 59 | GTGACTGGAGTTCAGACGTGTGCTCTTCCGATCTTGTCGTCTCTCCAGCCCCAGC |
| TP53.005.ap2 | 60 | GTGACTGGAGTTCAGACGTGTGCTCTTCCGATCTACTTTCAACTCTGTCTCCTTCCTC |
| TP53.005.bm2 | 61 | GTGACTGGAGTTCAGACGTGTGCTCTTCCGATCTTGCTTGTAGATGGCCATGGC |
| TP53.005.bp2 | 62 | GTGACTGGAGTTCAGACGTGTGCTCTTCCGATCTCCTGTGCAGCTGTGGGTTGATTCC |
| TP53.006.am2 | 63 | GTGACTGGAGTTCAGACGTGTGCTCTTCCGATCTCTCCCAGAGACCCCAGTTGC |
| TP53.006.ap2 | 64 | GTGACTGGAGTTCAGACGTGTGCTCTTCCGATCTCCCAGGCCTCTGATTCCTCAC |
| TP53.007.am2 | 65 | GTGACTGGAGTTCAGACGTGTGCTCTTCCGATCTGGGTCAGAGGCAAGCAGAGG |
| TP53.007.ap2 | 66 | GTGACTGGAGTTCAGACGTGTGCTCTTCCGATCTGCCTCATCTTGGGCCTGTGTTATC |
| TP53.008.am2 | 67 | GTGACTGGAGTTCAGACGTGTGCTCTTCCGATCTCCGCTTCTTGTCCTGCTTGC |
| TP53.008.ap2 | 68 | GTGACTGGAGTTCAGACGTGTGCTCTTCCGATCTTGCCTCTTGCTTCTCTTTTCCTATCC |
| TP53.009.am2 | 69 | GTGACTGGAGTTCAGACGTGTGCTCTTCCGATCTGGCATTTTGAGTGTTAGACTGGAAAC |
| TP53.009.ap2 | 70 | GTGACTGGAGTTCAGACGTGTGCTCTTCCGATCTATTCACTTTTATCACCTTTCCTTGCC |
| TP53.010.am2 | 71 | GTGACTGGAGTTCAGACGTGTGCTCTTCCGATCTTGAAGGCAGGATGAGAATGGAATCC |
| TP53.010.ap2 | 72 | GTGACTGGAGTTCAGACGTGTGCTCTTCCGATCTGGTACTGTGTATATACTTACTTCTCC |
| TP53.011.am2 | 73 | GTGACTGGAGTTCAGACGTGTGCTCTTCCGATCTGTGGGGAACAAGAAGTGGAG |
| TP53.011.ap2 | 74 | GTGACTGGAGTTCAGACGTGTGCTCTTCCGATCTGTCATCTCTCCTCCCTGCTTC |

Step 1. Fragmentation, End Repair, A-Tailing and Ligation in One Tube

1) Fragmentation: On ice, a fragmentation master mix was prepared by mixing 2.5 µL of Fragmentation Buffer (10×), 5.0 µL of Frag Enzyme (KAPA Bio) and DNA sample, and the master mix was adjusted to 17.5 µL using nuclease-free water. The reaction was incubated at 37° C. for 15 min; 4° C. hold 2) End Repair and A-tailing: On ice, a master mix was prepared by mixing 3.5 µL of End Repair & A-Tailing Buffer, 1.5 µL of End Repair & A-Tailing Enzyme Mix. 5.0 µL of this master mix was added to the above fragmentation reaction, which was vortexed gently and spun down briefly. The reaction was immediately returned to the thermocycler to perform end repair and A-tailing by incubation at 37° C. for 15 min, 65° C. for 15 min, followed by 4° C. hold, and proceeded immediately to the next step.

3) Adaptor Ligation: On ice, a master mix was prepared by mixing 15.0 µL of Ligation Buffer and 5.0 µL of DNA Ligase. 5.0 µL of 10 µM universal adaptor (with sample barcode) was added to the above end repair and A-tailing reaction, which was gently mixed by pipetting 5 times, then 20.0 µL of the master mix was added to each of the above reaction from 2), vortexed gently and spun down briefly, followed by incubation at 16° C. for 30 min, 30° C. for 30 min, and 12° C. hold.

4) Post-ligation cleanup (performed in pre-PCR area): 1.5× volume (i.e. 82.5 µL) AMPURE® beads was used according to the manufacturer's protocol to clean up the ligation reaction, which was eluted in a final 20 µL of 1× Tris-Buffer. The beads were carried into next step (Primer extension).

Step 2. Target Enrichment 1—Primer Extension

A primer extension master mix was prepared by mixing 4.4 µL of nuclease-free water, 3.0 µL of buffer for Taq Polymerase (10×, magnesium free, Thermo Fisher), 0.6 µL of dNTP mix (10 mM), 1.2 µL of Mg2+ (50 mM), 0.3 µL of PLATINUM™ Taq polymerase (5 U/µL), and 0.5 µL of outside primer pool (50 µM). 20.00 µL, of post-ligation cleanup sample was added to 30.00 µL, of the primer extension master mix. The resulting mixture was incubated in a thermocycler to carry out primer extension reaction, using the program as follows: 95° C. for 5 min; 20 cycles of [ramping up to 95° C. at a speed of +0.2° C./sec; 95° C. for 10 sec; ramping down to 60° C. at a speed of –0.2° C./sec; 60° C. for 10 min;]; and 4° C. hold.

The primer extension product was cleaned up, in a post-PCR area, using 1.2× volume (36.0 µL) of AMPURE® beads according to the manufacturer's protocol and eluted in 20 µL of 1× Tris-Buffer.

Step 3. Target Enrichment 2—PCR

A PCR master mix was prepared by mixing 1.9 µL of nuclease-free water, 3.0 µL of buffer for Taq Polymerase (10×, magnesium free, Thermo Fisher), 0.6 µL of dNTP mix (10 mM), 1.2 µL of Mg2+ (50 mM), 0.3 µL of PLATINUM™ Taq polymerase (5 U/µL), 1.0 µL of P5 primer (10 µM), and 1.0 µL of inside primer pool (50 µM). 20.00 µL of post-primer extension cleanup sample was added to 9.0 µL of the PCR master mix, and 1.0 µL of each corresponding 17 primer (with barcode, 10 µM) was added to each sample. The resulting mixture was incubated in a thermocycler to carry out polymerase chain reaction using the following program: 95° C. for 5 min; 15 cycles of [95° C. for 30 sec; 60° C. for 5 min]; and 4° C. hold.

The PCR product was cleaned up, in a post-PCR area, using 1.2× volume (36.0 µL) of AMPURE® beads according to the manufacturer's protocol and eluted in 20 µL of 1× Tris-Buffer.

Step 4. Sequencing.

The cleaned up PCR product was quantified using KAPA qPCR kit, and sequenced using the Illumina sequencing system according to standard protocols.

Step 5. Data Analysis.

Sequencing data in BCL format was converted to FASTQ format using bcl2fq package, with sample de-multiplexing using the 17 barcodes. The initially processed FASTQ files were further de-multiplexed based on the adaptor barcode, which was integrated in Read 1 with a customized script, and adaptor sequences were trimmed. Dual de-multiplexed FASTQ files were mapped to human genome (hg19) using BWA-MEM. Amplicon sequences derived from the same nucleic acid template were identified based on molecular barcode sequences and consolidated. Sequencing specifications were calculated using BED tools, target BED file and custom scripts. SNV and Indel variants were called using unique molecular index-aware scripts.

Results

Figure 4A:
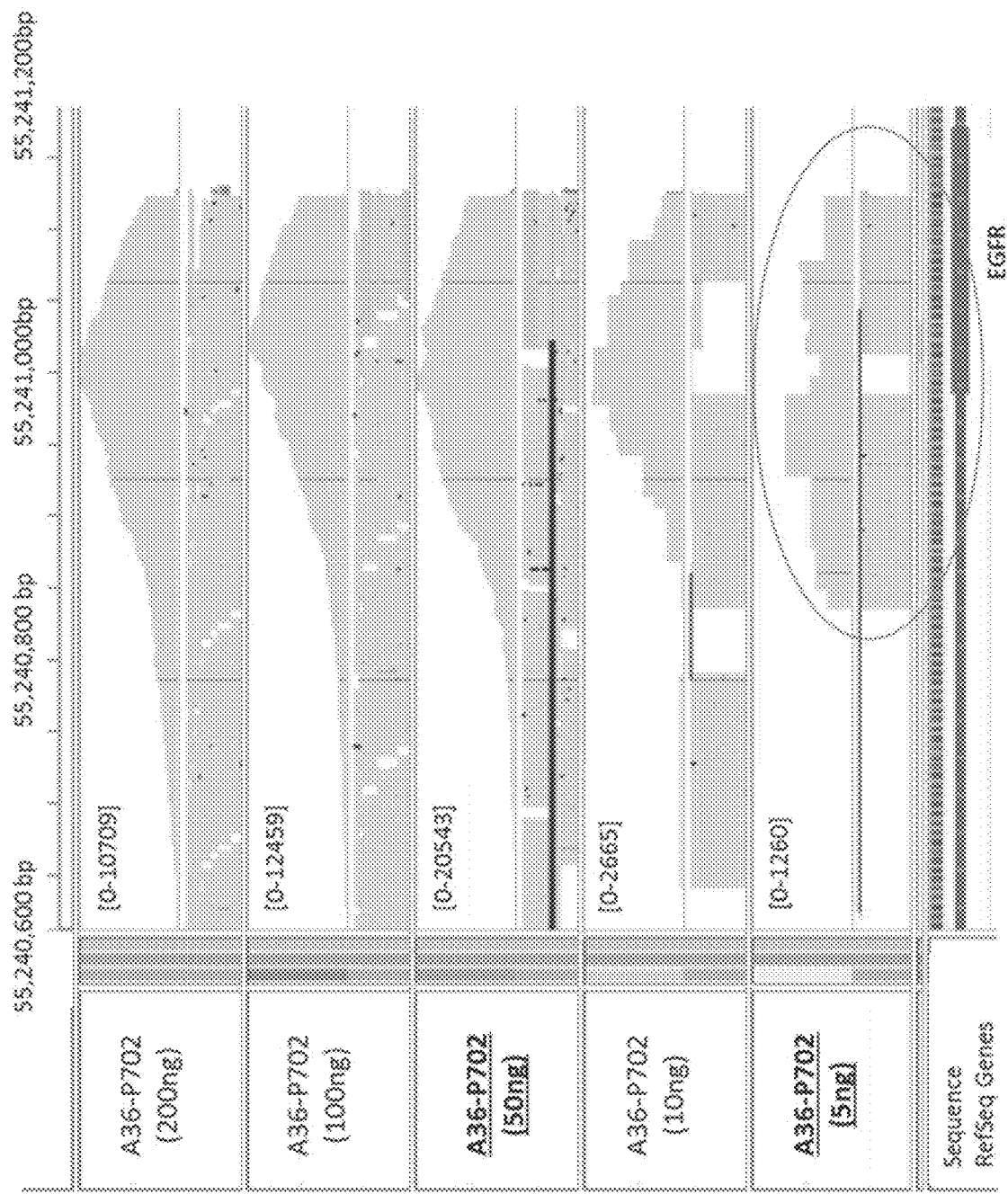
FIG. 4A shows mapped reads having an EGFR locus using previously published AMP method for target enrichment.
Figure 4B:
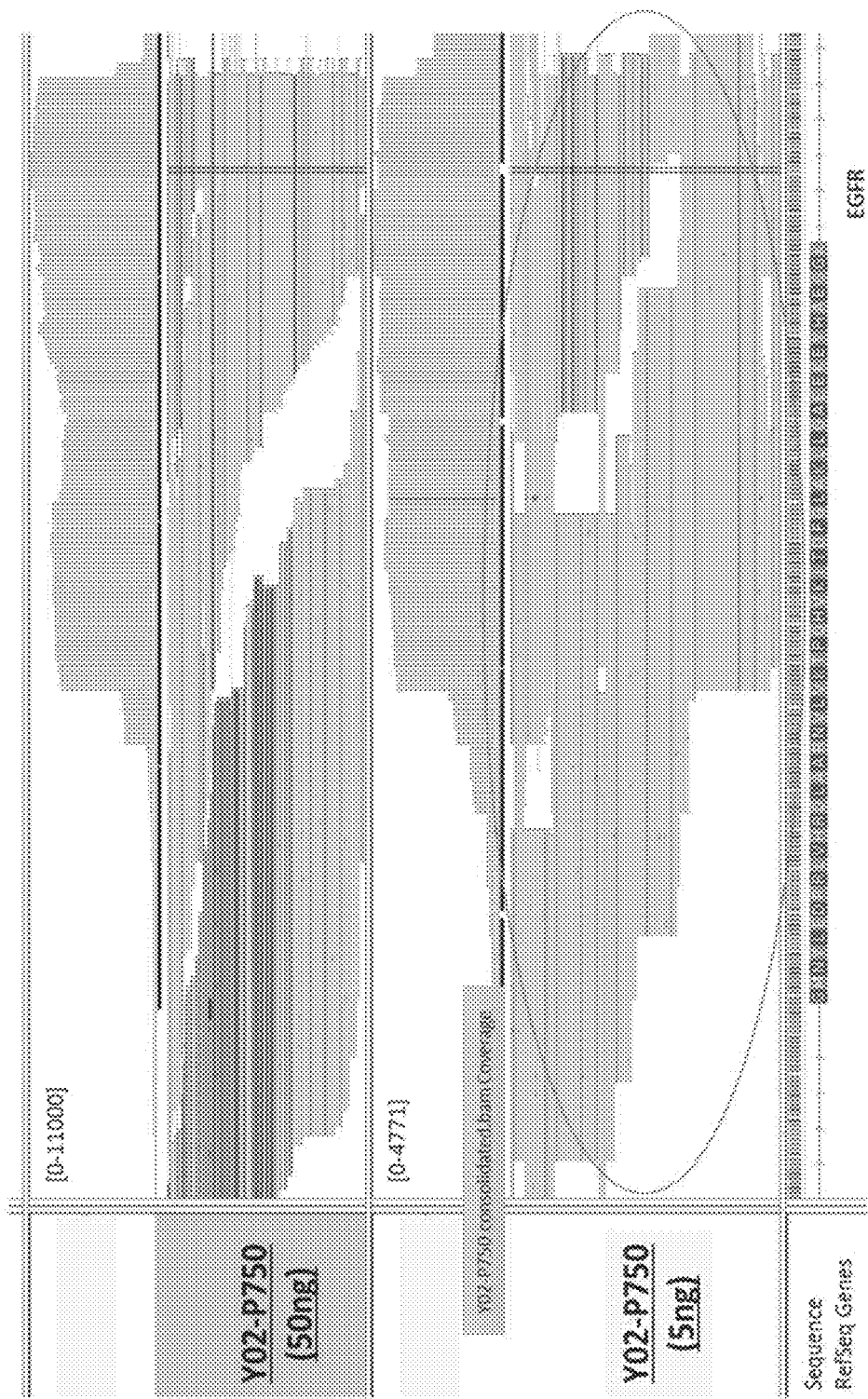
FIG. 4B shows mapped reads having an EGFR locus using the method described in Example 1 of the present application.

FIGS. 4A-4B are views of mapped reads from the IGV software showing read pileups having a locus of interest within the EGFR gene. FIG. 4A is a replicate of FIG. S5 from Zheng Z. et al. *Nature Medicine* 20: 1479-1484 (2014), showing results using a method named "Anchored Multiplex PCR" or "AMP". Using 5 ng of input DNA in the AMP method, the mapped reads have blocky read pileup around the locus of interest, indicating poor library complexity and thus low library construction efficiency using low amount of input DNA.

In contrast, FIG. 4B shows results using the method described in this example. Using the same amount of input DNA as the AMP method (e.g., compare mapped reads in the 5 ng panels as highlighted in circles of FIG. 4A and FIG. 4B), the present method yielded more smooth read pileup, indicating a higher library complexity and higher library construction efficiency using low amount of input DNA.

Figure 5A:
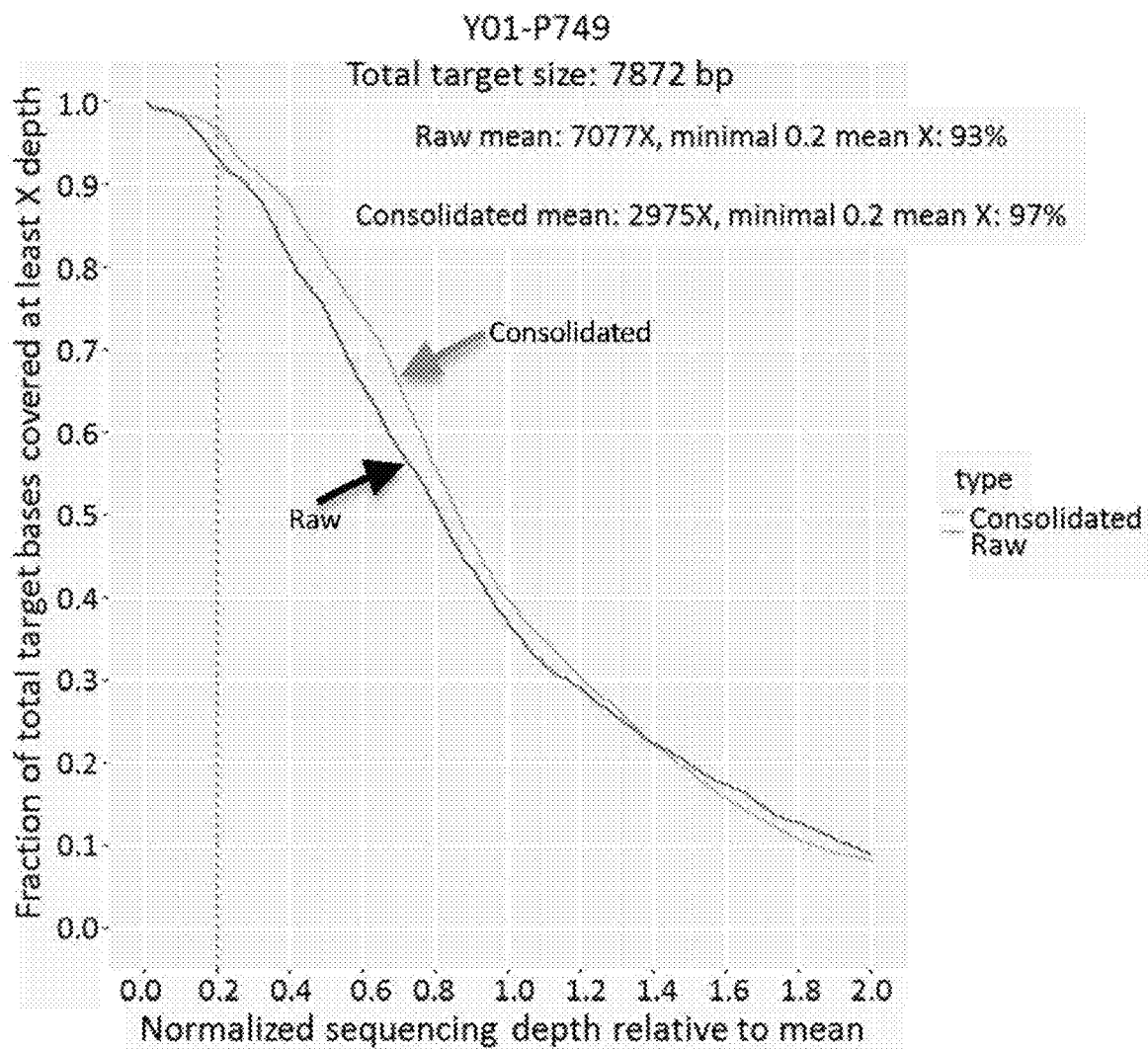
FIG. 5A shows sequence coverage and sequence depth over the entire length of the EGFR locus using the method described in Example 1 and 50 ng of input DNA.
Figure 5B:
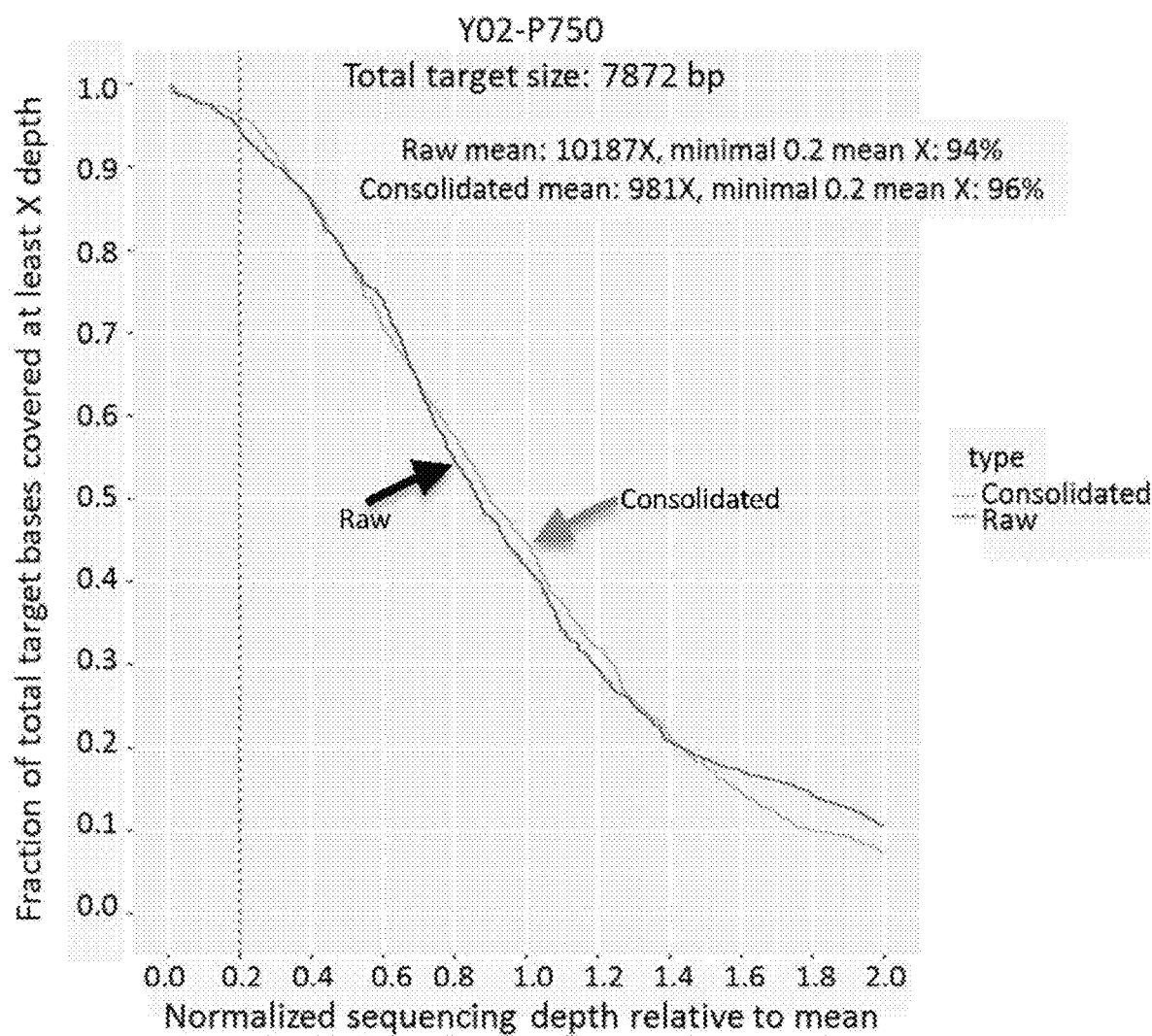
FIG. 5B shows sequence coverage and sequence depth over the entire length of the EGFR locus using the method described in Example 1 and 5 ng of input DNA.
Figure 6A:
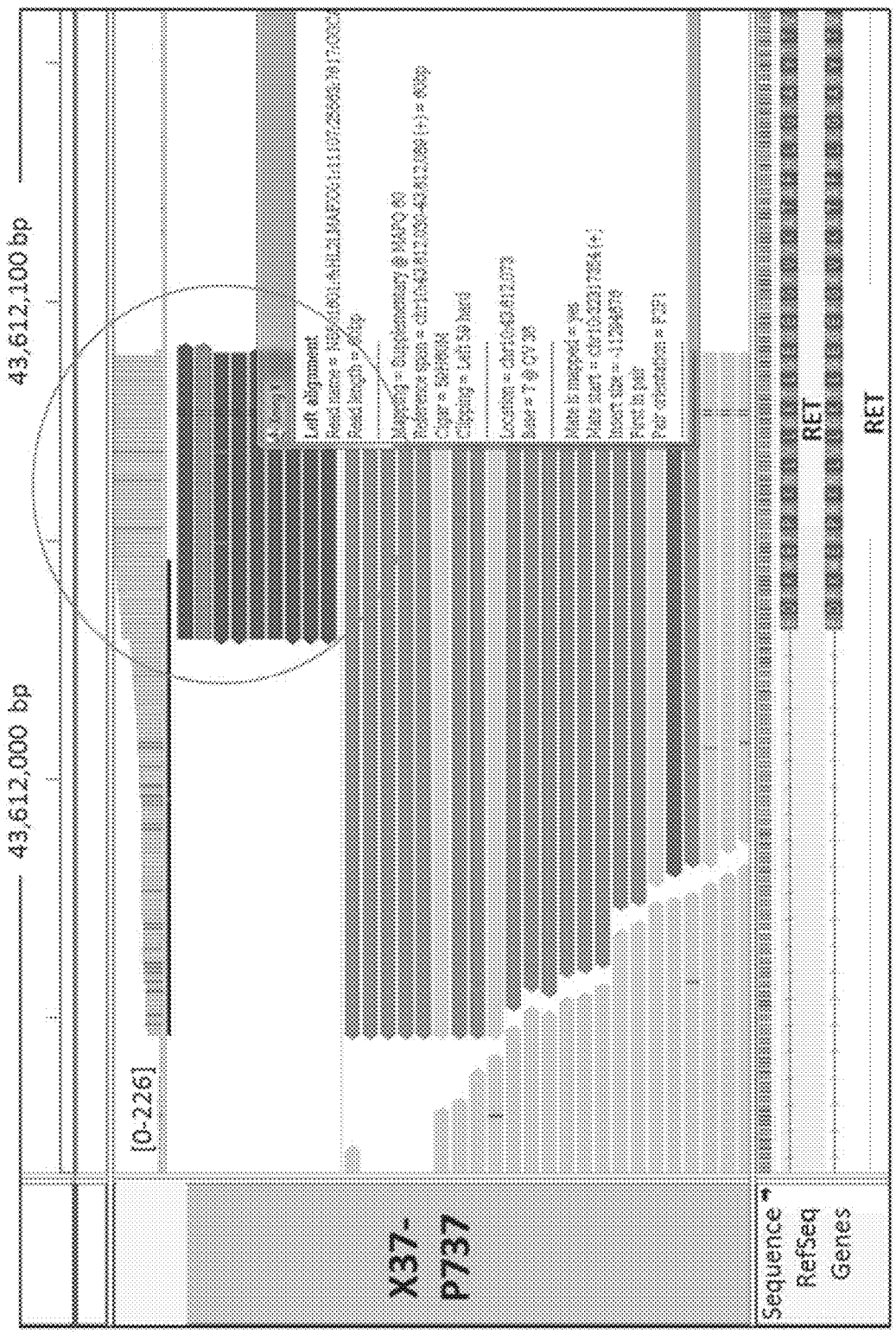
FIGS. 6A-6B show RNA-based detection of in-frame gene fusion between KIF5B exon 15 c.1723 and RET exon 12 c. 2138.
Figure 6B:
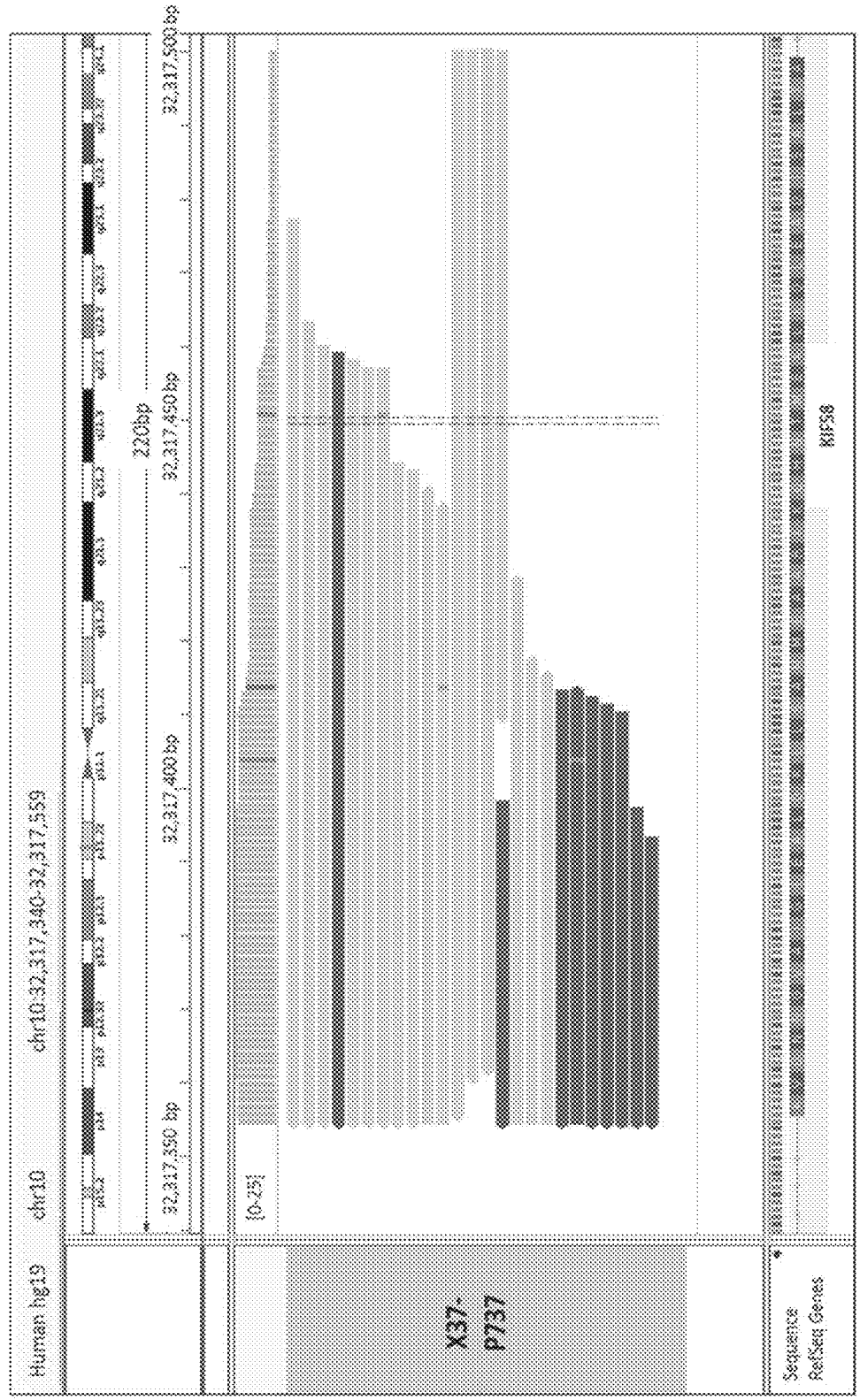
Figure 6C:
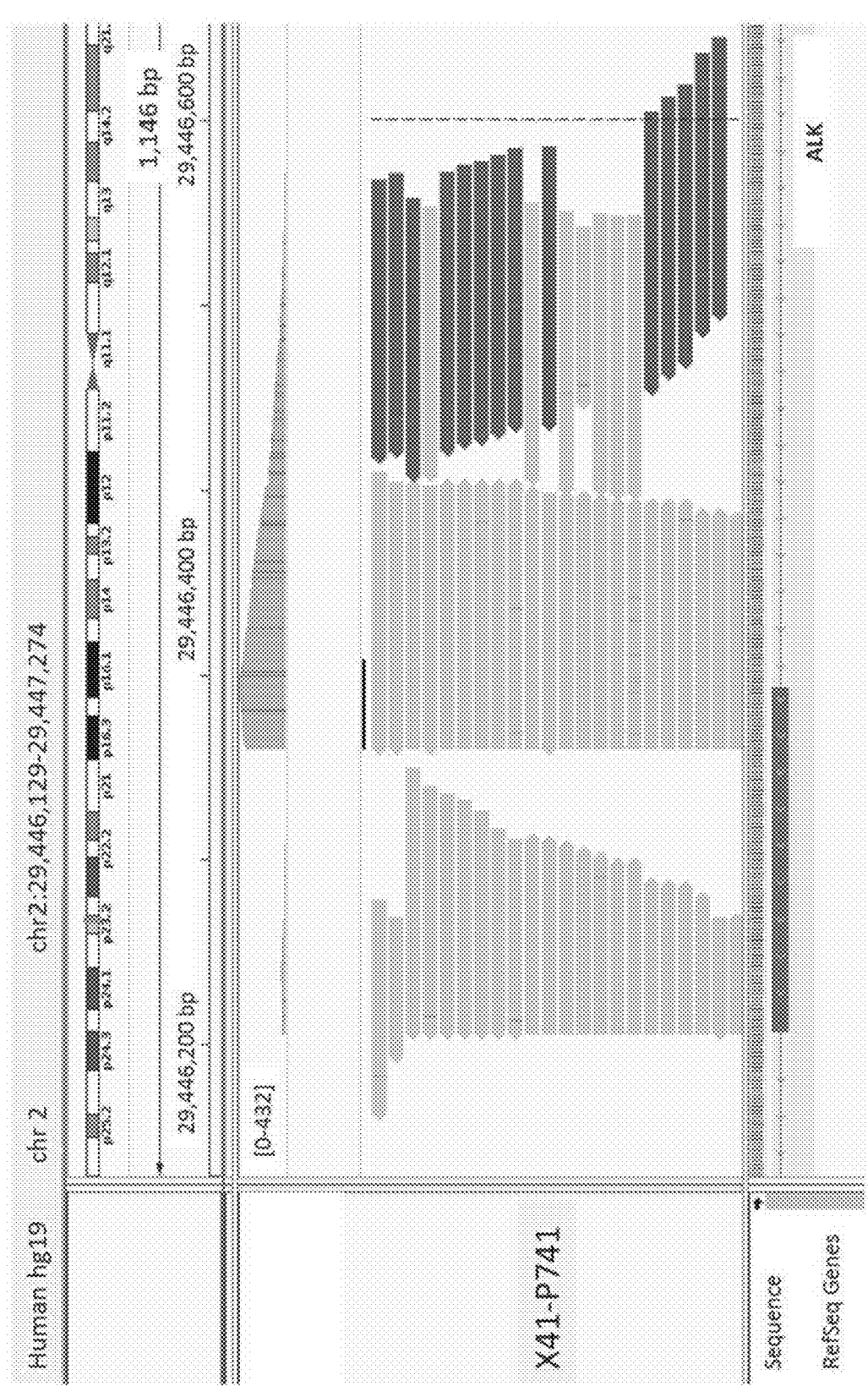
FIGS. 6C-6D show RNA-based detection of gene fusion between EML4 exon 4 c. 468 and ALK exon 20 c. 3173.
Figure 6D:
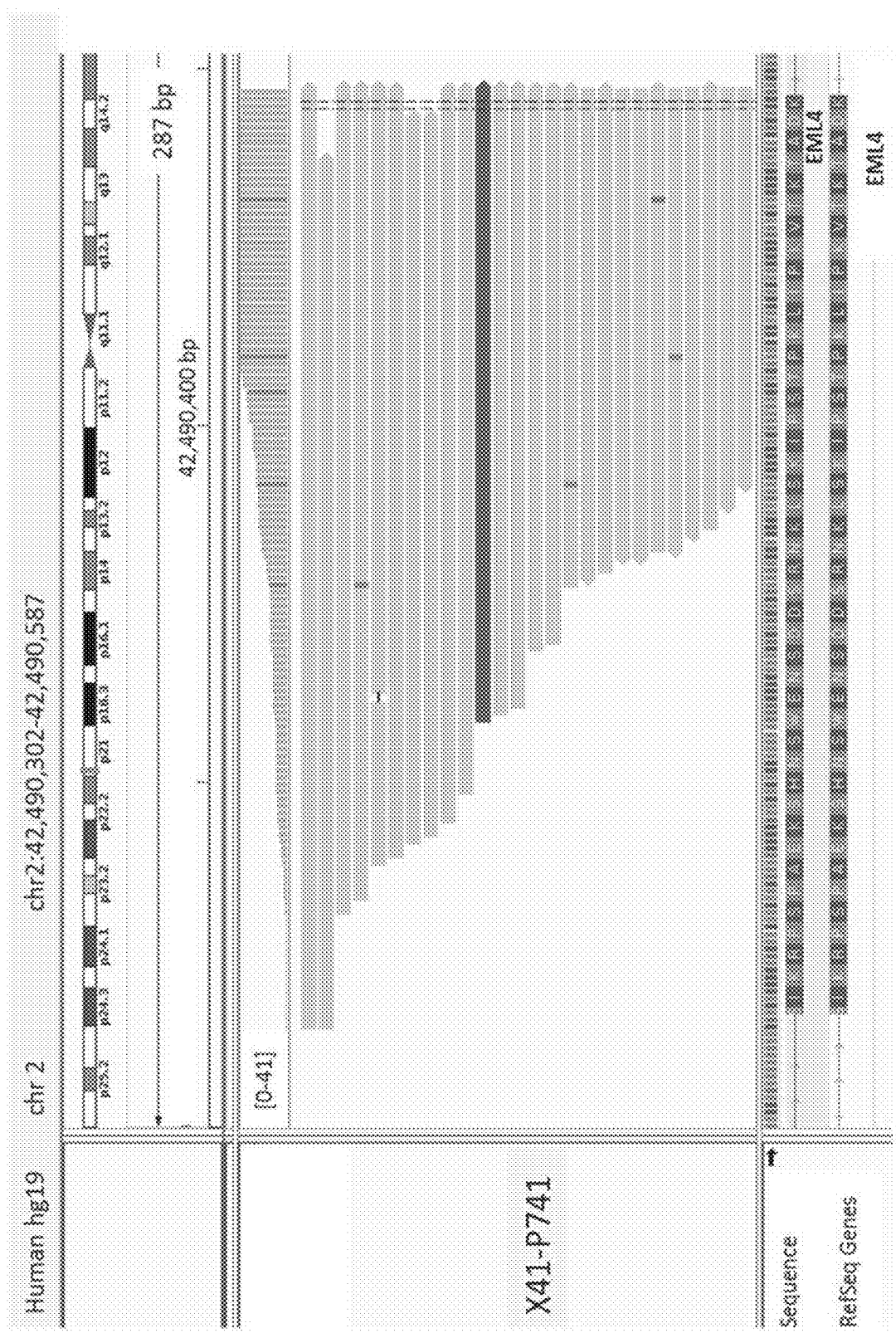
Figure 6E:
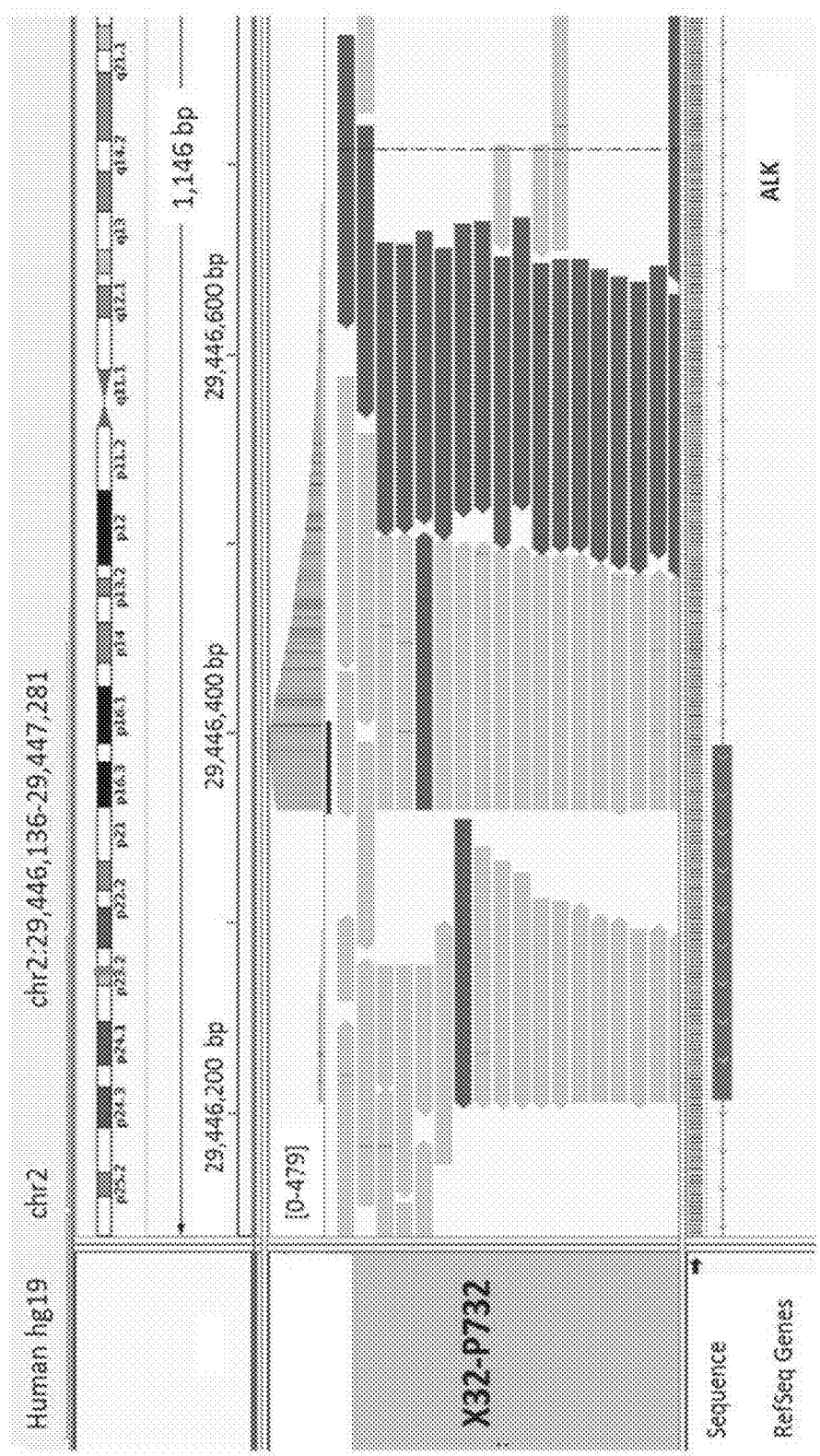
FIGS. 6E-6F show RNA-based detection of in-frame gene fusion between EML4 exon 17 c. 1880 and ALK exon 20 c. 3173.
Figure 6F:
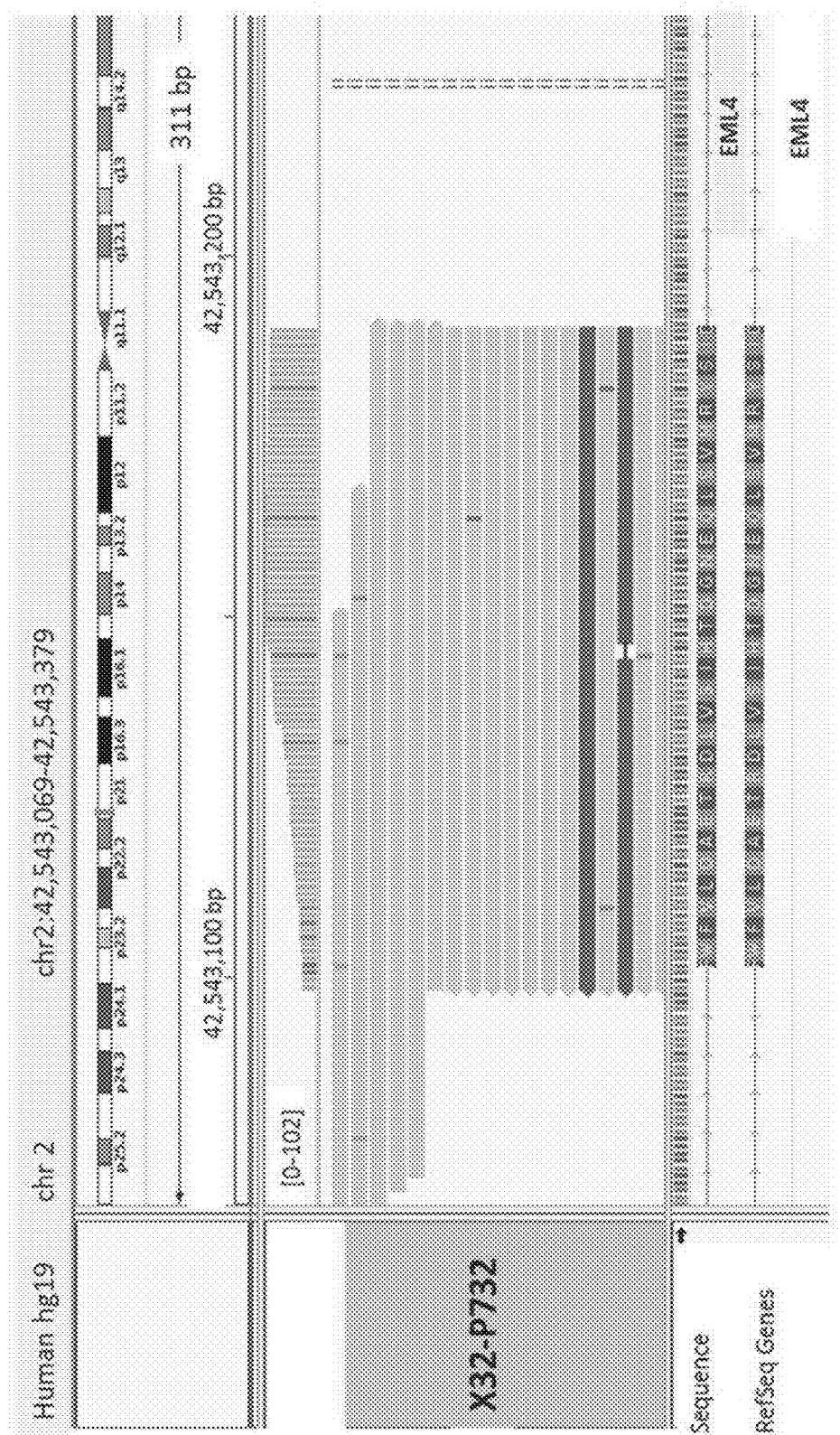

FIG. 5A and FIG. 5B show overall panel coverage statistics for two sequencing libraries, Y01-P749 (with 50 ng input DNA), and Y02-P750 (with 5 ng input DNA) respectively. The raw data represents all sequencing reads mapped to the target. The consolidated data represents consolidated sequencing reads after identification and merging of sequencing reads that belong to the same nucleic acid templates. The results demonstrate unbiased enrichment of target nucleotide sequences using both 50 ng and 5 ng input DNA in the method described herein.

Example 2: Simultaneous RNA-Based Detection of Gene Fusion and gDNA-Based Detection of Mutations in a Single Reaction This example describes detection of sequence variants from RNA and gDNA in a single sequencing reaction.

Step 1. RNA Purification from FFPE Sample.

Briefly, first FFPE samples were subjected to RNA extraction using the FORMAPURE® FFPE kit. RNA concentration was determined using QUBIT® RNA kit. A total of about 15 ng of total nucleic acids, including 10 ng extracted RNA, and 5 ng gDNA, was used in the next step.

Step 2. Double Strand cDNA Synthesis

1) RNA denaturation: Each RNA sample was adjusted to 11.0 µL using DEPC-treated water to a PCR tube, followed by addition of 1.0 µL of random hexamer (300 ng/µL) and 1.0 μL of dNTP (10 mM). The mixture was mixed by pipetting 5 times, and RNA denaturation was performed by incubation at 65° C. for 5 min (with heat lid on at 103° C.). After the incubation, the sample plate was immediately chilled on ice-water for at least 1 min, briefly centrifuged, and placed back on ice.

2) Reverse transcription (1st strand cDNA synthesis): A master mix was prepared by mixing 5.0 μL of Buffer for SUPERSCRIPT® IV (5×, Thermo Fisher), 1.0 μL of RNASEOUT®, 1.0 μL of SUPERSCRIPT® IV (Thermo Fisher), and 2.0 μL of DTT (fresh 0.1M). 9.0 μL of the master mix was added to each reaction in the PCR plate, and mixed well by pipetting for 5 times. The PCR plate was incubated in a thermocycler to perform reverse transcription using the following program: 25° C. for 10 min, 42° C. for 30 min, 70° C. for 15 min, 4° C. and hold (with heat lid on at 103° C.).

3) Second strand cDNA synthesis: A master mix was prepared by mixing 18.00 μL of DEPC-treated water, 5.0 μL of 10× Second-Strand Reaction Buffer, 4.0 μL of DNA Polymerase I, and 1.0 μL of RNase H. 28 μL of the master mix was added to each reaction from above, mixed gently by pipetting for 5 times. The temperature of the reaction mixed was not allowed to rise above 16° C. The reaction mixture was incubated at 16° C. for 2 hours, followed by 4° C. hold (with heat lid off).

The reaction mixtures were cleaned up using 1.8× volume (i.e. 90 μL) of AMPURE® beads, following the SPRI manufacture's cleanup protocol and elute in a final 15 μL of 1× Tris-Buffer.

A sequencing library was prepared from the cleaned-up reaction mixture, sequenced and analyzed following the same steps as described in Example 1 (steps 1-5), EML4-ALK and KRAS mutations (e.g., G12D, G13C, and G13D) detected here are implication in lung cancer.

Example 3: Comparison of Target Enrichment Methods

This example compares various target enrichment methods involving exponential amplification (i.e., AMP method) versus linear amplification (i.e., exemplary method of the present application) in target enrichment 1 (i.e., step 2 of Example 1), fast versus slow temperature ramping mode during primer extension cycles, and different starting amounts of DNA samples.

As shown in Table 3, a multiplexed sequencing library having a total of 24 target enriched samples were prepared to assess three different experimental factors, each factor having two different settings, and each experimental condition combination was tested in triplicates. Same experimental steps as described in Example 1 were carried out, except for the three experimental factors. The three factors were: (1) DNA input amount (50 ng or 5 ng); (2) Target enrichment 1 step: primer extension (i.e., linear amplification) or PCR amplification (i.e., exponential amplification); and (3) primer extension temperature ramping mode (regular ramping: 95° C. 3 min; 20 cycles of [95° C. 30 s, ramp down to 60° C. at 0.5° C./sec and hold at 60° C. for 10 min, 72° C. 30 s]; 4° C. hold; and slow ramping: 95° C. 3 min; 20 cycles of [95° C. 30 s, ramp down to 60° C. at 0.2° C./sec and hold at 60° C. for 10 min, ramp up to 95° C. at 0.2° C./sec]; 4° C. hold).

TABLE 3

Experimental Conditions.

| Input DNA, ng | Universal Adaptor | Library ID | Target Enrichment 1 | Temperature Ramping Mode | Replicate No. |
|---|---|---|---|---|---|
| 50 | Y01 | L17-00154 | Exponential | Regular | 1 |
| 50 | Y02 | L17-00155 | Exponential | Regular | 2 |
| 50 | Y03 | L17-00156 | Exponential | Regular | 3 |
| 5 | Y04 | L17-00157 | Exponential | Regular | 1 |
| 5 | Y05 | L17-00158 | Exponential | Regular | 2 |
| 5 | Y06 | L17-00159 | Exponential | Regular | 3 |
| 50 | Y07 | L17-00160 | Linear | Regular | 1 |
| 50 | Y08 | L17-00161 | Linear | Regular | 2 |
| 50 | Y09 | L17-00162 | Linear | Regular | 3 |
| 5 | Y10 | L17-00163 | Linear | Regular | 1 |
| 5 | Y11 | L17-00164 | Linear | Regular | 2 |
| 5 | Y12 | L17-00165 | Linear | Regular | 3 |
| 50 | Y13 | L17-00166 | Exponential | Slow ramping down and up | 1 |
| 50 | Y14 | L17-00167 | Exponential | Slow ramping down and up | 2 |
| 50 | Y15 | L17-00168 | Exponential | Slow ramping down and up | 3 |
| 5 | Y16 | L17-00169 | Exponential | Slow ramping down and up | 1 |
| 5 | Y17 | L17-00170 | Exponential | Slow ramping down and up | 2 |
| 5 | Y18 | L17-00171 | Exponential | Slow ramping down and up | 3 |
| 50 | Y19 | L17-00172 | Linear | Slow ramping down and up | 1 |
| 50 | Y20 | L17-00173 | Linear | Slow ramping down and up | 2 |
| 50 | Y21 | L17-00174 | Linear | Slow ramping down and up | 3 |
| 5 | Y22 | L17-00175 | Linear | Slow ramping down and up | 1 |
| 5 | Y23 | L17-00176 | Linear | Slow ramping down and up | 2 |
| 5 | Y24 | L17-00177 | Linear | Slow ramping down and up | 3 |

Figure 7A:
FIG. 7A shows RNA-based detection of EML4-ALK gene fusion in the X32-P732 sample.
Figure 7B:
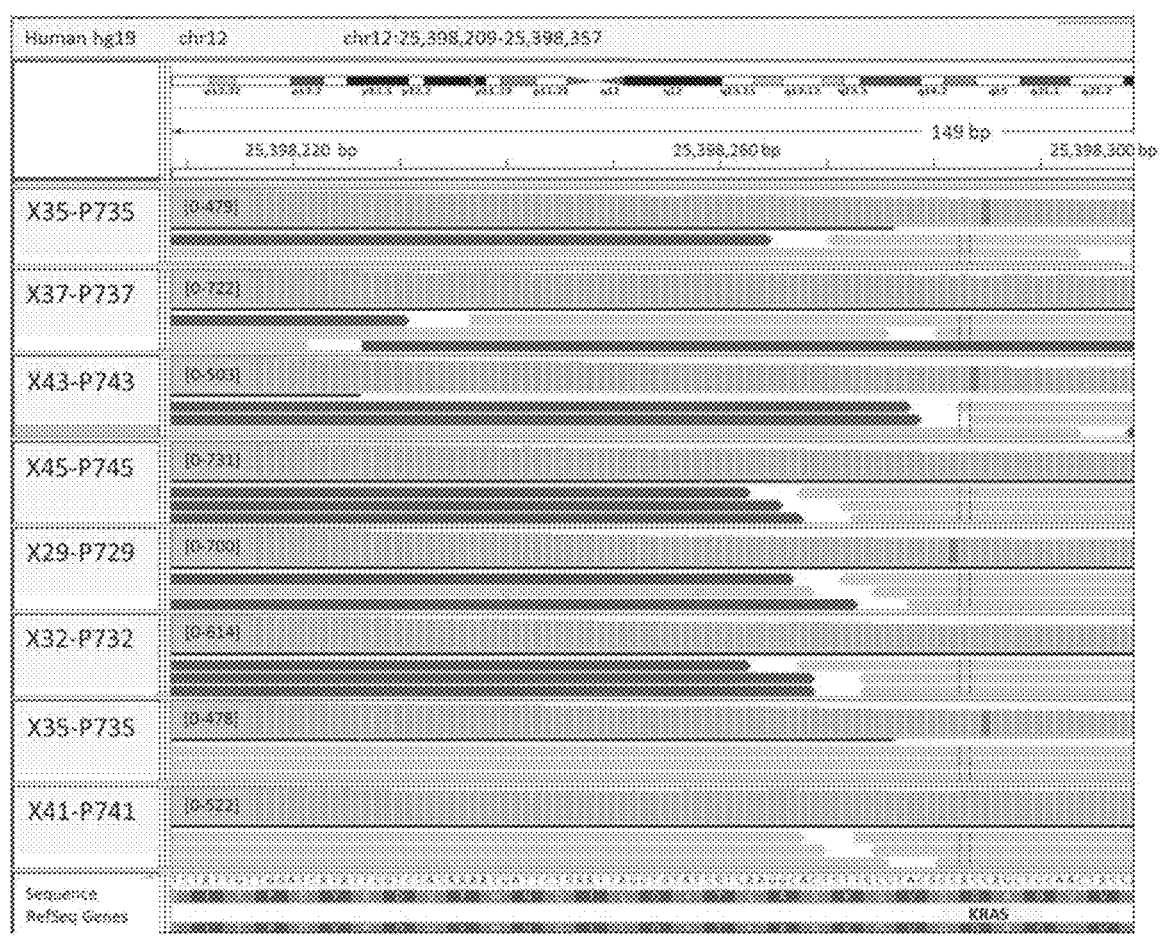
FIG. 7B shows gDNA-based detection of mutations in KRAS in the X32-P732 sample.
Figure 8A:
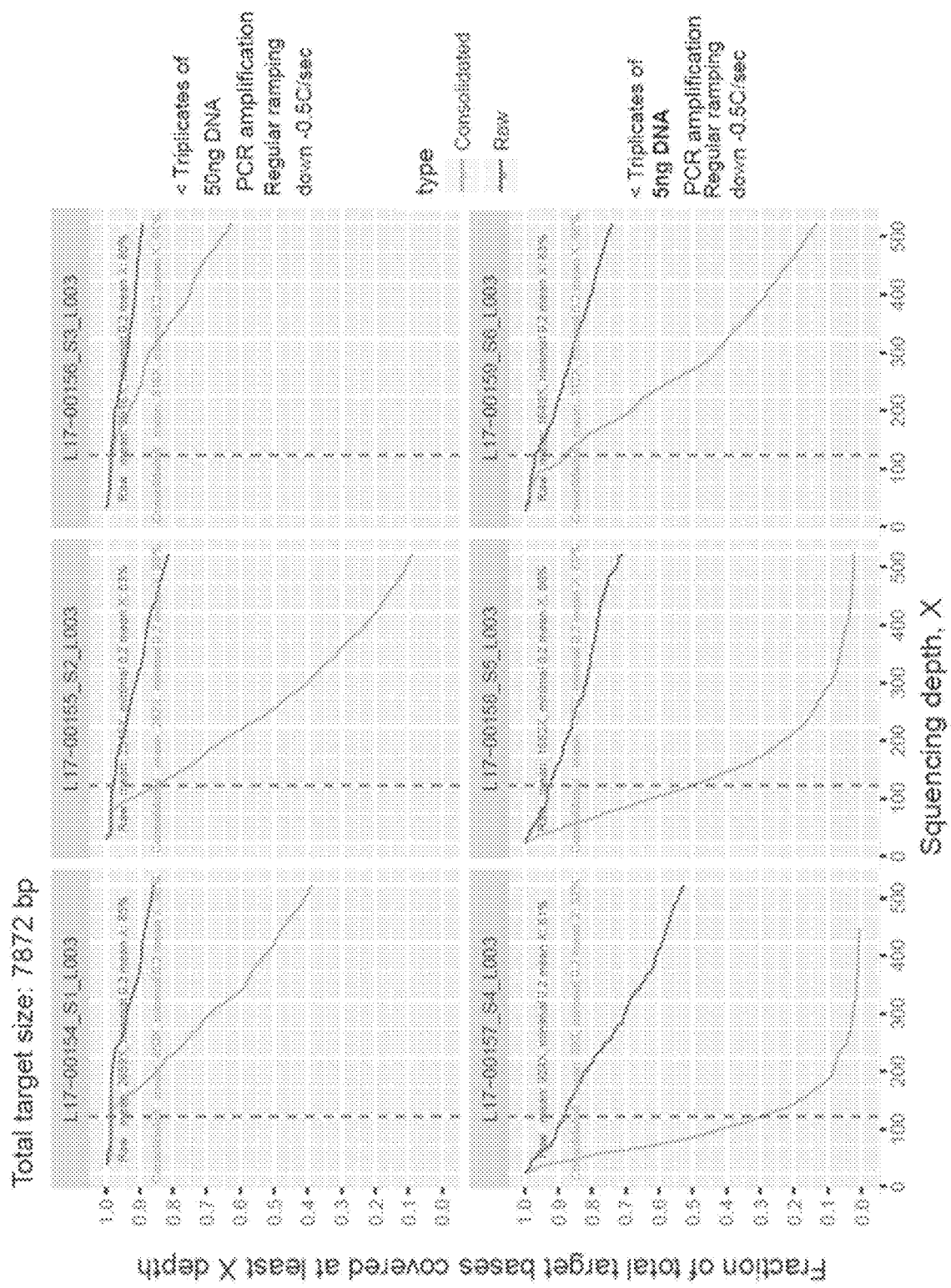
FIG. 8A shows overall panel coverage statistics of sequencing libraries L17-00154 to L17-00159.
Figure 8B:
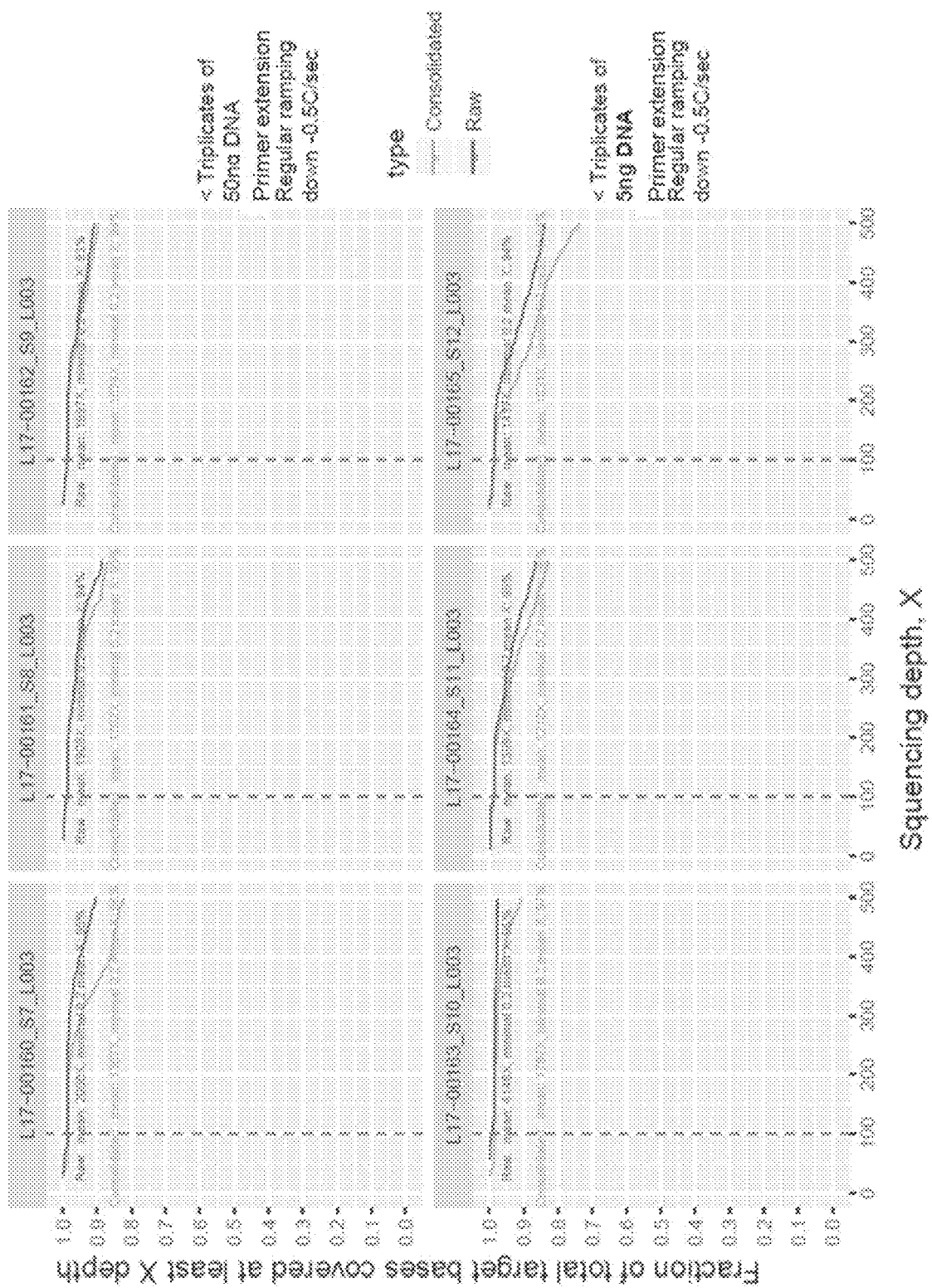
FIG. 8B shows overall panel coverage statistics of sequencing libraries L17-00160 to L17-00165.
Figure 8C:
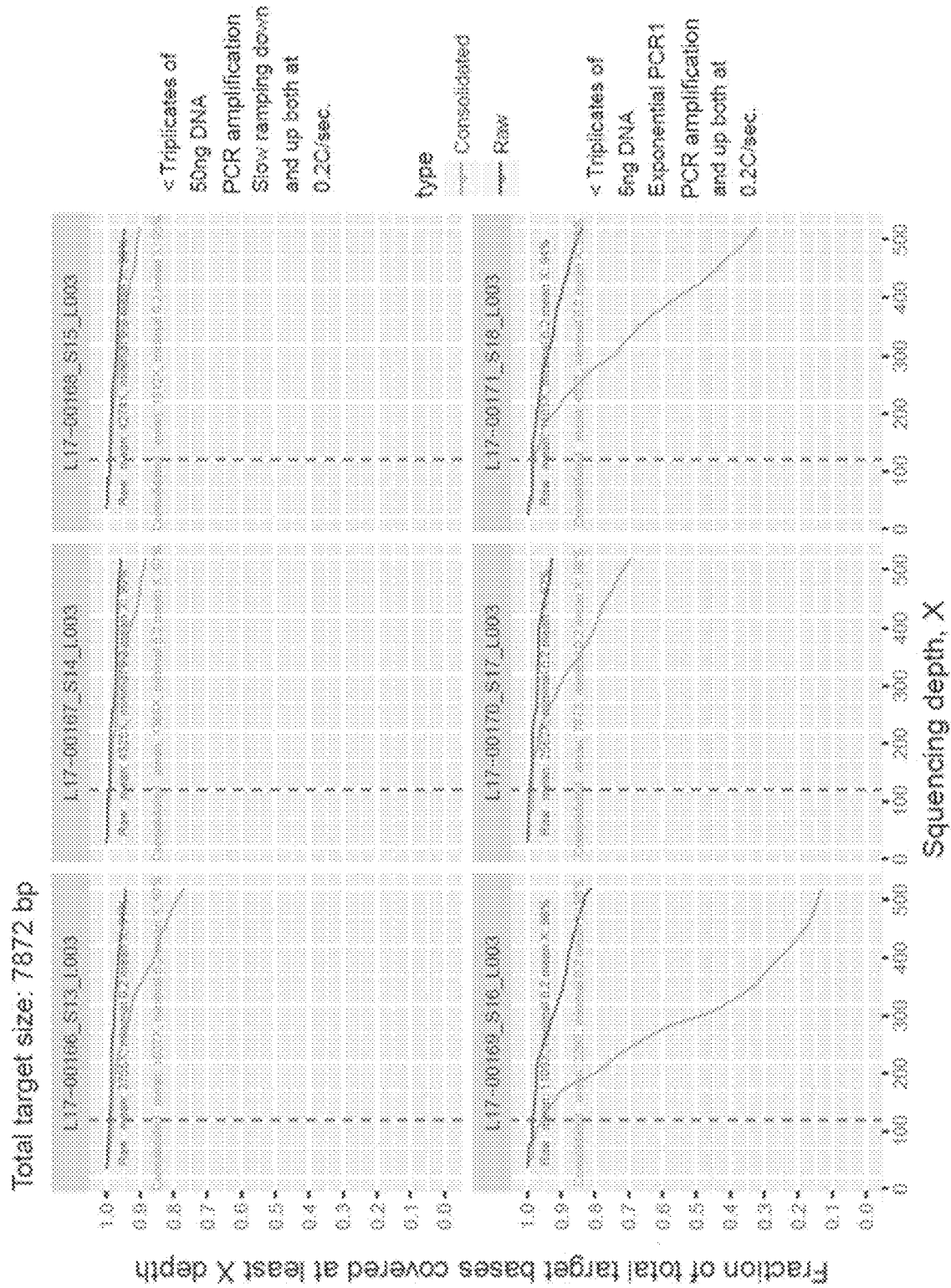
FIG. 8C shows overall panel coverage statistics of sequencing libraries L17-00166 to L17-00171.
Figure 8D:
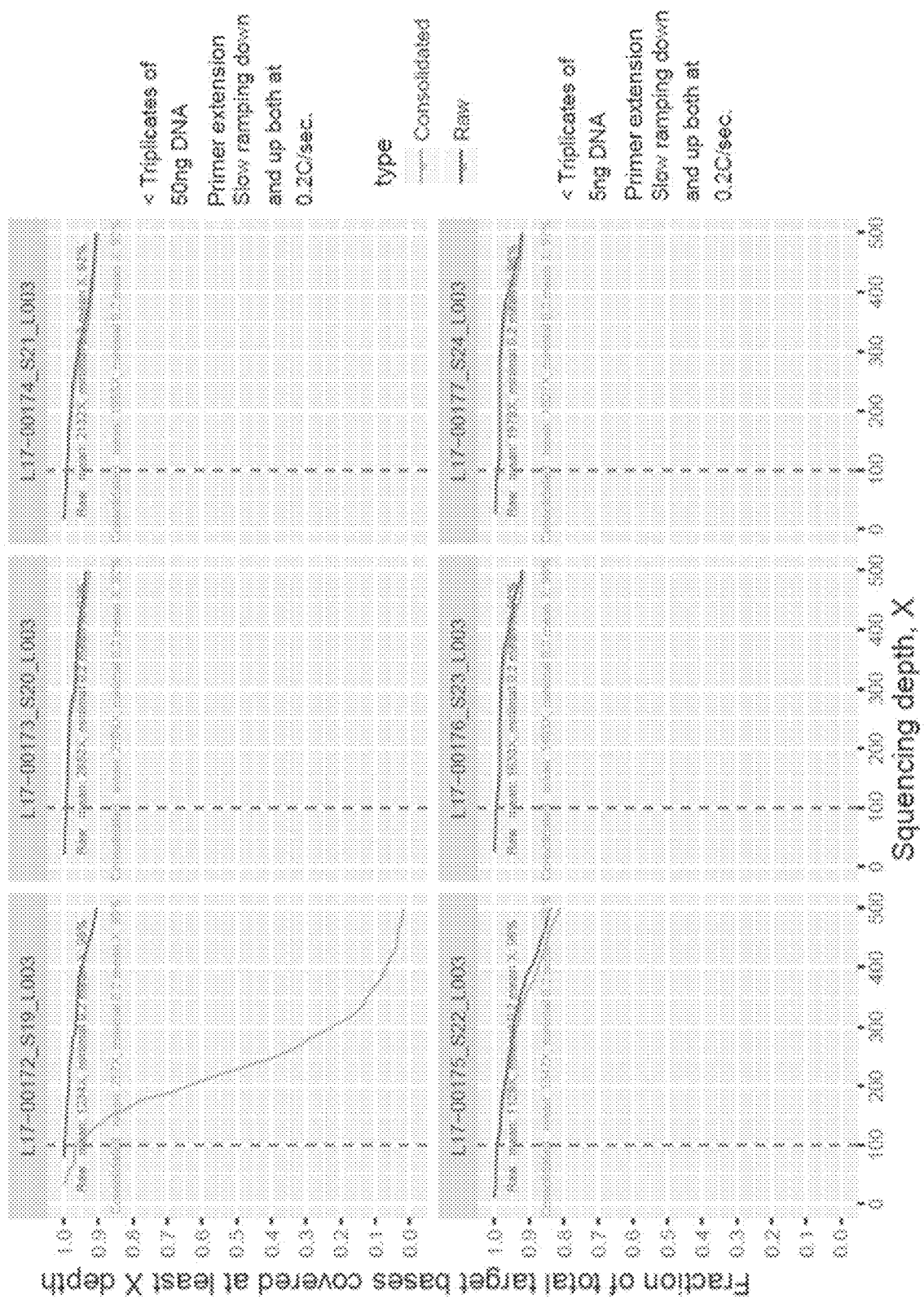
FIG. 8D shows overall panel coverage statistics of sequencing libraries L17-00172 to L17-00177.
Figure 9A:
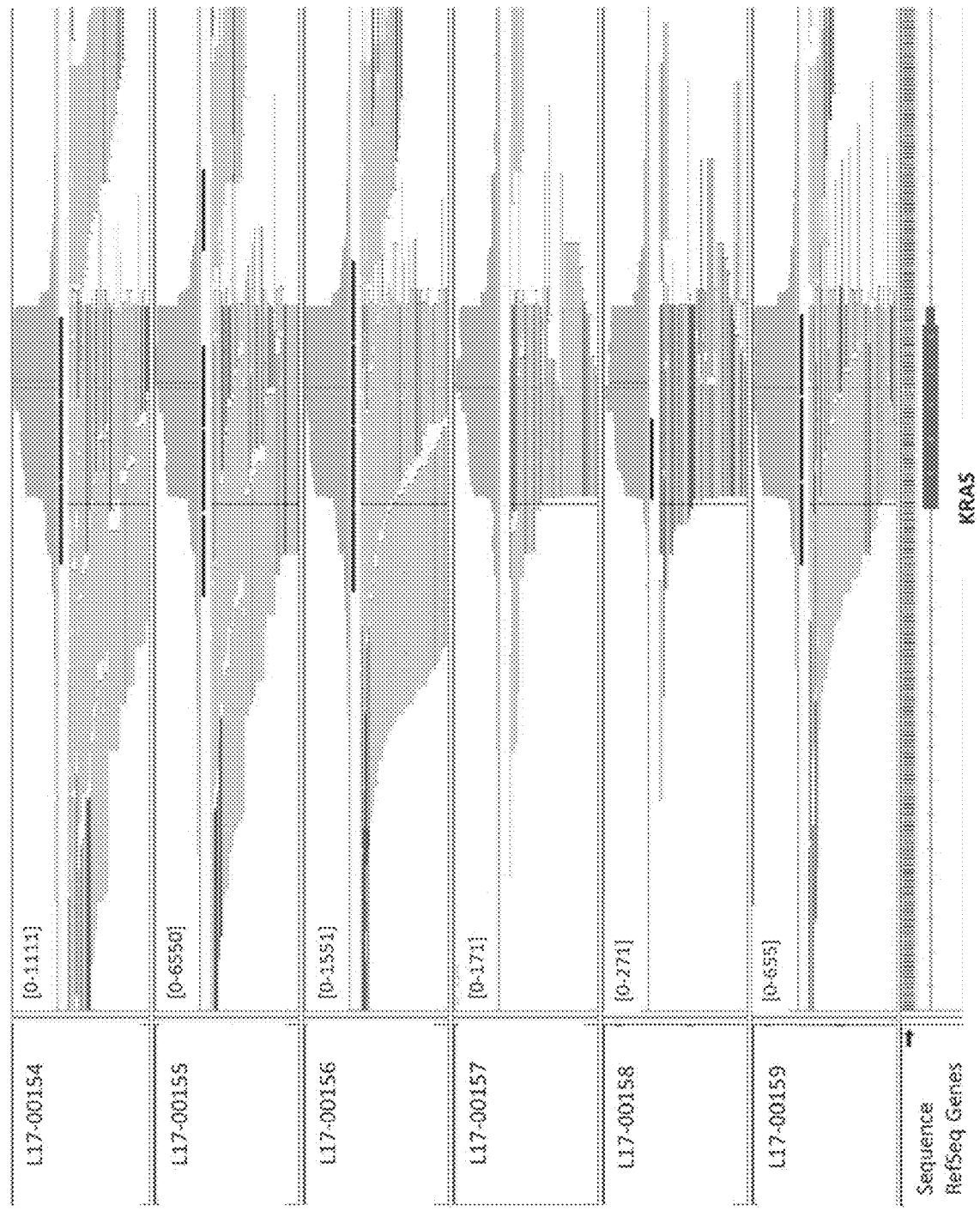
FIG. 9A shows coverage on KRAS exon 2 by mapped reads from sequencing libraries L17-00154 to L17-00159.
Figure 9B:
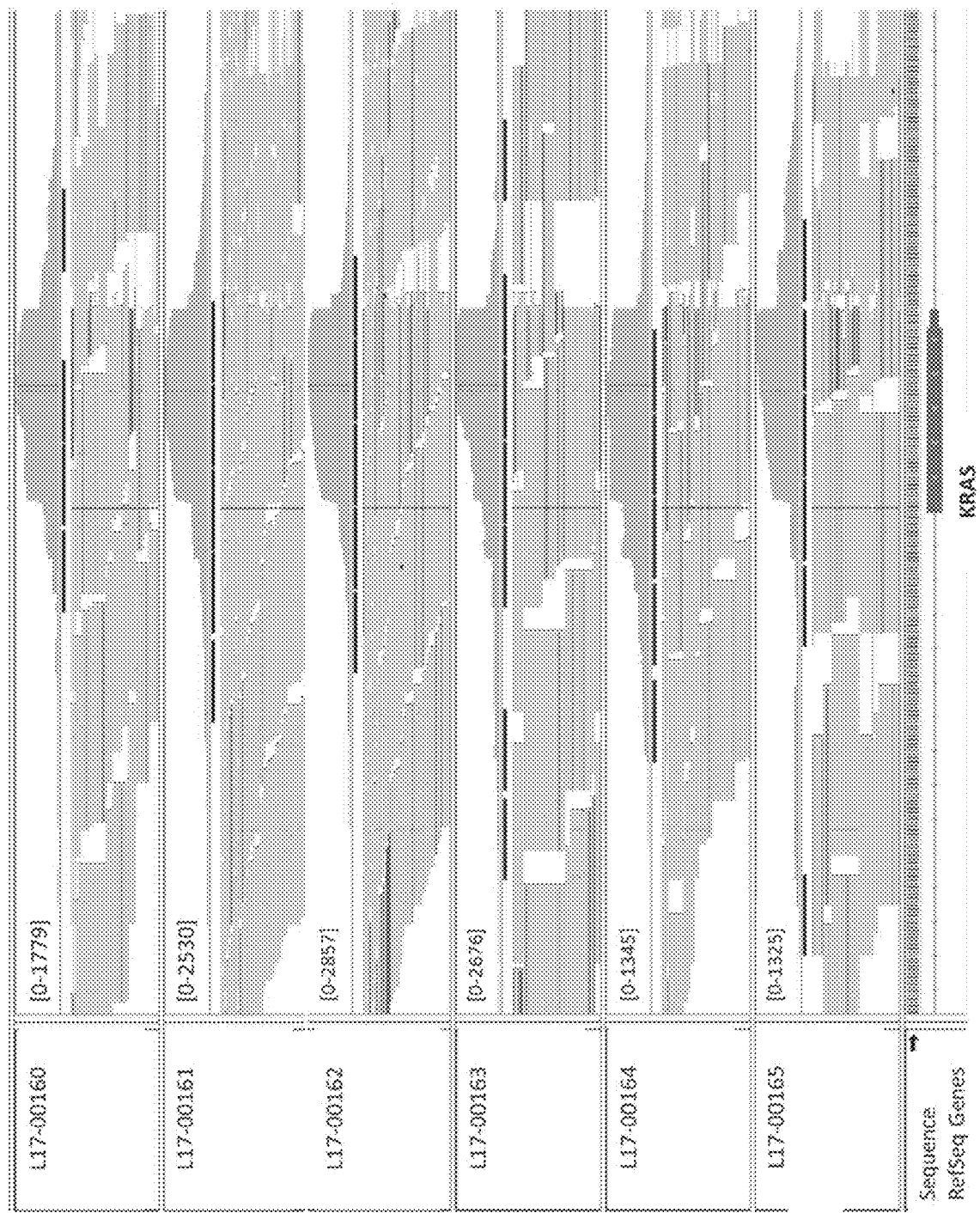
FIG. 9B shows coverage on KRAS exon 2 by mapped reads from sequencing libraries L17-00160 to L17-00165.
Figure 9C:
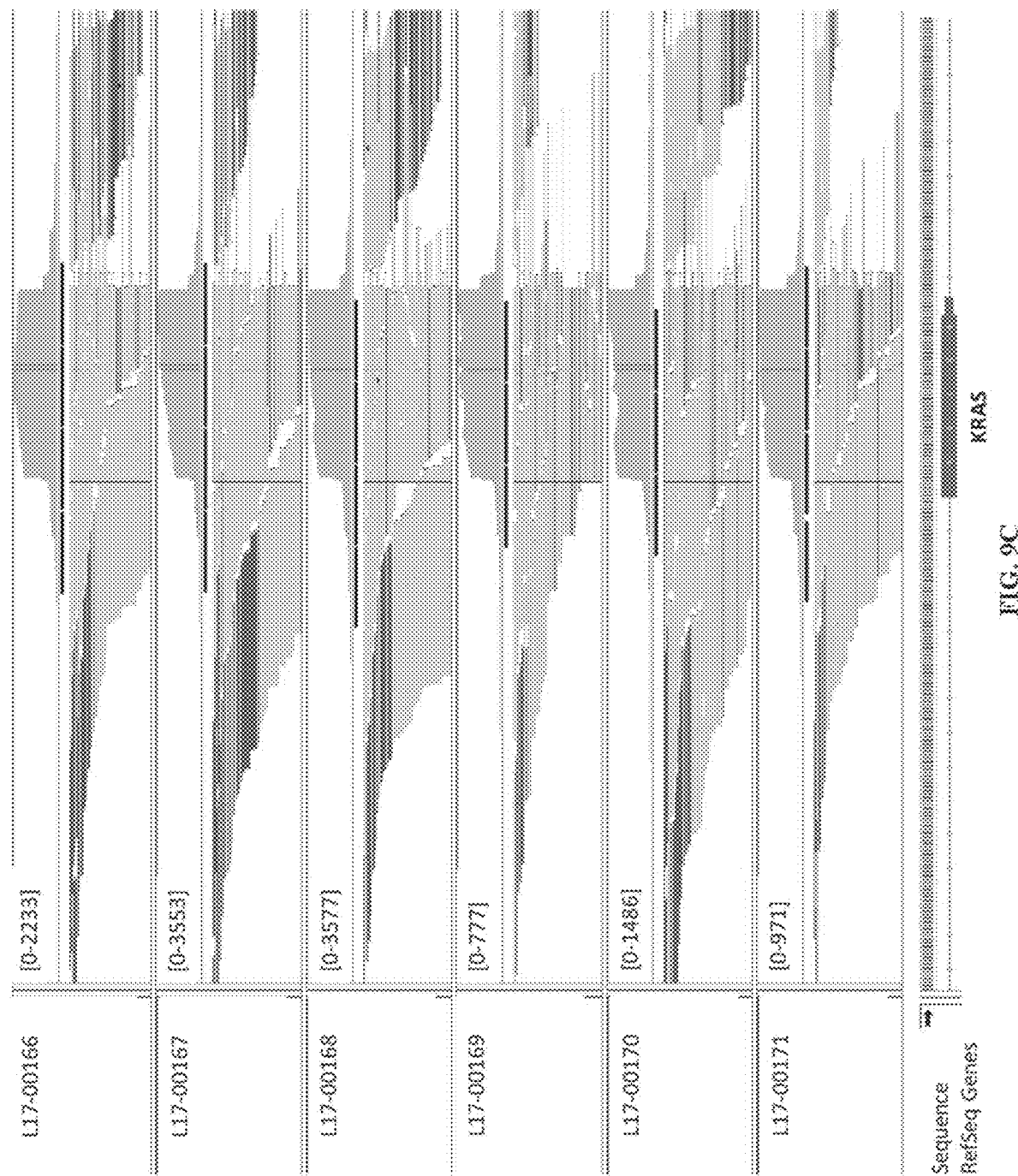
FIG. 9C shows coverage on KRAS exon 2 by mapped reads from sequencing libraries L17-00166 to L17-00171.
Figure 9D:
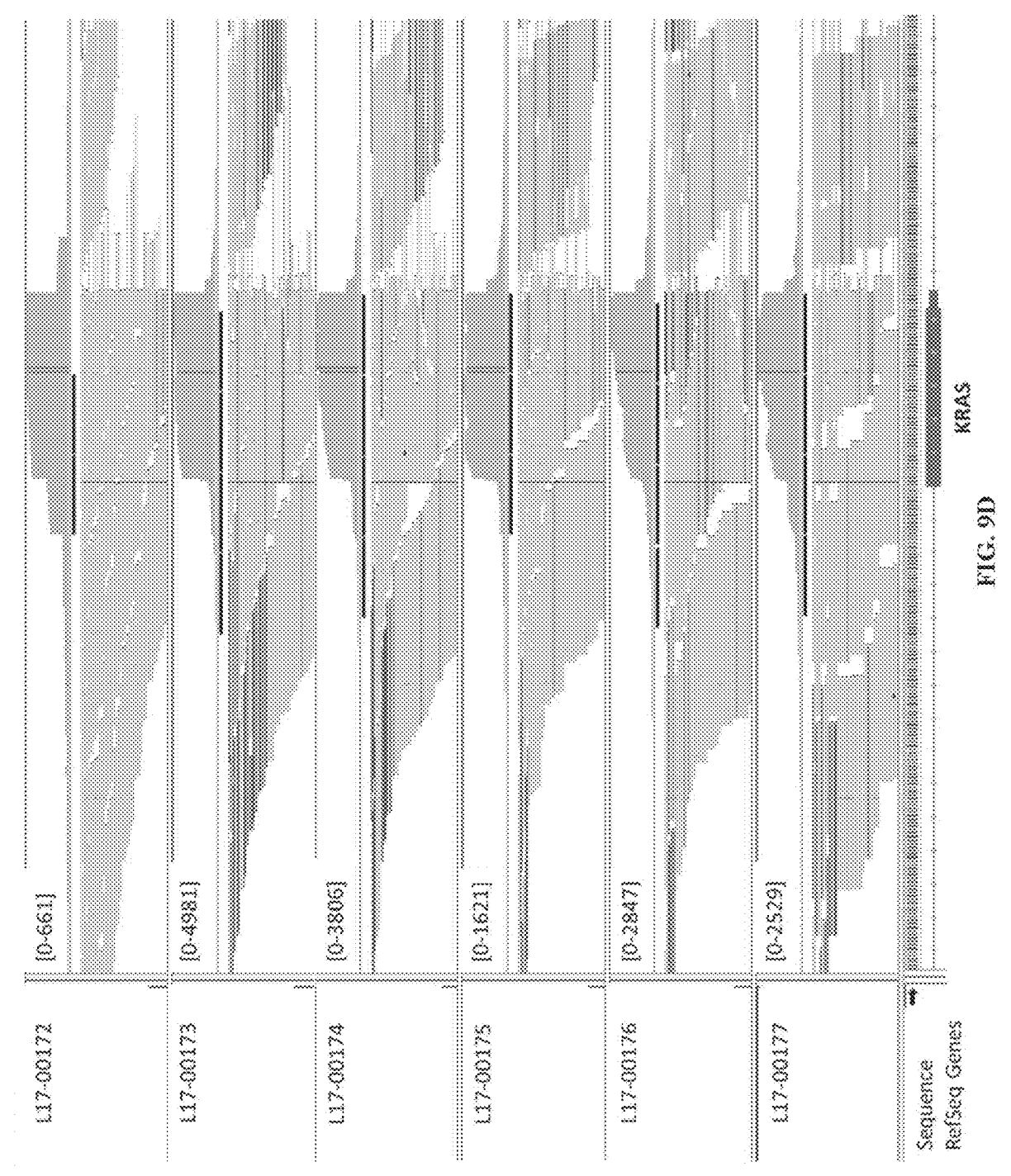

FIGS. 6A-6F demonstrate successful RNA-based detection of various gene fusions associated with cancer using the exemplary method described herein. FIGS. 7A-7B demonstrate simultaneous RNA-based detection of EML4-ALK gene fusion (FIG. 7A) and gDNA-based detection of KRAS mutations (FIG. 7B) in one single sequencing sample. Both As shown in FIGS. 8A-8D and Table 3, methods with primer extension cycles (i.e., linear amplification) in target enrichment 1 (i.e., step 2 of Example 1) compared to PCR amplification cycles (i.e., PCR amplification), and the temperature ramping mode compared to regular ramping mode resulted in higher library construction efficiencies when using both 50 ng and 5 ng DNA. FIGS. 9A-9D further shows coverage on KRAS exon 2 by mapped reads from the 12 sequencing libraries.

TABLE 3

Overall panel coverage statistics.

| Library ID | Raw | | Consolidated | |
|---|---|---|---|---|
| | Mean depth | % sequences with >0.2 × Mean depth | Mean depth | % sequences with >0.2 × Mean depth |
| L17-00154 | 2659 | 85 | 480 | 98 |
| L17-00155 | 2315 | 83 | 282 | 98 |
| L17-00156 | 3916 | 80 | 816 | 94 |
| L17-00157 | 924 | 81 | 89 | 92 |
| L17-00158 | 1682 | 80 | 137 | 89 |
| L17-00159 | 1649 | 83 | 312 | 96 |
| L17-00160 | 2000 | 95 | 1367 | 96 |
| L17-00161 | 1908 | 94 | 1702 | 95 |
| L17-00162 | 1997 | 93 | 1834 | 94 |
| L17-00163 | 4146 | 95 | 1797 | 97 |
| L17-00164 | 1399 | 95 | 1212 | 96 |
| L17-00165 | 1417 | 94 | 1031 | 94 |

TABLE 3-continued

Overall panel coverage statistics.

| Library ID | Raw | | Consolidated | |
|---|---|---|---|---|
| | Mean depth | % sequences with >0.2 × Mean depth | Mean depth | % sequences with >0.2 × Mean depth |
| L17-00166 | 3755 | 94 | 1037 | 97 |
| L17-00167 | 4325 | 90 | 1366 | 97 |
| L17-00168 | 4274 | 90 | 1612 | 95 |
| L17-00169 | 1109 | 96 | 329 | 98 |
| L17-00170 | 2562 | 92 | 787 | 98 |
| L17-00171 | 1401 | 94 | 493 | 98 |
| L17-00172 | 1234 | 98 | 257 | 99 |
| L17-00173 | 2852 | 92 | 2604 | 92 |
| L17-00174 | 2132 | 92 | 1955 | 92 |
| L17-00175 | 1129 | 96 | 1047 | 96 |
| L17-00176 | 1633 | 98 | 1493 | 98 |
| L17-00177 | 1979 | 96 | 1827 | 97 |

The disclosures of all publications, patents, patent applications and published patent applications referred to herein are hereby incorporated herein by reference in their entirety.

What is claimed is:

1. A method of enriching a target nucleotide sequence having a locus of interest from a nucleic acid sample comprising a nucleic acid template comprising the target nucleotide sequence, the method comprising:
   (a) ligating a universal adaptor to the nucleic acid template to provide a ligated nucleic acid, wherein the universal adaptor is an oligonucleotide comprising a duplex portion at a first end and a non-duplex portion at a second end, and wherein the nucleic acid template is ligated to the universal adaptor via the first end;
   (b) dissociating the ligated nucleic acid into a first strand and a second strand, wherein the first strand comprises the target nucleotide sequence;
   (c) annealing an outside primer to the first strand of the ligated nucleic acid in the vicinity of the target nucleotide sequence;
   (d) extending the outside primer over the full length of the first strand of the ligated nucleic acid using a DNA polymerase to provide a nascent DNA linear amplification duplex;
   (e) dissociating the nascent DNA linear amplification duplex at a sufficiently high temperature into the first strand of the ligated nucleic acid and a single-stranded DNA linear amplification product;
   (f) repeating steps (c)-(e) for nineteen or more DNA linear amplification cycles;
   (g) contacting the single-stranded DNA linear amplification products with a DNA polymerase, a universal adaptor primer and an inside primer under a condition sufficient for PCR amplification of the target nucleotide sequence, wherein the universal adaptor primer anneals to a complementary sequence of the non-duplex portion of the universal adaptor in the single-stranded DNA linear amplification products, wherein the inside primer comprises a sequence at the 3' end that specifically anneals to the target nucleotide sequence, and wherein the inside primer is nested with respect to the outside primer for the locus of interest; and
   (h) repeating step (g) for one or more cycles of PCR amplification to provide amplicons of the target nucleotide sequence, thereby enriching the target nucleotide sequence;
   wherein, the nucleic acid sample input is from 5 ng to 50 ng.

2. The method according to claim 1, wherein
   (1) the outside primer anneals to a region about 1-100 nucleotides farther away from the locus of interest than the inside primer; and/or
   (2) at least the last 12 nucleotides of the outside primer and/or the inside primer have fewer than about 20 different annealing loci in the nucleic acid sample.

3. The method according to claim 1, wherein
   (1) the nucleic acid template is genomic DNA, optionally, wherein the genomic DNA is chromosomal DNA, or mitochondrial DNA or other extra-chromosomal DNA; or
   (2) the nucleic acid template is exome DNA; or
   (3) the nucleic acid template is cDNA, optionally, the cDNA is obtained by reverse transcription of total RNA, or the cDNA is obtained by reverse transcription of mRNA, miRNA, or other noncoding RNAs;
   (4) the nucleic acid template is cell-free DNA derived from a blood sample;

and wherein
- (5) the nucleic acid sample comprises both genomic DNA and cDNA; or
- (6) the nucleic acid sample is derived from a blood sample; or
- (7) the nucleic acid sample is derived from a cell or tissue sample, optionally, wherein the nucleic acid sample is derived from a tumor biopsy sample or a Formalin-Fixed Paraffin-Embedded (FFPE) sample.

4. The method according to claim 1, wherein
- (1) the locus of interest is associated with a chromosomal rearrangement, wherein the chromosomal rearrangement is chromosomal translocation; or
- (2) the locus of interest is associated with a single nucleotide variant (SNV); or
- (3) the locus of interest is associated with an indel; or
- (4) the locus of interest is associated with a splice variant.

5. The method according to claim 1, wherein
- (1) the locus of interest is located in a gene associated with cancer;
- (2) the locus of interest is located in a gene encoding an immune cell receptor;
- (3) the locus of interest is located in a gene associated with a hereditary disease; or
- (4) the locus of interest is located in an off-target site of CRISPR gene editing.

6. The method according to claim 1, wherein
- (1) the method further comprises end repairing and A-tailing of the nucleic acid template prior to step (a);
- (2) the non-duplex portion of the universal adaptor comprises a 3' end having a blocking moiety, optionally, the blocking moiety is an inverted nucleotide;
- (3) the non-duplex portion of the universal adaptor comprises a molecular barcode comprising degenerately designed nucleobases, the duplex portion of the universal adaptor comprises a sample barcode, optionally, the sample barcode is located at the first end of the universal adaptor;
- (4) the first end of the universal adaptor comprises constant nucleobases of a sufficiently short length to prevent promiscuous priming during steps (b)-(f) by carryover universal adaptor;
- (5) the sufficiently high temperature is at least about 90° C.;
- (6) the ligated nucleic acid is subjected to a cleanup procedure prior to step (b);
- (7) the linear amplification products are subjected to a cleanup procedure prior to step (g);
- (8) step (g) is repeated for about 2-100 cycles; and/or
- (9) the amplicons of the target nucleotide sequence are used for next-generation sequencing (NGS), and the universal adaptor or the 5' end of the universal adaptor primer comprises a sequence identical or complementary to the sequence of a first sequencing primer for the NGS, optionally, step (g) comprises contacting the single-stranded linear amplification products with a DNA polymerase, a universal adaptor primer, an inside primer, and a sequencing adaptor primer under a condition sufficient for PCR amplification of the target nucleotide sequence, wherein the sequencing adaptor primer comprises at the 3' end a sequence identical to a sequence of the inside primer, and at the 5' end a sequence identical or complementary to the sequence of a second sequencing primer for the NGS.

7. A method of determining a target nucleotide sequence having a locus of interest in a nucleic acid sample comprising a nucleic acid template comprising the target nucleotide sequence, the method comprising:
- (i) enriching the target nucleotide sequence having the locus of interest using the method of claim 1; and
- (ii) performing next-generation sequencing of the amplicons of the target nucleotide sequence, thereby providing the target nucleotide sequence, optionally, wherein:
- (a) target nucleotide sequences having about 2-5000 different loci of interest are determined simultaneously;
- (b) the method further comprising preparing a sequencing library using the amplicons of the target nucleotide sequence prior to the next-generation sequencing of step (ii).

8. A method of determining a target nucleotide sequence having a locus of interest in a nucleic acid sample comprising a nucleic acid template comprising the target nucleotide sequence, the method comprising:
- (i) enriching the target nucleotide sequence having the locus of interest using the method of claim 2; and
- (ii) performing next-generation sequencing of the amplicons of the target nucleotide sequence, thereby providing the target nucleotide sequence, optionally, wherein:
- (a) target nucleotide sequences having about 2-5000 different loci of interest are determined simultaneously;
- (b) the method further comprising preparing a sequencing library using the amplicons of the target nucleotide sequence prior to the next-generation sequencing of step (ii).

9. A method of determining a target nucleotide sequence having a locus of interest in a nucleic acid sample comprising a nucleic acid template comprising the target nucleotide sequence, the method comprising:
- (i) enriching the target nucleotide sequence having the locus of interest using the method of claim 3; and
- (ii) performing next-generation sequencing of the amplicons of the target nucleotide sequence, thereby providing the target nucleotide sequence, optionally, wherein:
- (a) target nucleotide sequences having about 2-5000 different loci of interest are determined simultaneously;
- (b) the method further comprising preparing a sequencing library using the amplicons of the target nucleotide sequence prior to the next-generation sequencing of step (ii).

10. A method of determining a target nucleotide sequence having a locus of interest in a nucleic acid sample comprising a nucleic acid template comprising the target nucleotide sequence, the method comprising:
- (i) enriching the target nucleotide sequence having the locus of interest using the method of claim 4; and
- (ii) performing next-generation sequencing of the amplicons of the target nucleotide sequence, thereby providing the target nucleotide sequence, optionally, wherein:
- (a) target nucleotide sequences having about 2-5000 different loci of interest are determined simultaneously;
- (b) the method further comprising preparing a sequencing library using the amplicons of the target nucleotide sequence prior to the next-generation sequencing of step (ii).

11. A method of determining a target nucleotide sequence having a locus of interest in a nucleic acid sample comprising a nucleic acid template comprising the target nucleotide sequence, the method comprising:

(i) enriching the target nucleotide sequence having the locus of interest using the method of claim 5; and (ii) performing next-generation sequencing of the amplicons of the target nucleotide sequence, thereby providing the target nucleotide sequence, optionally, wherein:

(a) target nucleotide sequences having about 2-5000 different loci of interest are determined simultaneously;

(b) the method further comprising preparing a sequencing library using the amplicons of the target nucleotide sequence prior to the next-generation sequencing of step (ii).

12. A method of determining a target nucleotide sequence having a locus of interest in a nucleic acid sample comprising a nucleic acid template comprising the target nucleotide sequence, the method comprising:

(i) enriching the target nucleotide sequence having the locus of interest using the method of claim 6; and (ii) performing next-generation sequencing of the amplicons of the target nucleotide sequence, thereby providing the target nucleotide sequence, optionally, wherein:

(a) target nucleotide sequences having about 2-5000 different loci of interest are determined simultaneously;

(b) the method further comprising preparing a sequencing library using the amplicons of the target nucleotide sequence prior to the next-generation sequencing of step (ii).

13. A method of detecting a sequence variant at a locus of interest in a nucleic acid sample comprising a nucleic acid template comprising a target nucleotide sequence having the locus of interest, the method comprising:

(1) determining the target sequence having the locus of interest using the method of claim 7; and (2) detecting the sequence variant in the target nucleotide sequence, optionally, wherein:

(a) the sequence variant is present at an allele frequency of no more than about 1:100;

(b) the sequence variant is inherited in germline DNA;

(c) the sequence variant is a somatic mutation or chromosomal rearrangement;

(d) a plurality of sequence variants are detected, wherein the plurality of sequence variants are selected from the group consisting of chromosomal rearrangements, splice variants, SNP, deletions, insertions, copy number variants (CNV), and combinations thereof; and/or (e) the method simultaneously detects a chromosomal rearrangement based on cDNA sequences, and a mutation based on gDNA sequences.

14. A method of detecting a sequence variant at a locus of interest in a nucleic acid sample comprising a nucleic acid template comprising a target nucleotide sequence having the locus of interest, the method comprising:

(1) determining the target sequence having the locus of interest using the method of claim 8; and (2) detecting the sequence variant in the target nucleotide sequence, optionally, wherein:

(a) the sequence variant is present at an allele frequency of no more than about 1:100;

(b) the sequence variant is inherited in germline DNA;

(c) the sequence variant is a somatic mutation or chromosomal rearrangement;

(d) a plurality of sequence variants are detected, wherein the plurality of sequence variants are selected from the group consisting of chromosomal rearrangements, splice variants, SNP, deletions, insertions, copy number variants (CNV), and combinations thereof; and/or (e) the method simultaneously detects a chromosomal rearrangement based on cDNA sequences, and a mutation based on gDNA sequences.

15. A method of detecting a sequence variant at a locus of interest in a nucleic acid sample comprising a nucleic acid template comprising a target nucleotide sequence having the locus of interest, the method comprising:

(1) determining the target sequence having the locus of interest using the method of claim 9; and (2) detecting the sequence variant in the target nucleotide sequence, optionally, wherein:

(a) the sequence variant is present at an allele frequency of no more than about 1:100;

(b) the sequence variant is inherited in germline DNA;

(c) the sequence variant is a somatic mutation or chromosomal rearrangement;

(d) a plurality of sequence variants are detected, wherein the plurality of sequence variants are selected from the group consisting of chromosomal rearrangements, splice variants, SNP, deletions, insertions, copy number variants (CNV), and combinations thereof; and/or (e) the method simultaneously detects a chromosomal rearrangement based on cDNA sequences, and a mutation based on gDNA sequences.

16. A method of detecting a sequence variant at a locus of interest in a nucleic acid sample comprising a nucleic acid template comprising a target nucleotide sequence having the locus of interest, the method comprising:

(1) determining the target sequence having the locus of interest using the method of claim 10; and (2) detecting the sequence variant in the target nucleotide sequence, optionally, wherein:

(a) the sequence variant is present at an allele frequency of no more than about 1:100;

(b) the sequence variant is inherited in germline DNA;

(c) the sequence variant is a somatic mutation or chromosomal rearrangement;

(d) a plurality of sequence variants are detected, wherein the plurality of sequence variants are selected from the group consisting of chromosomal rearrangements, splice variants, SNP, deletions, insertions, copy number variants (CNV), and combinations thereof; and/or (e) the method simultaneously detects a chromosomal rearrangement based on cDNA sequences, and a mutation based on gDNA sequences.

17. A method of detecting a sequence variant at a locus of interest in a nucleic acid sample comprising a nucleic acid template comprising a target nucleotide sequence having the locus of interest, the method comprising:

(1) determining the target sequence having the locus of interest using the method of claim 11; and (2) detecting the sequence variant in the target nucleotide sequence, optionally, wherein:

(a) the sequence variant is present at an allele frequency of no more than about 1:100;

(b) the sequence variant is inherited in germline DNA;

(c) the sequence variant is a somatic mutation or chromosomal rearrangement;

(d) a plurality of sequence variants are detected, wherein the plurality of sequence variants are selected from the group consisting of chromosomal rearrangements, splice variants, SNP, deletions, insertions, copy number variants (CNV), and combinations thereof; and/or (e) the method simultaneously detects a chromosomal rearrangement based on cDNA sequences, and a mutation based on gDNA sequences.

18. A method of detecting a sequence variant at a locus of interest in a nucleic acid sample comprising a nucleic acid template comprising a target nucleotide sequence having the locus of interest, the method comprising:
(1) determining the target sequence having the locus of interest using the method of claim 12; and
(2) detecting the sequence variant in the target nucleotide sequence, optionally, wherein:
(a) the sequence variant is present at an allele frequency of no more than about 1:100;
(b) the sequence variant is inherited in germline DNA;
(c) the sequence variant is a somatic mutation or chromosomal rearrangement;
(d) a plurality of sequence variants are detected, wherein the plurality of sequence variants are selected from the group consisting of chromosomal rearrangements, splice variants, SNP, deletions, insertions, copy number variants (CNV), and combinations thereof; and/or
(e) the method simultaneously detects a chromosomal rearrangement based on cDNA sequences, and a mutation based on gDNA sequences.

19. A method of diagnosing a disease in an individual, comprising detecting a sequence variant associated with the disease at a locus of interest in a nucleic acid sample from the individual using the method of claim 13, analyzing target nucleotide sequences from a tumor cell of the individual, and comparing the target nucleotide sequences to target nucleotide sequences from a healthy cell of the same individual, thereby providing a diagnosis of the disease.

20. A method of diagnosing a disease in an individual, comprising detecting a sequence variant associated with the disease at a locus of interest in a nucleic acid sample from the individual using the method of claim 14, analyzing target nucleotide sequences from a tumor cell of the individual, and comparing the target nucleotide sequences to target nucleotide sequences from a healthy cell of the same individual, thereby providing a diagnosis of the disease.

21. A method of diagnosing a disease in an individual, comprising detecting a sequence variant associated with the disease at a locus of interest in a nucleic acid sample from the individual using the method of claim 15, analyzing target nucleotide sequences from a tumor cell of the individual, and comparing the target nucleotide sequences to target nucleotide sequences from a healthy cell of the same individual, thereby providing a diagnosis of the disease.

22. A method of diagnosing a disease in an individual, comprising detecting a sequence variant associated with the disease at a locus of interest in a nucleic acid sample from the individual using the method of claim 16, analyzing target nucleotide sequences from a tumor cell of the individual, and comparing the target nucleotide sequences to target nucleotide sequences from a healthy cell of the same individual, thereby providing a diagnosis of the disease.

23. A method of diagnosing a disease in an individual, comprising detecting a sequence variant associated with the disease at a locus of interest in a nucleic acid sample from the individual using the method of claim 17, analyzing target nucleotide sequences from a tumor cell of the individual, and comparing the target nucleotide sequences to target nucleotide sequences from a healthy cell of the same individual, thereby providing a diagnosis of the disease.

24. A method of diagnosing a disease in an individual, comprising detecting a sequence variant associated with the disease at a locus of interest in a nucleic acid sample from the individual using the method of claim 18, analyzing target nucleotide sequences from a tumor cell of the individual, and comparing the target nucleotide sequences to target nucleotide sequences from a healthy cell of the same individual, thereby providing a diagnosis of the disease.

* * * * *

SEQUENCE LISTING

```
<160> NUMBER OF SEQ ID NOS: 74

<210> SEQ ID NO 1
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 1
aatgatacgg cgaccaccga gatctacact ctttccctac acgacgctct tccgatctnn     60
nnnnnnyyta gatcgct                                                    77

<210> SEQ ID NO 2
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 2
aatgatacgg cgaccaccga gatctacact ctttccctac acgacgctct tccgatctnn     60
nnnnnnyyct ctctatt                                                    77

<210> SEQ ID NO 3
<211> LENGTH: 77
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 3
aatgatacgg cgaccaccga gatctacact ctttccctac acgacgctct tccgatctnn    60
nnnnnnyyta tcctctt                                                   77

<210> SEQ ID NO 4
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 4
aatgatacgg cgaccaccga gatctacact ctttccctac acgacgctct tccgatctnn    60
nnnnnnyyag agtagat                                                   77

<210> SEQ ID NO 5
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 5
aatgatacgg cgaccaccga gatctacact ctttccctac acgacgctct tccgatctnn    60
nnnnnnyygt aaggagt                                                   77

<210> SEQ ID NO 6
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 6
```
aatgatacgg cgaccaccga gatctacact ctttccctac acgacgctct tccgatctnn    60
nnnnnnyyac tgcatat                                                    77

<210> SEQ ID NO 7
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 7
aatgatacgg cgaccaccga gatctacact ctttccctac acgacgctct tccgatctnn    60
nnnnnnyyaa ggagtat                                                    77

<210> SEQ ID NO 8
<211> LENGTH: 77
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 59, 60, 61, 62, 63, 64, 65, 66
<223> OTHER INFORMATION: n = A,T,C or G
<220> FEATURE:
<221> NAME/KEY: misc_feature
<222> LOCATION: 76, 77
<223> OTHER INFORMATION: phosphorothioate bond modification

<400> SEQUENCE: 8
aatgatacgg cgaccaccga gatctacact ctttccctac acgacgctct tccgatctnn    60
nnnnnnyyct aagcctt                                                    77

<210> SEQ ID NO 9
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 9 gcgatctayy                                                            10

<210> SEQ ID NO 10
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation

```
<400> SEQUENCE: 10 gcgatctayy                                                          10

<210> SEQ ID NO 11
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 11 atagagagyy                                                          10

<210> SEQ ID NO 12
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 12 agaggatayy                                                          10

<210> SEQ ID NO 13
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 13 tctactctyy                                                          10

<210> SEQ ID NO 14
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
```

```
<223> OTHER INFORMATION: phosphorothioate bond modification

<400> SEQUENCE: 14 ctccttacyy                                                            10

<210> SEQ ID NO 15
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 15 tatgcagtyy                                                            10

<210> SEQ ID NO 16
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 16 tactccttyy                                                            10

<210> SEQ ID NO 17
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: 5' phosphorylation
<220> FEATURE:
<221> NAME/KEY: misc_feature
<222> LOCATION: 8, 9, 10
<223> OTHER INFORMATION: phosphorothioate bond modification

<400> SEQUENCE: 17 aggcttagyy                                                            10

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct

<400> SEQUENCE: 18
aatgatacgg cgaccaccga gatcta                                          26
```

```
<210> SEQ ID NO 19
<211> LENGTH: 53
<212> TYPE: DNA
<213> ORGANISM: Artificial Sequence
<220> FEATURE:
<223> OTHER INFORMATION: Synthetic Construct

<400> SEQUENCE: 19
caagcagaag acggcatacg agattcgcct tagtgactgg agttcagacg tgt        53

<210> SEQ ID NO 20
<211> LENGTH: 53
<212> TYPE: DNA
<213> ORGANISM: Artificial Sequence
<220> FEATURE:
<223> OTHER INFORMATION: Synthetic Construct

<400> SEQUENCE: 20
caagcagaag acggcatacg agatctagta cggtgactgg agttcagacg tgt        53

<210> SEQ ID NO 21
<211> LENGTH: 53
<212> TYPE: DNA
<213> ORGANISM: Artificial Sequence
<220> FEATURE:
<223> OTHER INFORMATION: Synthetic Construct

<400> SEQUENCE: 21
caagcagaag acggcatacg agatttctgc ctgtgactgg agttcagacg tgt        53

<210> SEQ ID NO 22
<211> LENGTH: 53
<212> TYPE: DNA
<213> ORGANISM: Artificial Sequence
<220> FEATURE:
<223> OTHER INFORMATION: Synthetic Construct

<400> SEQUENCE: 22
caagcagaag acggcatacg agatgctcag gagtgactgg agttcagacg tgt        53

<210> SEQ ID NO 23
<211> LENGTH: 53
<212> TYPE: DNA
<213> ORGANISM: Artificial Sequence
<220> FEATURE:
<223> OTHER INFORMATION: Synthetic Construct

<400> SEQUENCE: 23
caagcagaag acggcatacg agataggagt ccgtgactgg agttcagacg tgt        53

<210> SEQ ID NO 24
<211> LENGTH: 53
<212> TYPE: DNA
<213> ORGANISM: Artificial Sequence
<220> FEATURE:
<223> OTHER INFORMATION: Synthetic Construct

<400> SEQUENCE: 24
caagcagaag acggcatacg agatcatgcc tagtgactgg agttcagacg tgt        53

<210> SEQ ID NO 25
<211> LENGTH: 53
<212> TYPE: DNA
<213> ORGANISM: Artificial Sequence
<220> FEATURE:
<223> OTHER INFORMATION: Synthetic Construct
```

<400> SEQUENCE: 25
caagcagaag acggcatacg agatgtagag aggtgactgg agttcagacg tgt     53

<210> SEQ ID NO 26
<211> LENGTH: 53
<212> TYPE: DNA
<213> ORGANISM: Artificial Sequence
<220> FEATURE:
<223> OTHER INFORMATION: Synthetic Construct

<400> SEQUENCE: 26
caagcagaag acggcatacg agatcctctc tggtgactgg agttcagacg tgt     53

<210> SEQ ID NO 27
<211> LENGTH: 43
<212> TYPE: DNA
<213> ORGANISM: Artificial Sequence
<220> FEATURE:
<223> OTHER INFORMATION: Synthetic Construct

<400> SEQUENCE: 27
aagacgtgtg ctcttccgaa cgcttcccac aggtctctgc tag     43

<210> SEQ ID NO 28
<211> LENGTH: 40
<212> TYPE: DNA
<213> ORGANISM: Artificial Sequence
<220> FEATURE:
<223> OTHER INFORMATION: Synthetic Construct

<400> SEQUENCE: 28
aagacgtgtg ctcttccgaa ccccactttt cctcttgcag     40

<210> SEQ ID NO 29
<211> LENGTH: 40
<212> TYPE: DNA
<213> ORGANISM: Artificial Sequence
<220> FEATURE:
<223> OTHER INFORMATION: Synthetic Construct

<400> SEQUENCE: 29
aagacgtgtg ctcttccgaa tccaggtccc cagcccaacc     40

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct

<400> SEQUENCE: 30
aagacgtgtg ctcttccgaa attccatggg actgactttc     40

<210> SEQ ID NO 31
<211> LENGTH: 41
<212> TYPE: DNA
<213> ORGANISM: Artificial Sequence
<220> FEATURE:
<223> OTHER INFORMATION: Synthetic Construct

<400> SEQUENCE: 31
aagacgtgtg ctcttccgaa atacggccag gcattgaagt c     41

<210> SEQ ID NO 32
<211> LENGTH: 40

```
<212> TYPE: DNA
<213> ORGANISM: Artificial Sequence
<220> FEATURE:
<223> OTHER INFORMATION: Synthetic Construct

<400> SEQUENCE: 32
aagacgtgtg ctcttccgaa cctctgactg ctcttttcac                            40

<210> SEQ ID NO 33
<211> LENGTH: 40
<212> TYPE: DNA
<213> ORGANISM: Artificial Sequence
<220> FEATURE:
<223> OTHER INFORMATION: Synthetic Construct

<400> SEQUENCE: 33
aagacgtgtg ctcttccgaa gggaagggac agaagatgac                            40

<210> SEQ ID NO 34
<211> LENGTH: 41
<212> TYPE: DNA
<213> ORGANISM: Artificial Sequence
<220> FEATURE:
<223> OTHER INFORMATION: Synthetic Construct

<400> SEQUENCE: 34
aagacgtgtg ctcttccgaa aagctcccag aatgccagag g                          41

<210> SEQ ID NO 35
<211> LENGTH: 40
<212> TYPE: DNA
<213> ORGANISM: Artificial Sequence
<220> FEATURE:
<223> OTHER INFORMATION: Synthetic Construct

<400> SEQUENCE: 35
aagacgtgtg ctcttccgaa gccctgtcgt ctctccagcc                            40

<210> SEQ ID NO 36
<211> LENGTH: 40
<212> TYPE: DNA
<213> ORGANISM: Artificial Sequence
<220> FEATURE:
<223> OTHER INFORMATION: Synthetic Construct

<400> SEQUENCE: 36
aagacgtgtg ctcttccgaa tgccctgact ttcaactctg                            40

<210> SEQ ID NO 37
<211> LENGTH: 41
<212> TYPE: DNA
<213> ORGANISM: Artificial Sequence
<220> FEATURE:
<223> OTHER INFORMATION: Synthetic Construct

<400> SEQUENCE: 37
aagacgtgtg ctcttccgaa tgctgtgact gcttgtagat g                          41

<210> SEQ ID NO 38
<211> LENGTH: 40
<212> TYPE: DNA
<213> ORGANISM: Artificial Sequence
<220> FEATURE:
<223> OTHER INFORMATION: Synthetic Construct

<400> SEQUENCE: 38
```
aagacgtgtg ctcttccgaa ccctgtgcag ctgtgggttg                    40

<210> SEQ ID NO 39
<211> LENGTH: 41
<212> TYPE: DNA
<213> ORGANISM: Artificial Sequence
<220> FEATURE:
<223> OTHER INFORMATION: Synthetic Construct

<400> SEQUENCE: 39
aagacgtgtg ctcttccgaa ccttaacccc tcctcccaga g                  41

<210> SEQ ID NO 40
<211> LENGTH: 40
<212> TYPE: DNA
<213> ORGANISM: Artificial Sequence
<220> FEATURE:
<223> OTHER INFORMATION: Synthetic Construct

<400> SEQUENCE: 40
aagacgtgtg ctcttccgaa ggtccccagg cctctgattc                    40

<210> SEQ ID NO 41
<211> LENGTH: 40
<212> TYPE: DNA
<213> ORGANISM: Artificial Sequence
<220> FEATURE:
<223> OTHER INFORMATION: Synthetic Construct

<400> SEQUENCE: 41
aagacgtgtg ctcttccgaa gcccaggggt cagaggcaag                    40

<210> SEQ ID NO 42
<211> LENGTH: 42
<212> TYPE: DNA
<213> ORGANISM: Artificial Sequence
<220> FEATURE:
<223> OTHER INFORMATION: Synthetic Construct

<400> SEQUENCE: 42
aagacgtgtg ctcttccgaa ttgccacagg tctccccaag gc                 42

<210> SEQ ID NO 43
<211> LENGTH: 40
<212> TYPE: DNA
<213> ORGANISM: Artificial Sequence
<220> FEATURE:
<223> OTHER INFORMATION: Synthetic Construct

<400> SEQUENCE: 43
aagacgtgtg ctcttccgaa ctccaccgct tcttgtcctg                    40

<210> SEQ ID NO 44
<211> LENGTH: 43
<212> TYPE: DNA
<213> ORGANISM: Artificial Sequence
<220> FEATURE:
<223> OTHER INFORMATION: Synthetic Construct

<400> SEQUENCE: 44
aagacgtgtg ctcttccgaa tactgcctct tgcttctctt ttc                43

<210> SEQ ID NO 45
<211> LENGTH: 41
<212> TYPE: DNA
<213> ORGANISM: Artificial Sequence

```
<220> FEATURE:
<223> OTHER INFORMATION: Synthetic Construct

<400> SEQUENCE: 45
aagacgtgtg ctcttccgaa acggcatttt gagtgttaga c                41

<210> SEQ ID NO 46
<211> LENGTH: 45
<212> TYPE: DNA
<213> ORGANISM: Artificial Sequence
<220> FEATURE:
<223> OTHER INFORMATION: Synthetic Construct

<400> SEQUENCE: 46
aagacgtgtg ctcttccgaa ctcagattca cttttatcac ctttc            45

<210> SEQ ID NO 47
<211> LENGTH: 41
<212> TYPE: DNA
<213> ORGANISM: Artificial Sequence
<220> FEATURE:
<223> OTHER INFORMATION: Synthetic Construct

<400> SEQUENCE: 47
aagacgtgtg ctcttccgaa atgaaggcag gatgagaatg g                41

<210> SEQ ID NO 48
<211> LENGTH: 43
<212> TYPE: DNA
<213> ORGANISM: Artificial Sequence
<220> FEATURE:
<223> OTHER INFORMATION: Synthetic Construct

<400> SEQUENCE: 48
aagacgtgtg ctcttccgaa gaaccatctt ttaactcagg tac              43

<210> SEQ ID NO 49
<211> LENGTH: 40
<212> TYPE: DNA
<213> ORGANISM: Artificial Sequence
<220> FEATURE:
<223> OTHER INFORMATION: Synthetic Construct

<400> SEQUENCE: 49
aagacgtgtg ctcttccgaa tgtcagtggg gaacaagaag                  40

<210> SEQ ID NO 50
<211> LENGTH: 41
<212> TYPE: DNA
<213> ORGANISM: Artificial Sequence
<220> FEATURE:
<223> OTHER INFORMATION: Synthetic Construct

<400> SEQUENCE: 50
aagacgtgtg ctcttccgaa catgtgatgt catctctcct c                41

<210> SEQ ID NO 51
<211> LENGTH: 54
<212> TYPE: DNA
<213> ORGANISM: Artificial Sequence
<220> FEATURE:
<223> OTHER INFORMATION: Synthetic Construct

<400> SEQUENCE: 51
gtgactggag ttcagacgtg tgctcttccg atcttgctag ggggctgggg ttgg  54
```

<210> SEQ ID NO 52
<211> LENGTH: 55
<212> TYPE: DNA
<213> ORGANISM: Artificial Sequence
<220> FEATURE:
<223> OTHER INFORMATION: Synthetic Construct

<400> SEQUENCE: 52
gtgactggag ttcagacgtg tgctcttccg atctccagac tgccttccgg gtcac        55

<210> SEQ ID NO 53
<211> LENGTH: 54
<212> TYPE: DNA
<213> ORGANISM: Artificial Sequence
<220> FEATURE:
<223> OTHER INFORMATION: Synthetic Construct

<400> SEQUENCE: 53
gtgactggag ttcagacgtg tgctcttccg atctccccag cccaaccctt gtcc         54

<210> SEQ ID NO 54
<211> LENGTH: 54
<212> TYPE: DNA
<213> ORGANISM: Artificial Sequence
<220> FEATURE:
<223> OTHER INFORMATION: Synthetic Construct

<400> SEQUENCE: 54
gtgactggag ttcagacgtg tgctcttccg atctactgac tttctgctct tgtc         54

<210> SEQ ID NO 55
<211> LENGTH: 54
<212> TYPE: DNA
<213> ORGANISM: Artificial Sequence
<220> FEATURE:
<223> OTHER INFORMATION: Synthetic Construct

<400> SEQUENCE: 55
gtgactggag ttcagacgtg tgctcttccg atctcaggca ttgaagtctc atgg         54

<210> SEQ ID NO 56
<211> LENGTH: 55
<212> TYPE: DNA
<213> ORGANISM: Artificial Sequence
<220> FEATURE:
<223> OTHER INFORMATION: Synthetic Construct

<400> SEQUENCE: 56
gtgactggag ttcagacgtg tgctcttccg atcttgactg ctcttttcac ccatc        55

<210> SEQ ID NO 57
<211> LENGTH: 54
<212> TYPE: DNA
<213> ORGANISM: Artificial Sequence
<220> FEATURE:
<223> OTHER INFORMATION: Synthetic Construct

<400> SEQUENCE: 57
gtgactggag ttcagacgtg tgctcttccg atctaagatg acaggggcca ggag         54

<210> SEQ ID NO 58
<211> LENGTH: 54
<212> TYPE: DNA
<213> ORGANISM: Artificial Sequence
<220> FEATURE:
<223> OTHER INFORMATION: Synthetic Construct

<400> SEQUENCE: 58
gtgactggag ttcagacgtg tgctcttccg atctccccgt ggcccctgca ccag         54

<210> SEQ ID NO 59
<211> LENGTH: 55
<212> TYPE: DNA
<213> ORGANISM: Artificial Sequence
<220> FEATURE:
<223> OTHER INFORMATION: Synthetic Construct

<400> SEQUENCE: 59
gtgactggag ttcagacgtg tgctcttccg atcttgtcgt ctctccagcc ccagc        55

<210> SEQ ID NO 60
<211> LENGTH: 58
<212> TYPE: DNA
<213> ORGANISM: Artificial Sequence
<220> FEATURE:
<223> OTHER INFORMATION: Synthetic Construct

<400> SEQUENCE: 60
gtgactggag ttcagacgtg tgctcttccg atctactttc aactctgtct ccttcctc    58

<210> SEQ ID NO 61
<211> LENGTH: 54
<212> TYPE: DNA
<213> ORGANISM: Artificial Sequence
<220> FEATURE:
<223> OTHER INFORMATION: Synthetic Construct

<400> SEQUENCE: 61
gtgactggag ttcagacgtg tgctcttccg atcttgcttg tagatggcca tggc         54

<210> SEQ ID NO 62
<211> LENGTH: 58
<212> TYPE: DNA
<213> ORGANISM: Artificial Sequence
<220> FEATURE:
<223> OTHER INFORMATION: Synthetic Construct

<400> SEQUENCE: 62
gtgactggag ttcagacgtg tgctcttccg atctcctgtg cagctgtggg ttgattcc    58

<210> SEQ ID NO 63
<211> LENGTH: 54
<212> TYPE: DNA
<213> ORGANISM: Artificial Sequence
<220> FEATURE:
<223> OTHER INFORMATION: Synthetic Construct

<400> SEQUENCE: 63
gtgactggag ttcagacgtg tgctcttccg atctctccca gagacccag ttgc          54

<210> SEQ ID NO 64
<211> LENGTH: 55
<212> TYPE: DNA
<213> ORGANISM: Artificial Sequence
<220> FEATURE:
<223> OTHER INFORMATION: Synthetic Construct

<400> SEQUENCE: 64
gtgactggag ttcagacgtg tgctcttccg atctcccagg cctctgattc ctcac        55

<210> SEQ ID NO 65

<210> SEQ ID NO 65
<211> LENGTH: 54
<212> TYPE: DNA
<213> ORGANISM: Artificial Sequence
<220> FEATURE:
<223> OTHER INFORMATION: Synthetic Construct

<400> SEQUENCE: 65
gtgactggag ttcagacgtg tgctcttccg atctgggtca gaggcaagca gagg          54

<210> SEQ ID NO 66
<211> LENGTH: 58
<212> TYPE: DNA
<213> ORGANISM: Artificial Sequence
<220> FEATURE:
<223> OTHER INFORMATION: Synthetic Construct

<400> SEQUENCE: 66
gtgactggag ttcagacgtg tgctcttccg atctgcctca tcttgggcct gtgttatc      58

<210> SEQ ID NO 67
<211> LENGTH: 54
<212> TYPE: DNA
<213> ORGANISM: Artificial Sequence
<220> FEATURE:
<223> OTHER INFORMATION: Synthetic Construct

<400> SEQUENCE: 67
gtgactggag ttcagacgtg tgctcttccg atctccgctt cttgtcctgc ttgc          54

<210> SEQ ID NO 68
<211> LENGTH: 60
<212> TYPE: DNA
<213> ORGANISM: Artificial Sequence
<220> FEATURE:
<223> OTHER INFORMATION: Synthetic Construct

<400> SEQUENCE: 68
gtgactggag ttcagacgtg tgctcttccg atcttgcctc ttgcttctct tttcctatcc    60

<210> SEQ ID NO 69
<211> LENGTH: 60
<212> TYPE: DNA
<213> ORGANISM: Artificial Sequence
<220> FEATURE:
<223> OTHER INFORMATION: Synthetic Construct

<400> SEQUENCE: 69
gtgactggag ttcagacgtg tgctcttccg atctggcatt tgagtgtta gactggaaac     60

<210> SEQ ID NO 70
<211> LENGTH: 60
<212> TYPE: DNA
<213> ORGANISM: Artificial Sequence
<220> FEATURE:
<223> OTHER INFORMATION: Synthetic Construct

<400> SEQUENCE: 70
gtgactggag ttcagacgtg tgctcttccg atctattcac ttttatcacc tttccttgcc    60

<210> SEQ ID NO 71
<211> LENGTH: 59
<212> TYPE: DNA
<213> ORGANISM: Artificial Sequence
<220> FEATURE:
<223> OTHER INFORMATION: Synthetic Construct

<400> SEQUENCE: 71

```
gtgactggag ttcagacgtg tgctcttccg atcttgaagg caggatgaga atggaatcc        59

<210> SEQ ID NO 72
<211> LENGTH: 60
<212> TYPE: DNA
<213> ORGANISM: Artificial Sequence
<220> FEATURE:
<223> OTHER INFORMATION: Synthetic Construct

<400> SEQUENCE: 72
gtgactggag ttcagacgtg tgctcttccg atctggtact gtgtatatac ttacttctcc       60

<210> SEQ ID NO 73
<211> LENGTH: 54
<212> TYPE: DNA
<213> ORGANISM: Artificial Sequence
<220> FEATURE:
<223> OTHER INFORMATION: Synthetic Construct

<400> SEQUENCE: 73
gtgactggag ttcagacgtg tgctcttccg atctgtgggg aacaagaagt ggag             54

<210> SEQ ID NO 74
<211> LENGTH: 55
<212> TYPE: DNA
<213> ORGANISM: Artificial Sequence
<220> FEATURE:
<223> OTHER INFORMATION: Synthetic Construct

<400> SEQUENCE: 74
gtgactggag ttcagacgtg tgctcttccg atctgtcatc tctcctccct gcttc            55
```